(12) United States Patent
Inoue et al.

(10) Patent No.: US 9,056,883 B2
(45) Date of Patent: *Jun. 16, 2015

(54) ORGANOMETALLIC COMPLEX, LIGHT-EMITTING ELEMENT, LIGHT-EMITTING DEVICE, ELECTRONIC DEVICE, AND LIGHTING DEVICE

(75) Inventors: Hideko Inoue, Kanagawa (JP); Tomoka Nakagawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1024 days.

This patent is subject to a terminal disclaimer.

(21) Appl. No.: 13/079,936

(22) Filed: Apr. 5, 2011

(65) Prior Publication Data

US 2011/0245495 A1    Oct. 6, 2011

(30) Foreign Application Priority Data

Apr. 6, 2010    (JP) .................. 2010-087626

(51) Int. Cl.
| | | |
|---|---|---|
| C09K 11/06 | (2006.01) | |
| H01L 51/54 | (2006.01) | |
| C07F 15/00 | (2006.01) | |
| H01L 51/00 | (2006.01) | |
| H01L 51/50 | (2006.01) | |

(52) U.S. Cl.
CPC ........ *C07F 15/0033* (2013.01); *H01L 51/0085* (2013.01); *H01L 51/5016* (2013.01); *H01L 51/0087* (2013.01); *C07F 15/0086* (2013.01); *C09K 2211/1044* (2013.01); *C09K 11/06* (2013.01); *C09K 2211/185* (2013.01)

(58) Field of Classification Search
None
See application file for complete search history.

(56) References Cited

U.S. PATENT DOCUMENTS

| | | |
|---|---|---|
| 6,656,608 B1 | 12/2003 | Kita et al. |
| 6,803,720 B2 | 10/2004 | Kwong et al. |
| 6,921,915 B2 | 7/2005 | Takiguchi et al. |
| 6,974,639 B2 | 12/2005 | Tsuboyama et al. |
| 7,264,890 B2 | 9/2007 | Kita et al. |
| 7,316,851 B2 | 1/2008 | Kita et al. |
| 7,354,662 B2 | 4/2008 | Tsuboyama et al. |
| 7,871,713 B2 | 1/2011 | Kita et al. |
| 7,960,038 B2 | 6/2011 | Ohsawa et al. |
| 7,999,254 B2 | 8/2011 | Inoue et al. |
| 8,084,145 B2 | 12/2011 | Inoue et al. |
| 8,101,755 B2 | 1/2012 | Inoue et al. |
| 8,227,975 B2 | 7/2012 | Inoue et al. |
| 8,247,086 B2 | 8/2012 | Inoue et al. |
| 8,399,665 B2 * | 3/2013 | Inoue et al. .................. 544/225 |
| 8,541,574 B2 | 9/2013 | Inoue et al. |
| 8,822,682 B2 * | 9/2014 | Inoue et al. .................. 544/225 |
| 2004/0062951 A1 | 4/2004 | Kita et al. |
| 2004/0072019 A1 | 4/2004 | Kita et al. |
| 2006/0127696 A1 * | 6/2006 | Stossel et al. ................. 428/690 |
| 2006/0263637 A1 | 11/2006 | Ohsawa et al. |
| 2007/0161793 A1 | 7/2007 | Murata et al. |
| 2007/0244320 A1 | 10/2007 | Inoue et al. |
| 2008/0149923 A1 | 6/2008 | Ohsawa et al. |
| 2008/0231177 A1 | 9/2008 | Nomura et al. |
| 2008/0233432 A1 | 9/2008 | Inoue et al. |
| 2008/0286604 A1 | 11/2008 | Inoue et al. |
| 2008/0305361 A1 | 12/2008 | Inoue et al. |
| 2008/0312437 A1 | 12/2008 | Inoue et al. |

(Continued)

FOREIGN PATENT DOCUMENTS

| | | |
|---|---|---|
| EP | 1 013 740 A2 | 6/2000 |
| EP | 1 238 981 A2 | 9/2002 |

(Continued)

OTHER PUBLICATIONS

Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English abstract).

(Continued)

*Primary Examiner* — Marie R. Yamnitzky
(74) *Attorney, Agent, or Firm* — Husch Blackwell LLP

(57) ABSTRACT

An object is to provide a novel organometallic complex capable of emitting phosphorescence by using, as a ligand, an organic compound with which a variety of derivatives can be easily synthesized. Another object is to provide an organometallic complex having high heat resistance. Other objects are to provide a light-emitting element having high emission efficiency and to provide a light-emitting device, an electronic device, and a lighting device having reduced power consumption. Provided are an organometallic complex including a structure represented by the following General Formula (G1), and a light-emitting element, a light-emitting device, an electronic device, and a lighting device formed using the organometallic complex including the structure represented by the following General Formula (G1).

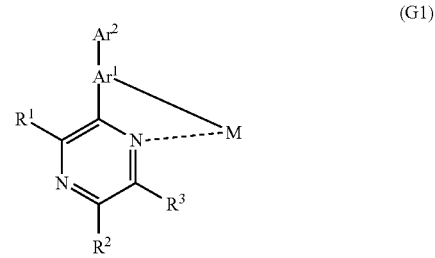

(G1)

33 Claims, 18 Drawing Sheets

(56) References Cited

U.S. PATENT DOCUMENTS

| | | |
|---|---|---|
| 2009/0015143 A1 | 1/2009 | Inoue et al. |
| 2009/0183982 A1 | 7/2009 | Inoue et al. |
| 2010/0059741 A1 | 3/2010 | Ohsawa et al. |
| 2010/0145044 A1 | 6/2010 | Inoue et al. |
| 2014/0371448 A1 | 12/2014 | Inoue et al. |

FOREIGN PATENT DOCUMENTS

| | | |
|---|---|---|
| EP | 1 239 526 A2 | 9/2002 |
| EP | 1 731 585 A2 | 12/2006 |
| EP | 1 731 586 A2 | 12/2006 |
| EP | 1 764 401 A1 | 3/2007 |
| JP | 2002-332291 A | 11/2002 |
| JP | 2002-332292 A | 11/2002 |
| JP | 2004-515895 | 5/2004 |
| JP | 2007-177252 A | 7/2007 |
| JP | 2007-182429 A | 7/2007 |
| JP | 2009-013168 A | 1/2009 |
| JP | 5641860 B2 | 12/2014 |
| WO | WO 02/47457 A2 | 6/2002 |
| WO | WO 2005/101912 A1 | 10/2005 |
| WO | WO 2007/066556 A1 | 6/2007 |

OTHER PUBLICATIONS

Zhang, G.-L. et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English translation).

* cited by examiner

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to an organometallic complex. In particular, the present invention relates to an organometallic complex that is capable of converting a triplet excited state into luminescence.

2. Description of the Related Art

In recent years, there has been an active development of light-emitting elements in each of which an organic or inorganic compound having a light-emitting property is used as a light-emitting substance. In particular, a light-emitting element called an EL (electroluminescence) element has attracted attention as a next-generation flat panel display element because it has a simple structure, in which a light-emitting layer containing a light-emitting substance is provided between electrodes, and characteristics, such as feasibility of being thinner and more lightweight and responsive to input signals and capability of driving with direct current at low voltage. Moreover, a display using such a light-emitting element has high contrast, excellent image qualities, and a wide viewing angle. Furthermore, such a light-emitting element is a planar light source, and accordingly its applications to light sources such as backlights of liquid crystal displays and lighting have been under contemplation.

In the case where the light-emitting substance is an organic compound having a light-emitting property, the emission mechanism of the light-emitting element is a carrier-injection type. Specifically, by application of a voltage to electrodes between which the light-emitting layer is interposed, electrons and holes injected from the electrodes recombine to raise the light-emitting substance to an excited state, and light is emitted when the substance in the excited state returns to the ground state. Possible excited states are a singlet excited state (S*) and a triplet excited state (T*). In addition, the ratio of S* to T* formed in the light-emitting element is statistically considered to be 1:3.

In general, the ground state of an organic compound having a light-emitting property is a singlet state. Light emission from a singlet excited state (S*), which is electron transition between the same multiplicities, is referred to as fluorescence, and light emission from a triplet excited state (T*), which is electron transition between different multiplicities, is referred to as phosphorescence. At room temperature, observations of a compound which emits fluorescence (hereinafter referred to as a fluorescent compound) usually show only fluorescence without phosphorescence. Hence, the internal quantum efficiency (the ratio of generated photons to injected carriers) of a light-emitting element using a fluorescent compound is assumed to have a theoretical limit of 25% based on a S*-to-T* ratio of 1:3.

On the other hand, use of a phosphorescent compound can increase the internal quantum efficiency to 75% to 100% in theory. In other words, an element using a phosphorescent compound can have three to four times as high emission efficiency as that of an element using a fluorescent compound. For these reasons, a light-emitting element using a phosphorescent compound has been actively developed in recent years in order to achieve a highly-efficient light-emitting element (e.g., see Non-Patent Document 1). As the phosphorescent compound, organometallic complexes that have iridium or the like as a central metal have particularly attracted attention because of their high phosphorescence quantum yield.

Further, a light-emitting element using a phosphorescent compound is disclosed which uses a light-emitting layer containing an organic low molecular hole-transport substance and an organic low molecular electron-transport substance as host substances and the phosphorescent compound as a dopant and has improved lifetime and efficiency (see Patent Document 1).

An advantage of use of the highly-efficient light-emitting element is that power consumption of an electronic device using the light-emitting element can be reduced, for example. With recent attention to the energy problems, power consumption is becoming a major factor controlling the trends in consumer purchases and thus attains considerable importance.

REFERENCES

Patent Document

Patent Document 1: Japanese Translation of PCT International Application No. 2004-515895

Non-Patent Document

Non-Patent Document 1: Zhang, Guo-Lin and five others (2004) *Gaodeng Xuexiao Huaxue Xuebao*, vol. 25, No. 3, pp. 397-400.

SUMMARY OF THE INVENTION

An object of one embodiment of the present invention is to provide a novel phosphorescent organometallic complex including an organic compound, as a ligand, with which a variety of derivatives can be easily synthesized. Another object of one embodiment of the present invention is to provide a phosphorescent organometallic complex having high heat resistance.

Other objects of one embodiment of the present invention are to provide a light-emitting element having high emission efficiency and to provide a light-emitting device, an electronic device, and a lighting device each having reduced power consumption.

One embodiment of the present invention is an organometallic complex that undergoes ortho-metalation in which an arylpyrazine derivative represented by General Formula (G0) below is coordinated to an ion of a metal that belongs to Group 9 or Group 10 to form a bulky structure. The ortho-metalated organometallic complex in which the ion of a metal that belongs to Group 9 or Group 10 is coordinated to the arylpyrazine derivative represented by General Formula (G0) has high heat resistance due to the bulky structure. Further, the ortho-metalated organometallic complex in which the ion of a metal that belongs to Group 9 or Group 10 is coordinated to the arylpyrazine derivative represented by General Formula (G0) is an organometallic complex, the concentration quenching of which is suppressed by having the bulky structure.

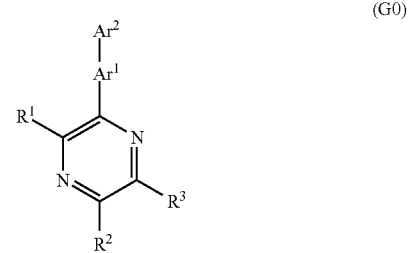

In General Formula (G0), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms.

Thus, one embodiment of the present invention is an organometallic complex including a structure represented by the following General Formula (G1).

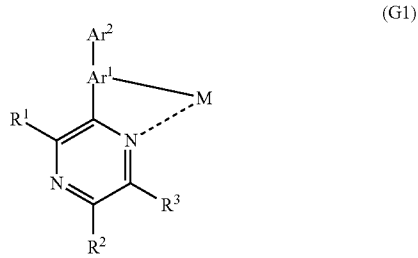

In General Formula (G1), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. Further, M is a central metal and represents a Group 9 element or a Group 10 element.

The organometallic complex including the structure represented by General Formula (G1) above is preferably specifically an organometallic complex represented by the following General Formula (G3) for easier synthesis.

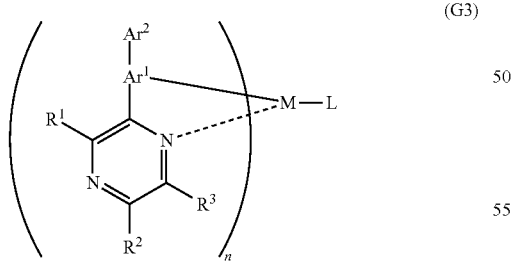

In General Formula (G3), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. Further, M is a central metal and represents a Group 9 element or a Group 10 element. L represents a monoanionic ligand. Moreover, n is 2 when the central metal is a Group 9 element or n is 1 when the central metal is a Group 10 element.

The above monoanionic ligand L is preferably any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which each of two ligands is nitrogen, and particularly preferably, any of monoanionic ligands represented by General Formulae (L1) to (L6) below. These ligands are effective because of their high coordination ability and reasonable availability.

(Ligands: L)

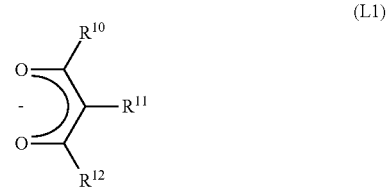

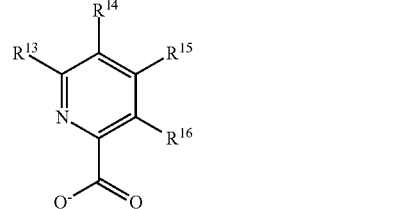

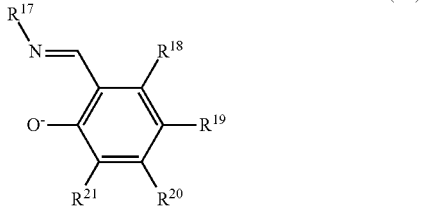

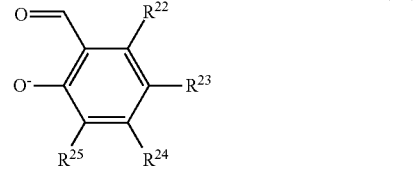

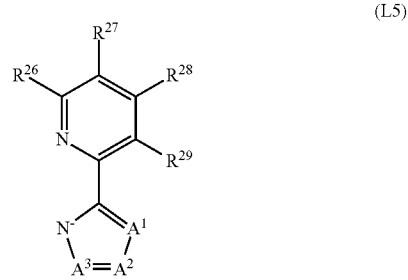

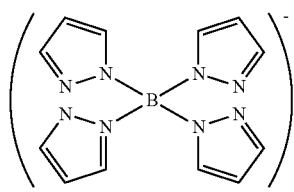

(L6)

In General Formulae (L1) to (L6), $R^{10}$ to $R^{29}$ separately represent any of hydrogen, an alkyl group having 1 to 4 carbon atoms, a halogen, a haloalkyl group, an alkoxy group having 1 to 4 carbon atoms, and an alkylthio group having 1 to 4 carbon atoms. Further, $A^1$ to $A^3$ separately represent nitrogen, sp² hybridized carbon bonded to hydrogen, or sp² carbon bonded to a substituent R. Note that the substituent R represents any of an alkyl group having 1 to 4 carbon atoms, a haloalkyl group having 1 to 4 carbon atoms, and a phenyl group.

The central metal is preferably a metal that provides a heavy atom effect in order to obtain more efficient phosphorescence. Therefore, in one embodiment of the present invention, the central metal M in any of the above organometallic complexes which are embodiments of the present invention is iridium or platinum.

The organometallic complex including the structure represented by General Formula (G1) above is preferably specifically an organometallic complex represented by the following General Formula (G5) for easier synthesis.

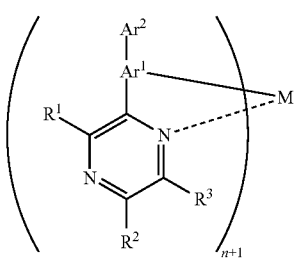

(G5)

In General Formula (G5), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. Further, M is a central metal and represents a Group 9 element or a Group 10 element. Moreover, n is 2 when the central metal is a Group 9 element or n is 1 when the central metal is a Group 10 element.

One embodiment of the present invention is an organometallic complex including a structure represented by the following General Formula (G7).

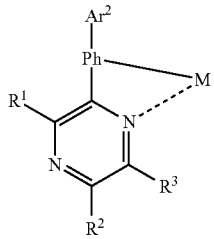

(G7)

In General Formula (G7), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. Ph represents a benzene ring. $Ar^2$ represents a condensed aromatic hydrocarbon group having 10 to 13 carbon atoms. Further, M is a central metal and represents a Group 9 element or a Group 10 element.

One embodiment of the present invention is an organometallic complex including a structure represented by the following General Formula (G10).

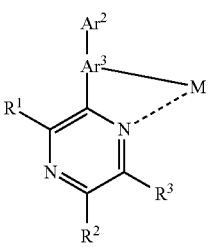

(G10)

In General Formula (G10), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $Ar^3$ represents a naphthalene ring or a fluorene ring. $Ar^2$ represents an aromatic hydrocarbon group having 6 to 13 carbon atoms. Further, M is a central metal and represents a Group 9 element or a Group 10 element.

In any of the above organometallic complexes which are embodiments of the present invention, $R^3$ is preferably hydrogen, because such a structure reduces the steric hindrance of a pyrazine derivative and increases synthesis yield accordingly.

Further, since the organometallic complexes which are embodiments of the present invention each have a bulky structure, they have excellent heat resistance and thermal stability.

Further, since the organometallic complexes which are embodiments of the present invention each emit phosphorescence, their application to a light-emitting element can increase the efficiency of the element. Hence, another embodiment of the present invention is a light-emitting element using any of the above organometallic complexes which are embodiments of the present invention.

In this case, any of the above organometallic complexes which are embodiments of the present invention is effectively used as a light-emitting substance in terms of emission efficiency. Therefore, another embodiment of the present invention is a light-emitting element in which any of the above organometallic complexes which are embodiments of the present invention is used as a light-emitting substance.

Other embodiments of the present invention are not only a light-emitting device including the light-emitting element but also an electronic device and a lighting device each including the light-emitting device. The light emitting device includes all the following modules in its category: a module in which a connector, for example, an FPC (flexible printed circuit), a TAB (tape automated bonding) tape, or a TCP (tape carrier package) is attached to a light-emitting device; a module provided with a printed wiring board at the end of a TAB tape or a TCP; and a module in which an IC (integrated circuit) is directly mounted on a light-emitting element by a COG (chip-on-glass) method.

According to the present invention, a novel phosphorescent organometallic complex having an organic compound, as a ligand, with which a variety of derivatives can be easily synthesized can be provided. Furthermore, according to one embodiment of the present invention, an organometallic complex having high heat resistance can be provided. Moreover, according to embodiments of the present invention, a light-emitting element, a light-emitting device, an electronic device, and a lighting device each including the organometallic complex having high heat resistance can be provided.

DETAILED DESCRIPTION OF THE INVENTION

Figure 1:
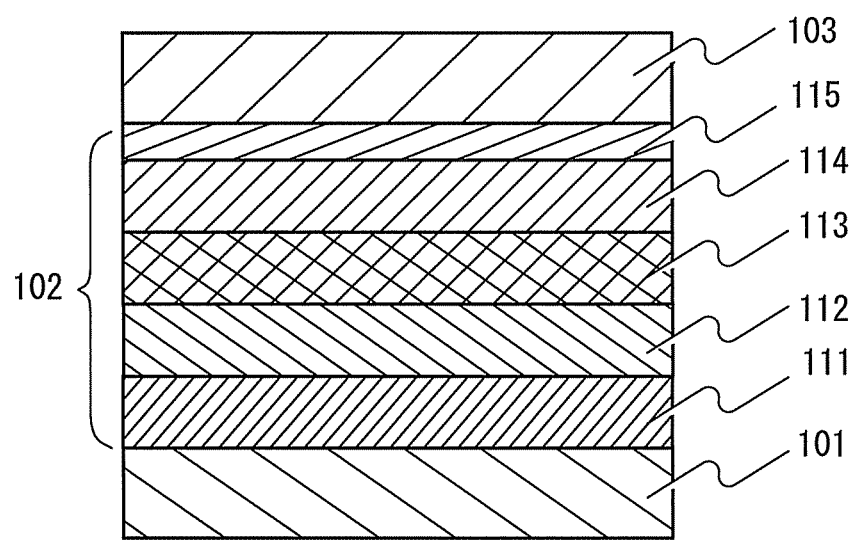
FIG. 1 illustrates a light-emitting element which is one embodiment of the present invention.

Embodiments of the present invention will now be described with reference to the accompanying drawings. Note that the invention is not limited to the description given below, and various changes and modifications can be made without departing from the spirit and scope of the invention. Therefore, the invention should not be construed as being limited to the description in the following embodiments.

Embodiment 1

In Embodiment 1, organometallic complexes which are embodiments of the present invention will be described.

One embodiment of the present invention is an organometallic complex that undergoes ortho-metalation in which an arylpyrazine derivative represented by General Formula (G0) below is coordinated to an ion of a metal that belongs to Group 9 or Group 10 to form a bulky structure. The ortho-metalated organometallic complex in which the ion of a metal that belongs to Group 9 or Group 10 is coordinated to the arylpyrazine derivative represented by General Formula (G0) has high heat resistance due to the bulky structure. Further, the ortho-metalated organometallic complex in which the ion of a metal that belongs to Group 9 or Group 10 is coordinated to the arylpyrazine derivative represented by General Formula (G0) is an organometallic complex, the concentration quenching of which is suppressed by having the bulky structure.

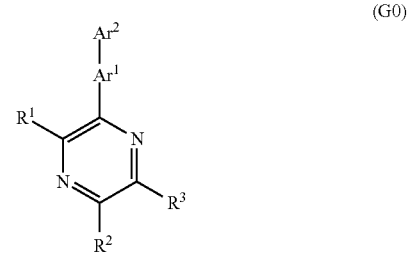

(G0)

In General Formula (G0), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent.

Thus, one embodiment of the present invention is an organometallic complex including the structure represented by the following General Formula (G1).

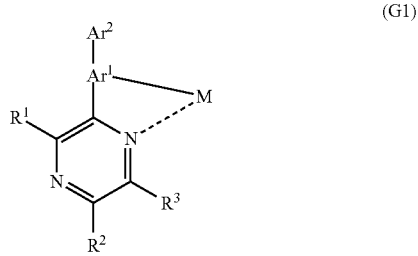

(G1)

In General Formula (G1), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent. Further, M is a central metal and represents a Group 9 element or a Group 10 element.

As the substituents represented as $R^1$ to $R^3$ in the above General Formula (G1), examples of the alkyl group having 1 to 4 carbon atoms are a methyl group, an ethyl group, a propyl group, an isopropyl group, a butyl group, a sec-butyl group, an isobutyl group, a tert-butyl group, and the like; examples of the alkoxy group having 1 to 4 carbon atoms are a methoxy group, an ethoxy group, a propoxy group, an isopropoxy group, a butoxy group, a sec-butoxy group, an isobutoxy group, a tert-butoxy group, and the like; and examples of the alkylthio group having 1 to 4 carbon atoms are a methylthio group, an ethylthio group, a propylthio group, an isopropylthio group, a butylthio group, a sec-butylthio group, an isobutylthio group, a tert-butylthio group, and the like.

In the above General Formula (G1), $R^3$ is preferably hydrogen, because such a structure reduces the steric hindrance of a pyrazine derivative and increases synthesis yield accordingly. Thus, a preferred embodiment of the present invention is an organometallic complex including a structure represented by the following General Formula (G2).

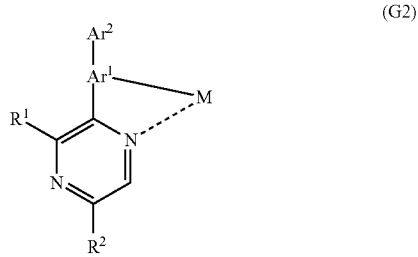

(G2)

In General Formula (G2), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent. Further, M is a central metal and represents a Group 9 element or a Group 10 element.

The organometallic complex including the structure represented by General Formula (G1) above is preferably specifically the organometallic complex represented by the following General Formula (G3) for easier synthesis.

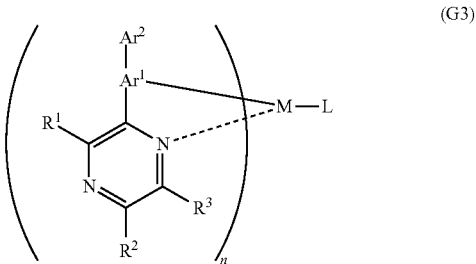

(G3)

In General Formula (G3), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent. Further, M is a central metal and represents a Group 9 element or a Group 10 element. L represents a monoanionic ligand. Moreover, n is 2 when the central metal is a Group 9 element or n is 1 when the central metal is a Group 10 element.

The organometallic complex including the structure represented by General Formula (G2) above is preferably specifically an organometallic complex represented by the following General Formula (G4) below to further facilitate synthesis.

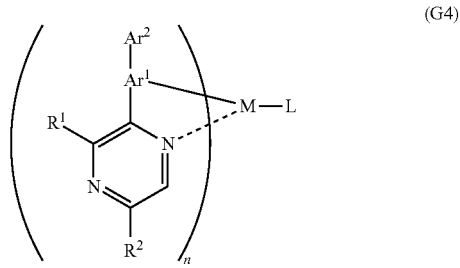

(G4)

In General Formula (G4), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent. Further, M is a central metal and represents a Group 9 element or a Group 10 element. L represents a monoanionic ligand. Moreover, n is 2 when the central metal is a Group 9 element or n is 1 when the central metal is a Group 10 element.

The above monoanionic ligand L is preferably any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which each of two ligands is nitrogen, and particularly preferably, any of monoanionic ligands represented by General Formulae (L1) to (L6) below. These ligands are effective because of their high coordination ability and reasonable availability.

(Ligands: L)

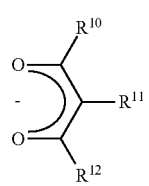
(L1)

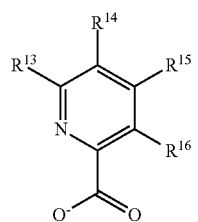
(L2)

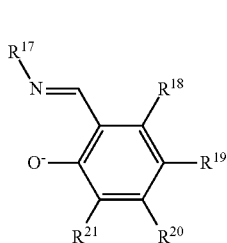
(L3)

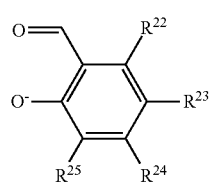
(L4)

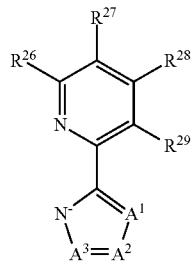
(L5)

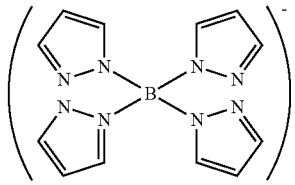
(L6)

In General Formulae (L1) to (L6), $R^{10}$ to $R^{29}$ separately represent any of hydrogen, an alkyl group having 1 to 4 carbon atoms, a halogen, a haloalkyl group, an alkoxy group having 1 to 4 carbon atoms, and an alkylthio group having 1 to 4 carbon atoms. Further, $A^1$ to $A^3$ separately represent nitrogen, sp² hybridized carbon bonded to hydrogen, or sp² carbon bonded to a substituent R. Note that the substituent R represents any of an alkyl group having 1 to 4 carbon atoms, a haloalkyl group having 1 to 4 carbon atoms, and a phenyl group.

The central metal is preferably a metal that provides a heavy atom effect in order to obtain more efficient phosphorescence. Therefore, in one embodiment of the present invention, the central metal M in any of the above organometallic complexes which are embodiments of the present invention is iridium or platinum.

The organometallic complex including the structure represented by General Formula (G1) above is preferably specifically the organometallic complex represented by the following General Formula (G5) for easier synthesis.

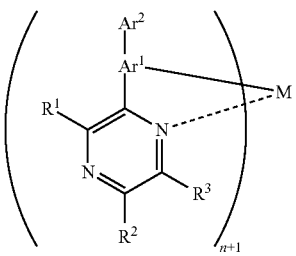
(G5)

In General Formula (G5), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent. Further, M is a central metal and represents a Group 9 element or a Group 10 element. Moreover, n is 2 when the central metal is a Group 9 element or n is 1 when the central metal is a Group 10 element.

The organometallic complex including the structure represented by General Formula (G2) above is preferably specifically an organometallic complex represented by the following General Formula (G6) for easier synthesis.

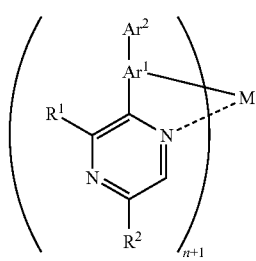

(G6)

In General Formula (G6), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent. Further, M is a central metal and represents a Group 9 element or a Group 10 element. Moreover, n is 2 when the central metal is a Group 9 element or n is 1 when the central metal is a Group 10 element.

Another embodiment of the present invention is an organometallic complex including the structure represented by the following General Formula (G7).

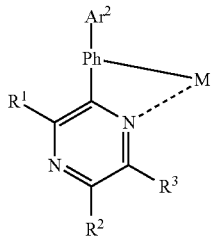

(G7)

In General Formula (G7), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. Ph represents a benzene ring that may have a substituent. $Ar^2$ represents a condensed aromatic hydrocarbon group having 10 to 13 carbon atoms and may have a substituent. Further, M is a central metal and represents a Group 9 element or a Group 10 element.

Another embodiment of the present invention is an organometallic complex including the structure represented by the following General Formula (G8).

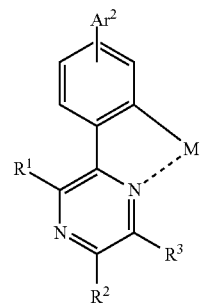

(G8)

In General Formula (G8), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $Ar^2$ represents a condensed aromatic hydrocarbon group having 10 to 13 carbon atoms and may have a substituent. Further, M is a central metal and represents a Group 9 element or a Group 10 element.

In the above General Formula (G8), $R^3$ is preferably hydrogen, because such a structure reduces the steric hindrance of a pyrazine derivative and increases synthesis yield accordingly. Thus, a preferred embodiment of the present invention is an organometallic complex including a structure represented by the following General Formula (G9).

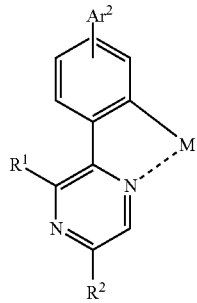

(G9)

In General Formula (G9), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. $Ar^2$ represents a condensed aromatic hydrocarbon group having 10 to 13 carbon atoms and may have a substituent. Further, M is a central metal and represents a Group 9 element or a Group 10 element.

Another embodiment of the present invention is an organometallic complex including a structure represented by the following General Formula (G10).

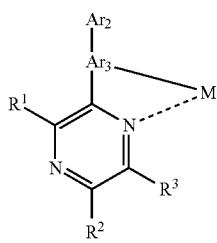

(G10)

In General Formula (G10), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $Ar^3$ represents a naphthalene ring that may have a substituent or a fluorene ring that may have a substituent. $Ar^2$ represents an aromatic hydrocarbon group having 6 to 13 carbon atoms and may have a substituent. Further, M is a central metal and represents a Group 9 element or a Group 10 element.

Another embodiment of the present invention is an organometallic complex including a structure represented by the following General Formula (G11).

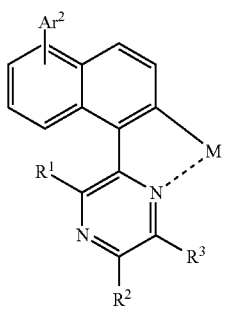

(G11)

In General Formula (G11), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

Another embodiment of the present invention is an organometallic complex including a structure represented by the following General Formula (G12).

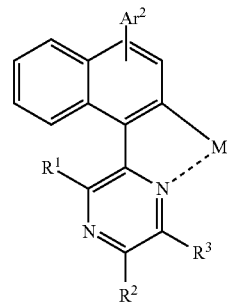

(G12)

In General Formula (G12), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

Another embodiment of the present invention is an organometallic complex including a structure represented by the following General Formula (G13).

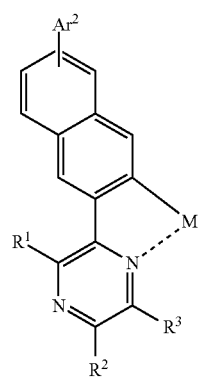

(G13)

In General Formula (G13), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

In the above General Formula (G11), $R^3$ is preferably hydrogen, because such a structure reduces the steric hindrance of a pyrazine derivative and increases synthesis yield accordingly. Thus, a preferred embodiment of the present invention is an organometallic complex including a structure represented by the following General Formula (G14).

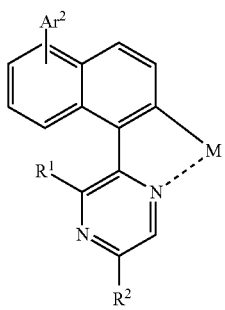

(G14)

In General Formula (G14), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

In the above General Formula (G12), $R^3$ is preferably hydrogen, because such a structure reduces the steric hindrance of a pyrazine derivative and increases synthesis yield accordingly. Thus, a preferred embodiment of the present invention is an organometallic complex including a structure represented by the following General Formula (G15).

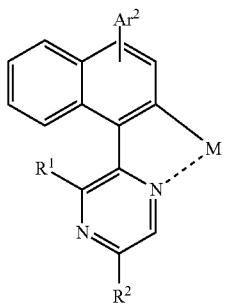

(G15)

In General Formula (G15), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

In the above General Formula (G13), $R^3$ is preferably hydrogen, because such a structure reduces the steric hindrance of a pyrazine derivative and increases synthesis yield accordingly. Thus, a preferred embodiment of the present invention is an organometallic complex including a structure represented by the following General Formula (G16).

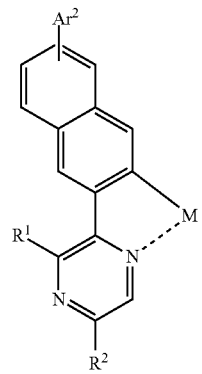

(G16)

In General Formula (G16), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

Another embodiment of the present invention is an organometallic complex including a structure represented by the following General Formula (G17).

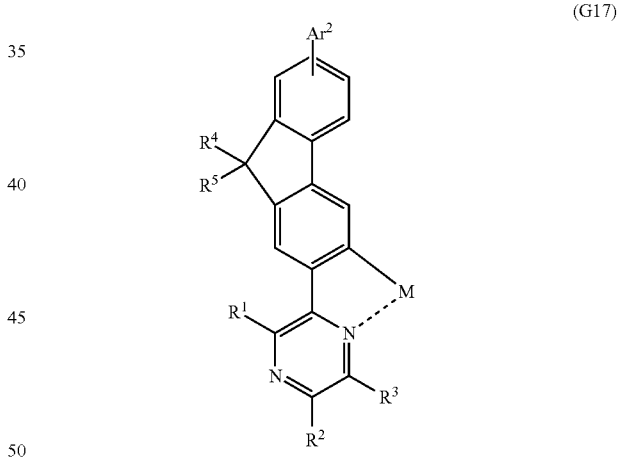

(G17)

In General Formula (G17), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $R^4$ and $R^5$ separately represent an alkyl group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

Another embodiment of the present invention is an organometallic complex including a structure represented by the following General Formula (G18).

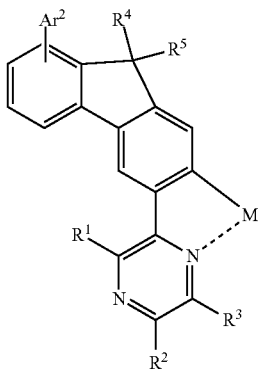

(G18)

In General Formula (G18), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. $R^4$ and $R^5$ separately represent an alkyl group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

In the above General Formula (G17), $R^3$ is preferably hydrogen, because such a structure reduces the steric hindrance of a pyrazine derivative and increases synthesis yield accordingly. Thus, a preferred embodiment of the present invention is an organometallic complex including a structure represented by the following General Formula (G19).

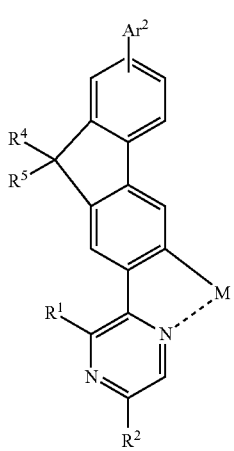

(G19)

In General Formula (G19), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^4$ and $R^5$ separately represent an alkyl group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

In General Formula (G18) above, $R^3$ is preferably hydrogen, because such a structure reduces the steric hindrance of a pyrazine derivative and increases synthesis yield accordingly. Thus, a preferred embodiment of the present invention is an organometallic complex including a structure represented by the following General Formula (G20).

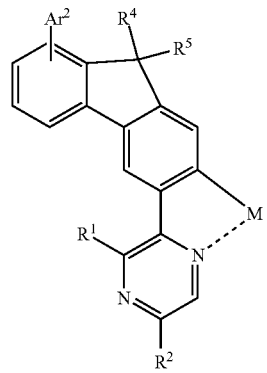

(G20)

In General Formula (G20), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^4$ and $R^5$ separately represent an alkyl group having 1 to 4 carbon atoms. $Ar^2$ represents an aromatic hydrocarbon group having 6 to 13 carbon atoms and may have a substituent. Further, M is a central metal and represents a Group 9 element or a Group 10 element.

Method of Synthesizing Arylpyrazine Derivative Represented by General Formula (G0)

The arylpyrazine derivative represented by General Formula (G0) below can be synthesized by any of Synthesis Schemes (a), (a'), and (a''), which are simple as illustrated below. Note that in each of Synthesis Schemes (a), (a'), and (a''), X represents a halogen element.

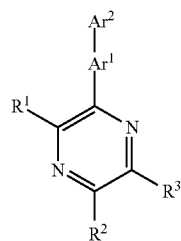

(G0)

In General Formula (G0), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent.

For example, as illustrated in Scheme (a) below, a lithium compound of aryl or a Grignard reagent of aryl, which is illustrate in (A1), is reacted with a pyrazine compound (A2), whereby the arylpyrazine derivative represented by General Formula (G0) can be obtained.

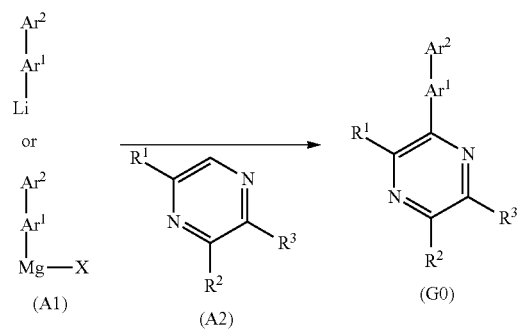

(a)

Alternatively, as illustrated in Scheme (a') below, arylboronic acid (A1') is reacted with a halogenated pyrazine compound (A2'), so that the arylpyrazine derivative represented by General Formula (G0) can be obtained.

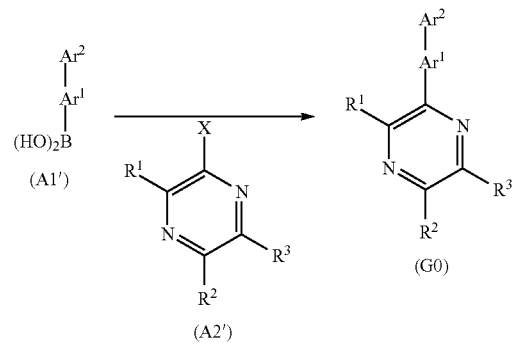

(a')

Further alternatively, as illustrated in Scheme (a") below, aryl diketone (A1') is reacted with diamine (A2"), so that the arylpyrazine derivative represented by General Formula (G0) can be obtained.

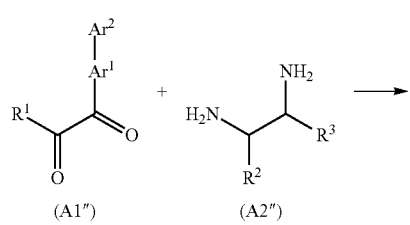

(a")

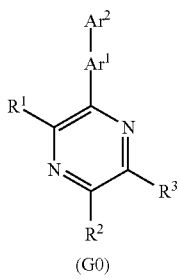

(G0)

Since the above-described compounds (A1), (A2), (A1'), (A2'), (A1"), and (A2") are commercially available as a wide variety of compounds or their synthesis is feasible, a great variety of arylpyrazine derivatives can be synthesized as the arylpyrazine derivative represented by General Formula (G0). Thus, there is abundant variation in ligands, which is a feature of an organometallic complex which is one embodiment of the present invention.

Method of Synthesizing Organometallic Complexes of Embodiments of the Invention Represented by General Formulae (G3) and (G5)

Next, description is made of the organometallic complexes, each of which is one embodiment of the present invention and formed by ortho-metalation of the arylpyrazine derivative represented by General Formula (G0), i.e. the organometallic complexes represented by General Formulae (G3) and (G5) below, which are preferred specific examples of the organometallic complex including the structure represented by General Formula (G1) below.

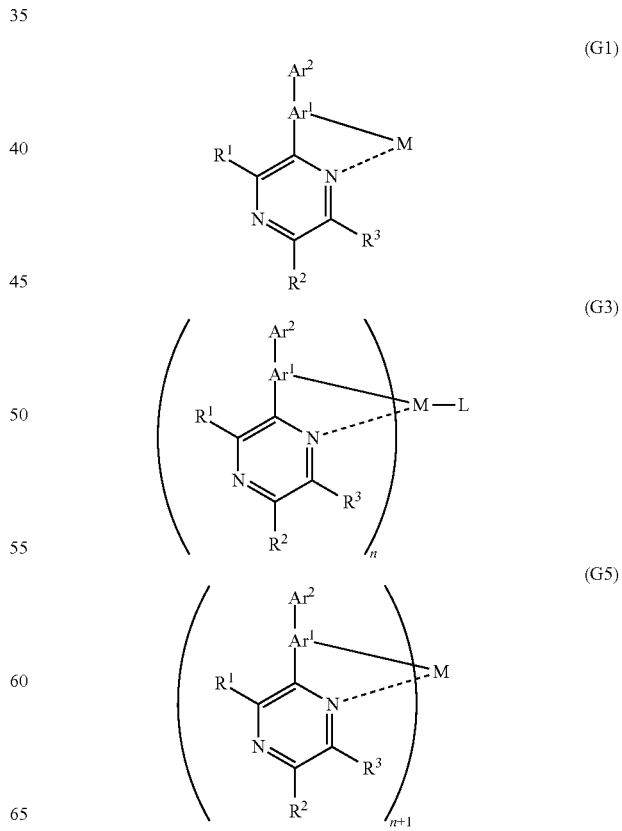

In each of General Formulae (G1), (G3), and (G5), $R^1$ represents any of an alkyl group having 1 to 4 carbon atoms, an alkoxy group having 1 to 4 carbon atoms, and an alkylthio group having 1 to 4 carbon atoms. Further, $R^2$ represents any of hydrogen, an alkyl group having 1 to 4 carbon atoms, an alkoxy group having 1 to 4 carbon atoms, and an alkylthio group having 1 to 4 carbon atoms. Furthermore, $R^3$ represents hydrogen or an alkyl group having 1 to 4 carbon atoms. One of $Ar^1$ and $Ar^2$ represents a condensed aromatic hydrocarbon group having 10 to 13 carbon atoms, and the other represents an aromatic hydrocarbon group having 6 to 13 carbon atoms. In addition, $Ar^1$ and $Ar^2$ may separately have a substituent. Further, M is a central metal and represents a Group 9 element or a Group 10 element. In General Formula (G3), L represents a monoanionic ligand. Moreover, n is 2 when the central metal is a Group 9 element or n is 1 when the central metal is a Group 10 element.

First, as illustrated in Synthesis Scheme (b) below, the arylpyrazine derivative represented by General Formula (G0) and a compound of a Group 9 metal or of a Group 10 metal which contains a halogen (a metal halide or a metal complex) are heated in an alcohol-based solvent (glycerol, ethylene glycol, 2-methoxyethanol, or 2-ethoxyethanol) alone or a mixed solvent of water and one or more kinds of such alcohol-based solvents, whereby a binuclear complex (B) can be obtained, which is a kind of organometallic complex including the structure represented by General Formula (G1).

Examples of the compound of a Group 9 metal or of a Group 10 metal which contains a halogen are, but not limited to, rhodium chloride hydrate, palladium chloride, iridium chloride hydrate, iridium chloride hydrochloride hydrate, potassium tetrachloroplatinate(II), and the like. Note that in Synthesis Scheme (b) below, M represents a Group 9 element or a Group 10 element, and X represents a halogen element. In addition, n is 2 when M is a Group 9 element or n is 1 when M is a Group 10 element.

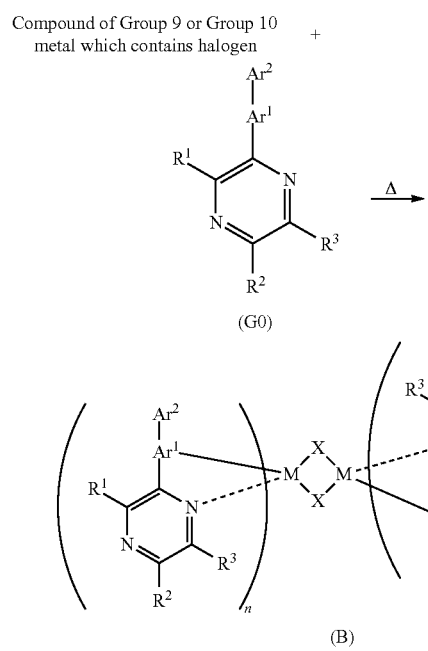

(b)

Scheme (b) is reacted with HL which is a material of a monoanionic ligand, whereby a proton of HL is separated and L is coordinated to the central metal M. Thus, the organometallic complex represented by General Formula (G3) which is one embodiment of the present invention can be obtained. Note that in Synthesis Scheme (c), M represents a Group 9 element or a Group 10 element, and X represents a halogen element. In addition, n is 2 when M is a Group 9 element or n is 1 when M is a Group 10 element.

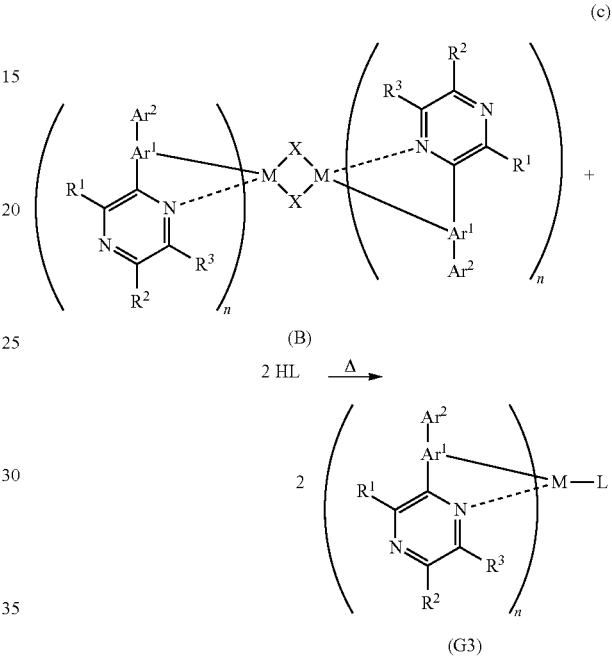

(c)

Note that decomposition reaction of the material complex in Scheme (c) can be suppressed when $R^1$ and $R^2$ in General Formula (G3) is not hydrogen but any of the substituents of an alkyl group having 1 to 4 carbon atoms, an alkoxy group having 1 to 4 carbon atoms, an alkylthio group having 1 to 4 carbon atoms, and an alkoxycarbonyl group having 1 to 5 carbon atoms, which leads to an improved yield.

The monoanionic ligand (L) in General Formula (G3) is any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which each of two ligands is nitrogen.

Further, the monoanionic ligand (L) in General Formula (G3) is represented by any of the following General Formulae (L1) to (L6).

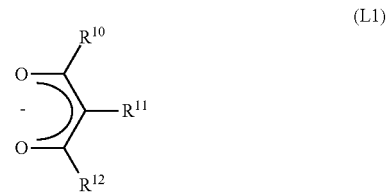

(L1)

Furthermore, as illustrated in Synthesis Scheme (c) below, the dinuclear complex (B) obtained by the above Synthesis

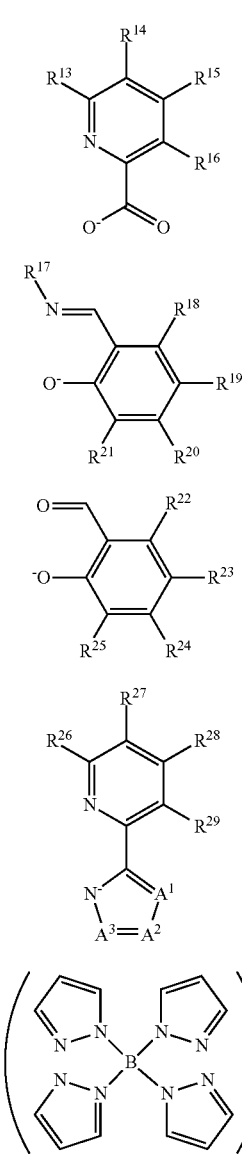

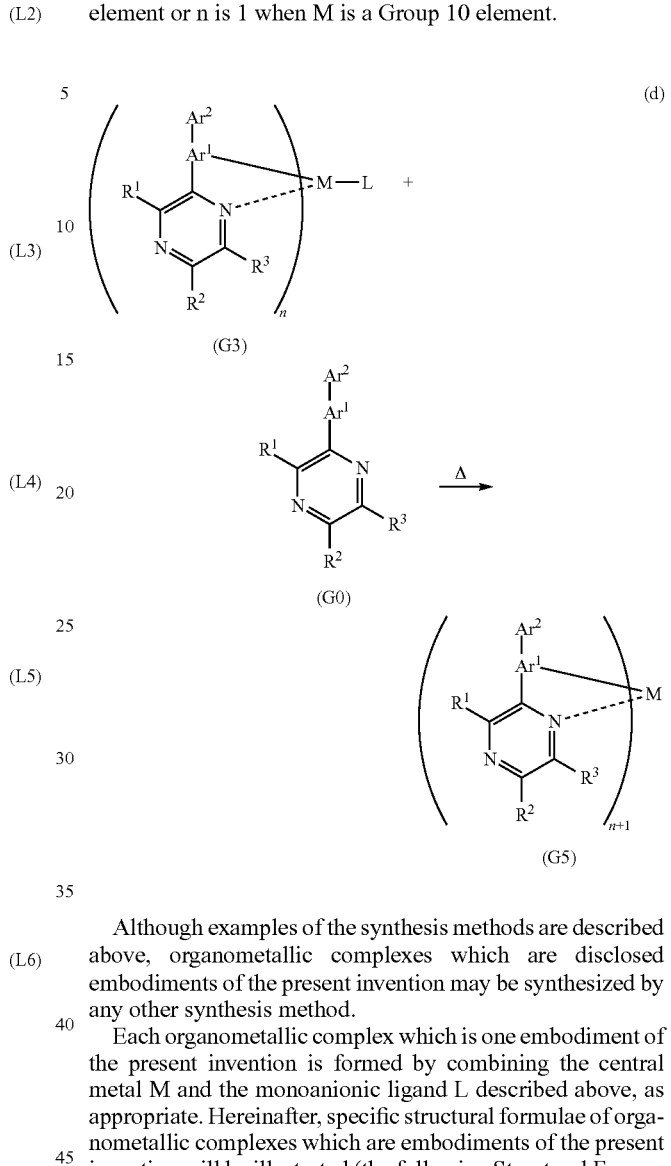

In General Formulae (L1) to (L6), $R^{10}$ to $R^{29}$ separately represent any of hydrogen, an alkyl group having 1 to 4 carbon atoms, a halogen, a haloalkyl group, an alkoxy group having 1 to 4 carbon atoms, and an alkylthio group having 1 to 4 carbon atoms. Further, $A^1$ to $A^3$ separately represent nitrogen, $sp^2$ hybridized carbon bonded to hydrogen, or $sp^2$ carbon bonded to a substituent R. Note that the substituent R represents any of an alkyl group having 1 to 4 carbon atoms, a haloalkyl group having 1 to 4 carbon atoms, and a phenyl group.

The organometallic complex represented by the above General Formula (G5), which is one embodiment of the present invention, can be synthesized according to Synthesis Scheme (d) below, and specifically in such a manner that the organometallic complex represented by General Formula (G3), which is obtained by the above Synthesis Scheme (c), and the arylpyrazine derivative represented by General Formula (G0) are heated in a high boiling solvent such as glycerin at a high temperature of about 200° C. Note that, in Synthesis Scheme (d), M represents a Group 9 element or a Group 10 element. In addition, n is 2 when M is a Group 9 element or n is 1 when M is a Group 10 element.

Although examples of the synthesis methods are described above, organometallic complexes which are disclosed embodiments of the present invention may be synthesized by any other synthesis method.

Each organometallic complex which is one embodiment of the present invention is formed by combining the central metal M and the monoanionic ligand L described above, as appropriate. Hereinafter, specific structural formulae of organometallic complexes which are embodiments of the present invention will be illustrated (the following Structural Formulae (100) to (147)); however, the present invention is not limited thereto.

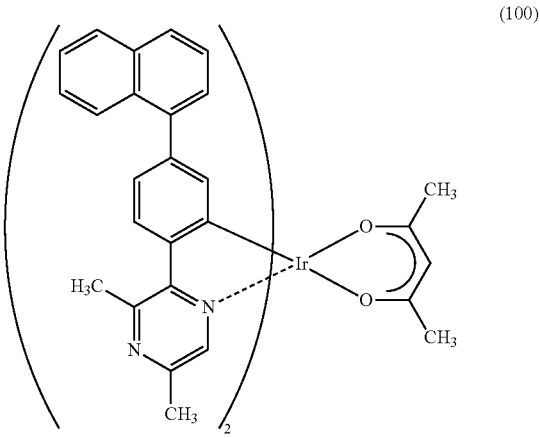

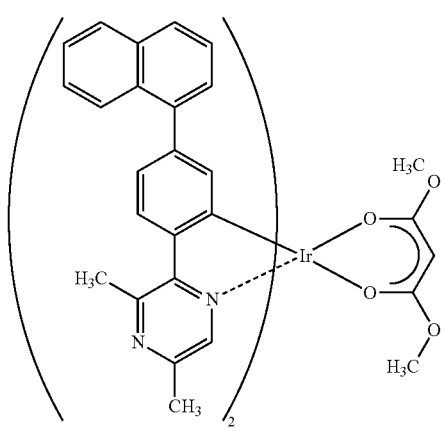
(101)
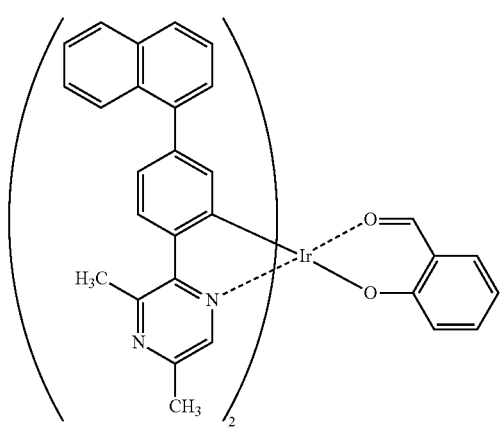
(104)
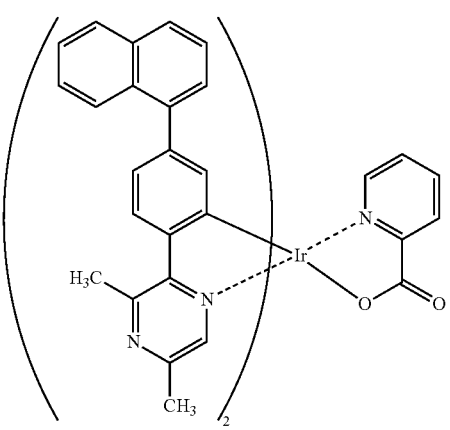
(102)
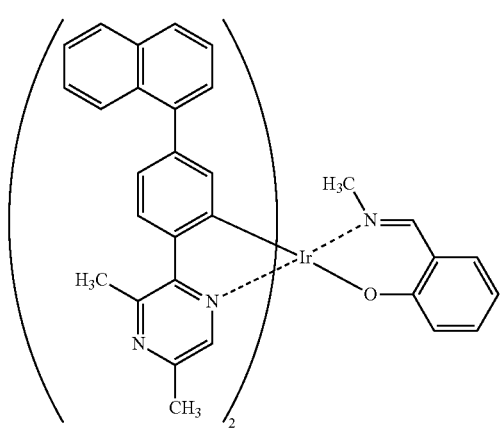
(105)
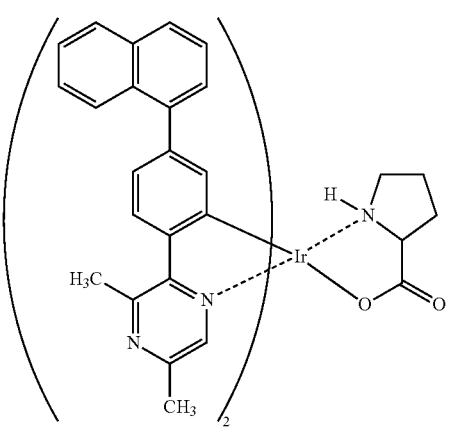
(103)
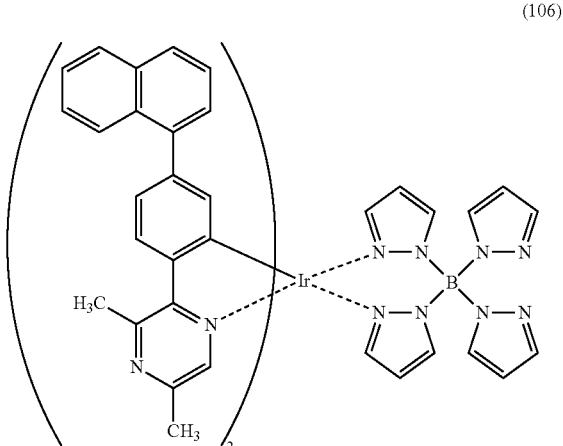
(106)

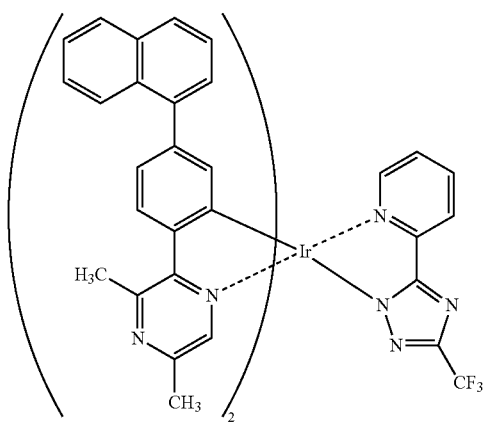
(107)
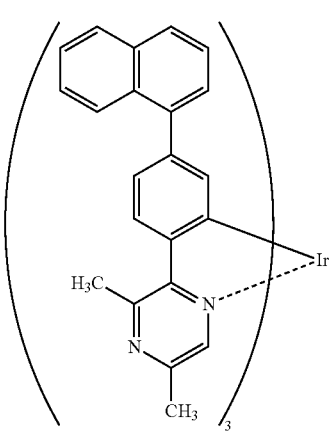
(108)
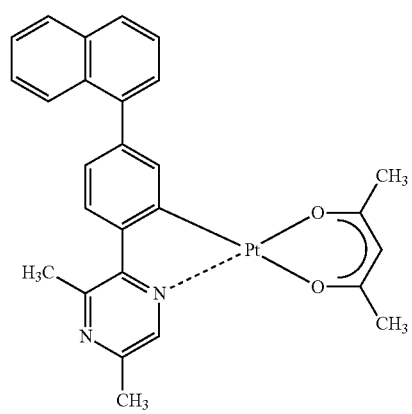
(109)
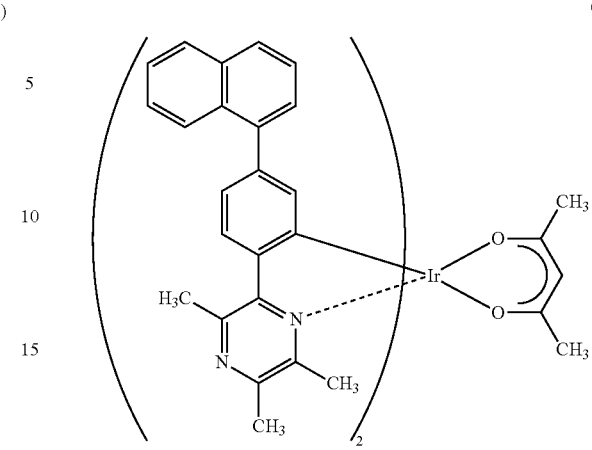
(110)
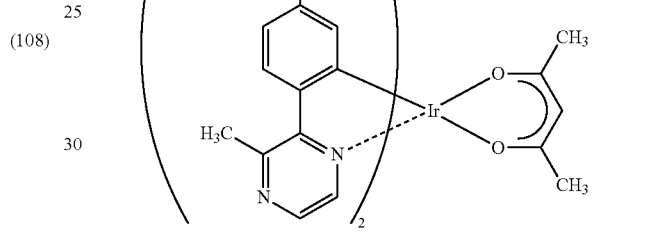
(111)
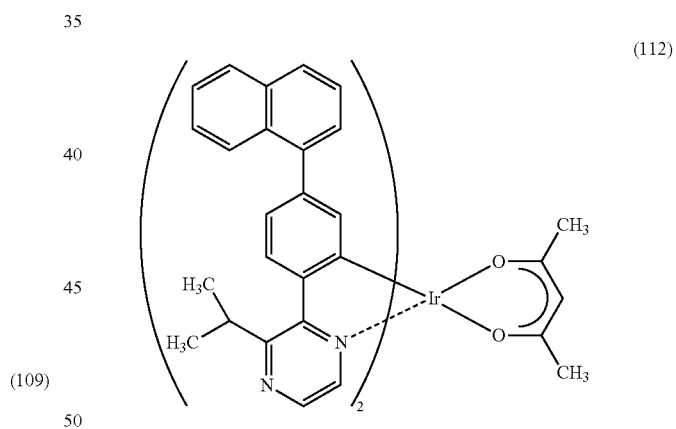
(112)
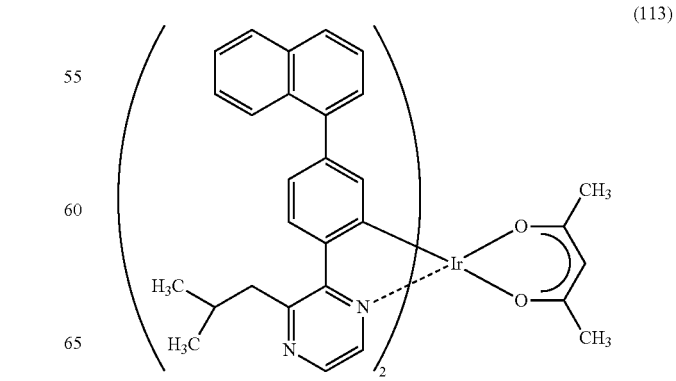
(113)

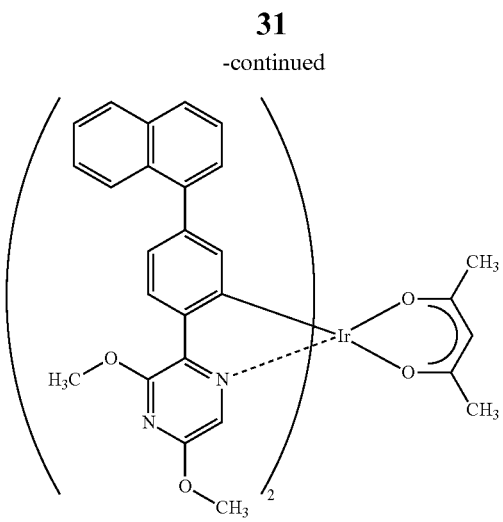
(114)
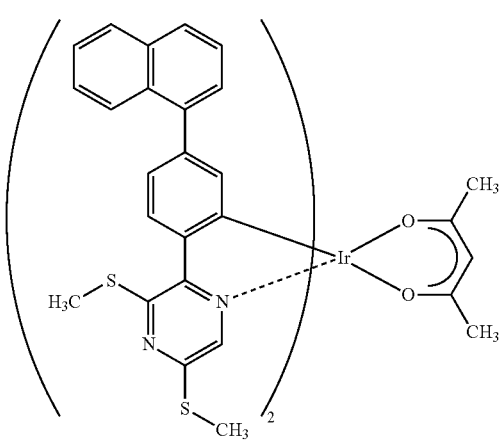
(115)
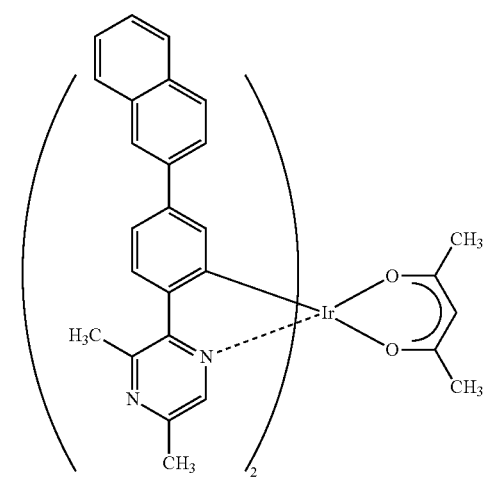
(116)
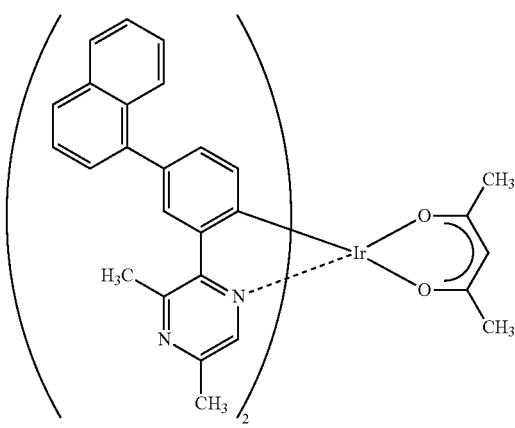
(117)
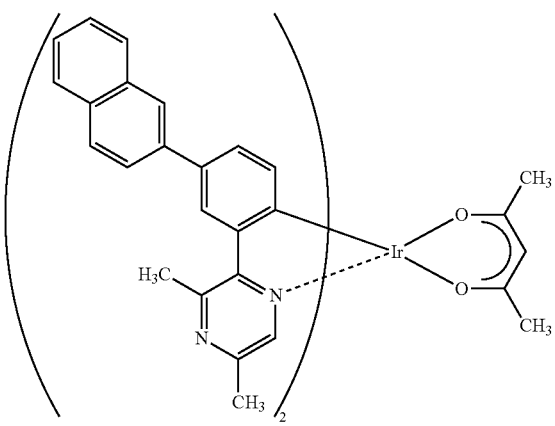
(118)
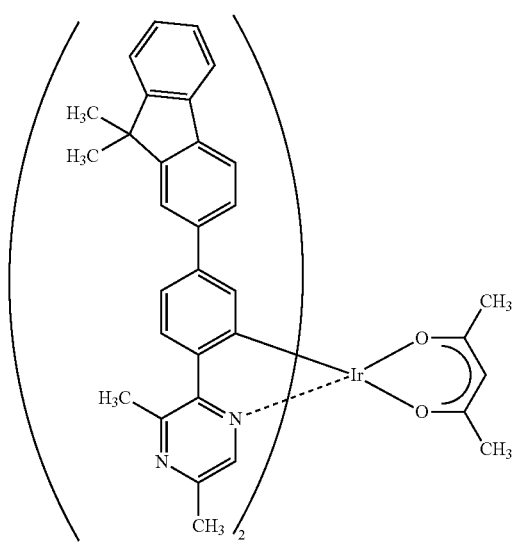
(119)

(120)
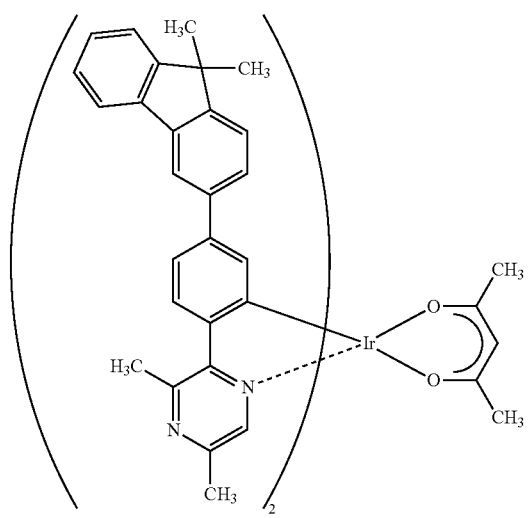
(121)
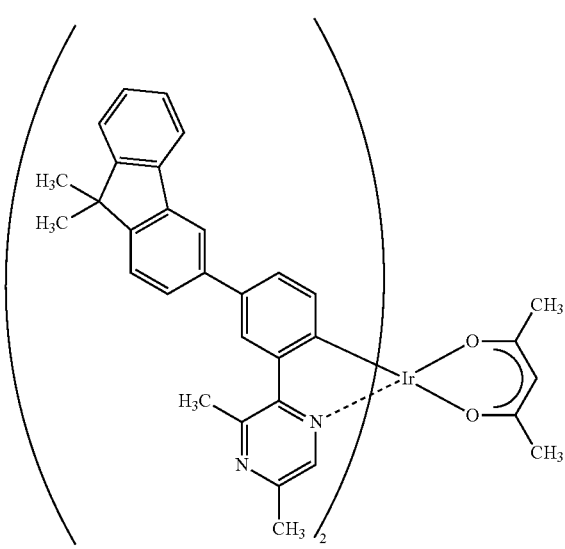
(122)
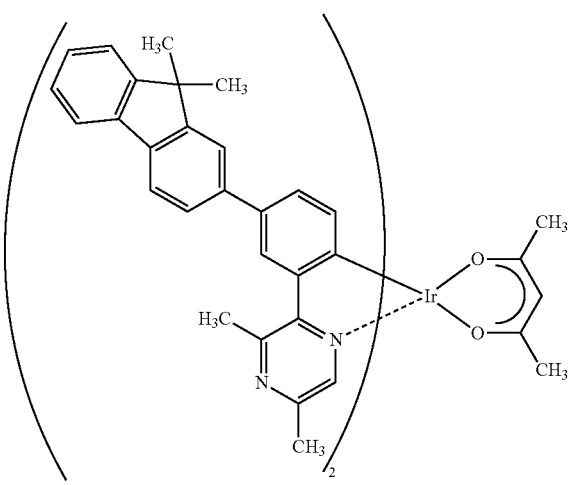
(123)
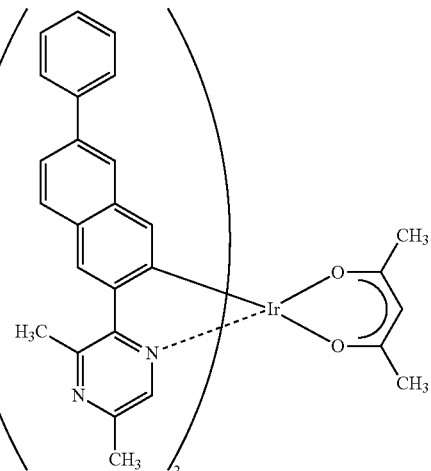
(124)
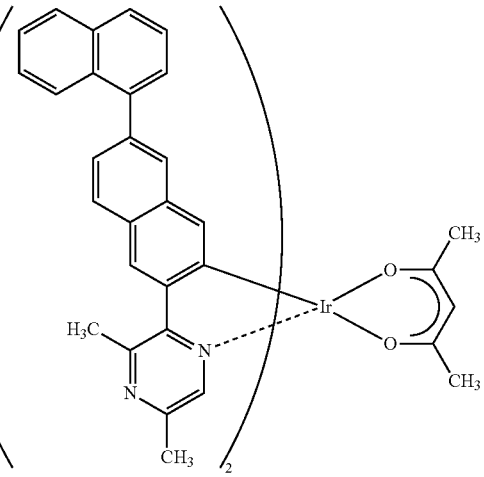
(125)
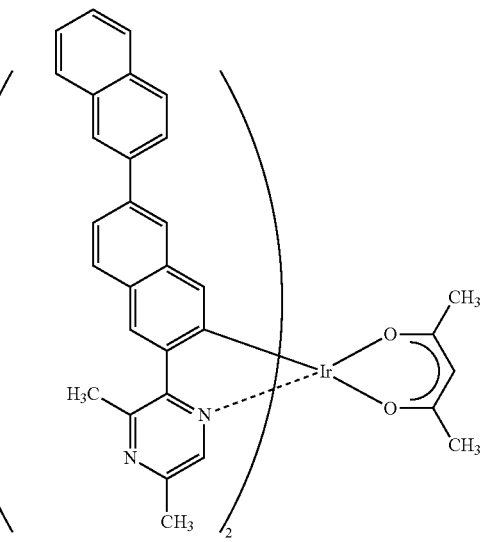

-continued
(126)
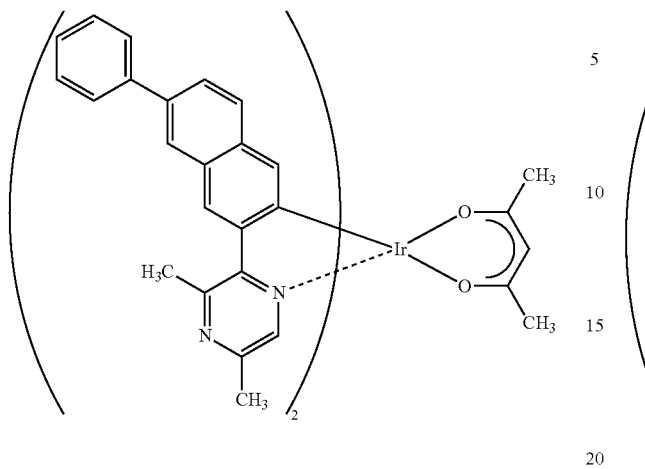
(127)
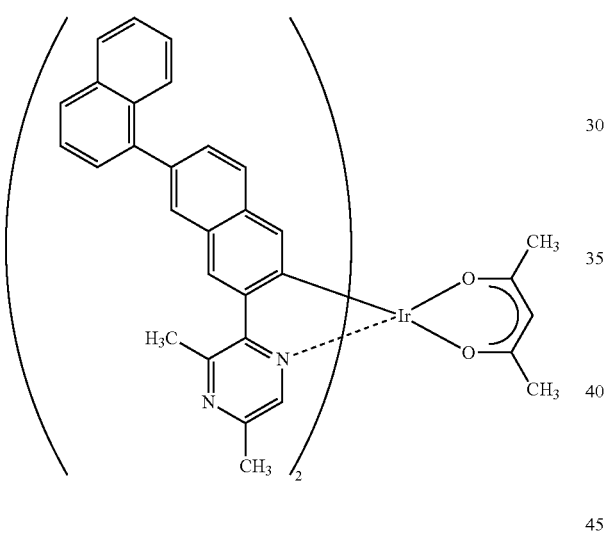
(128)
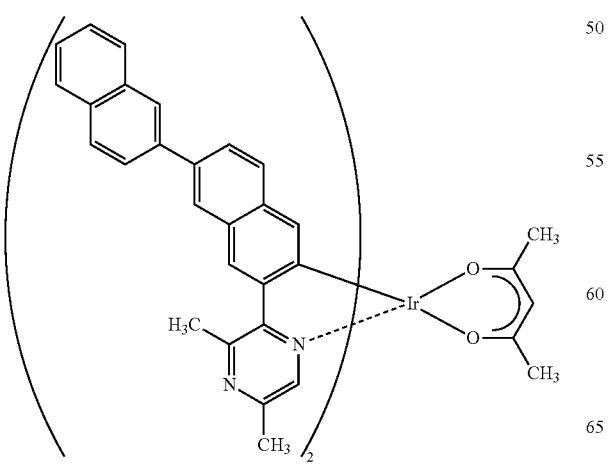
(129)
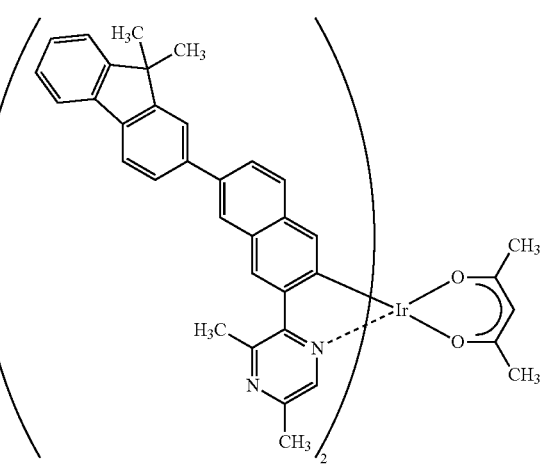
(130)
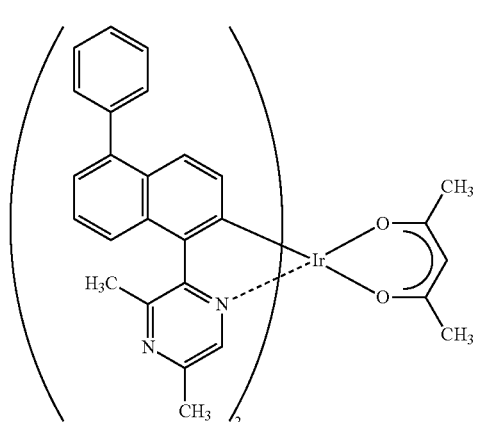
(131)
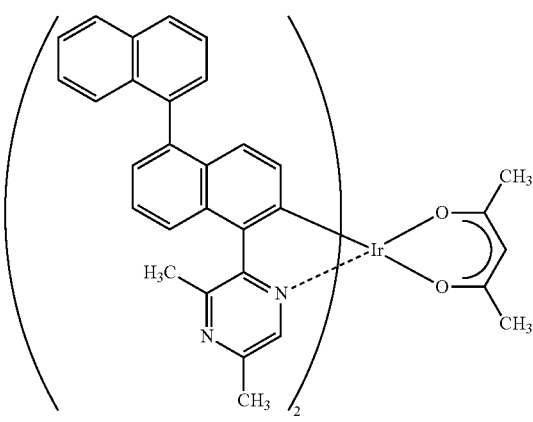

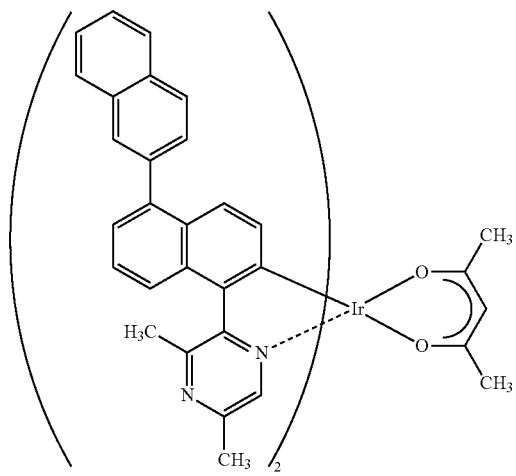
(132)
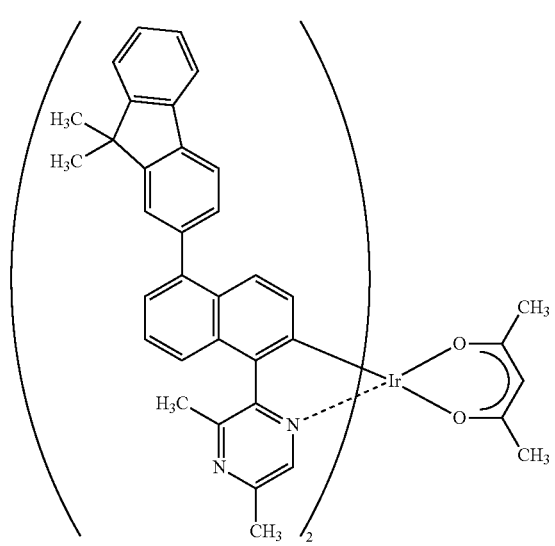
(133)
(134)
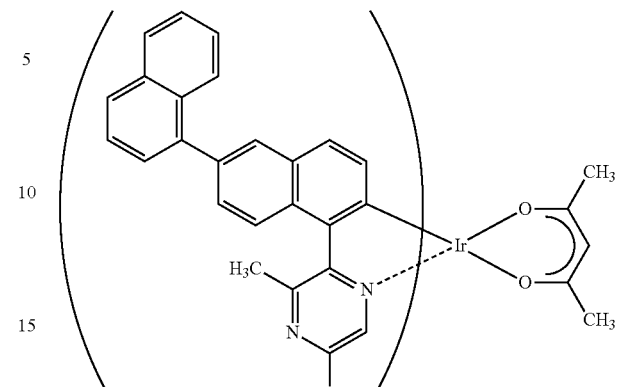
(135)
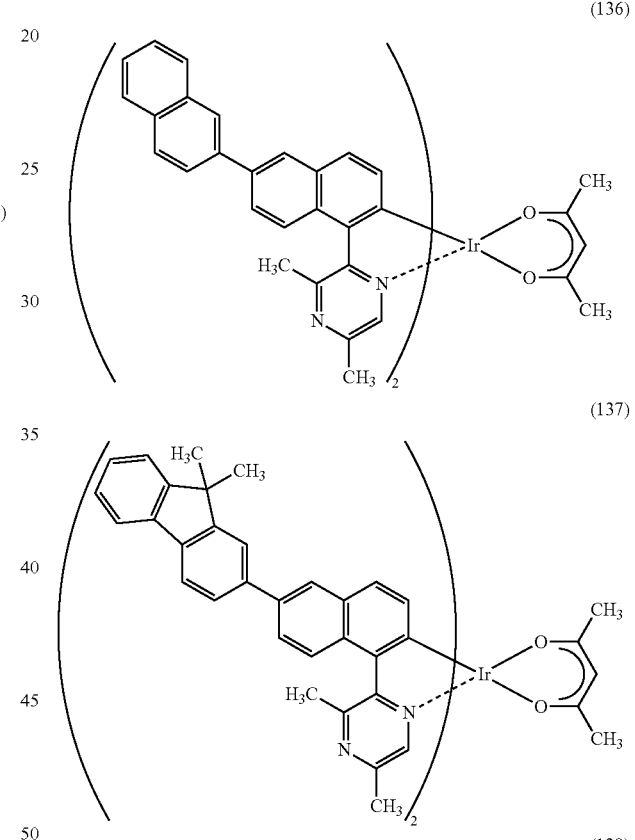
(136)
(137)
(138)

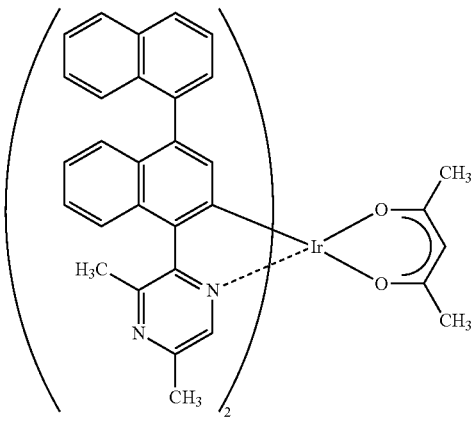
(139)
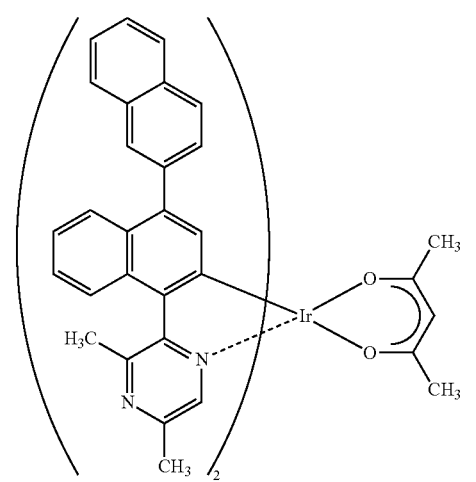
(140)
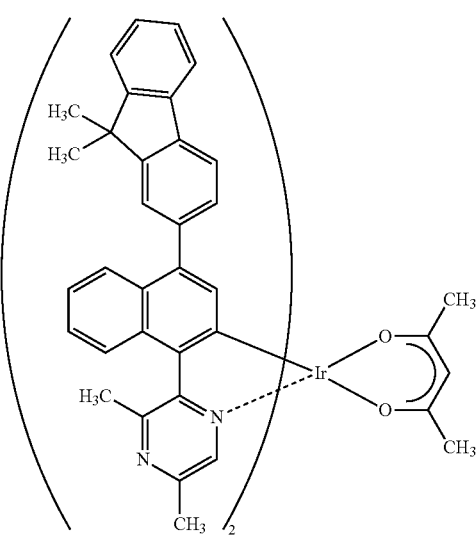
(141)
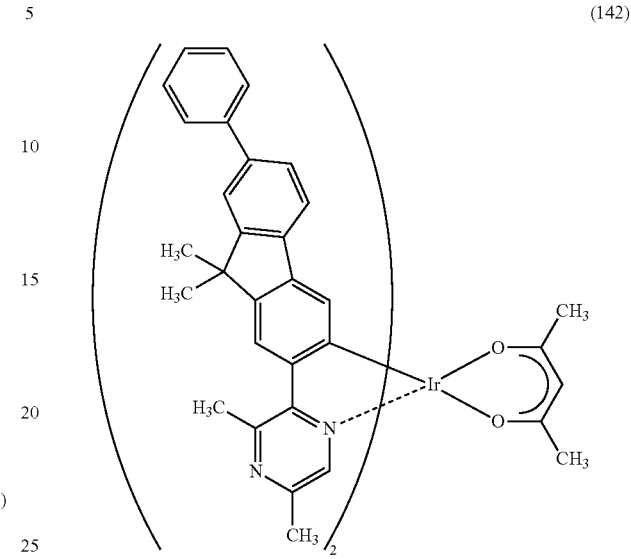
(142)
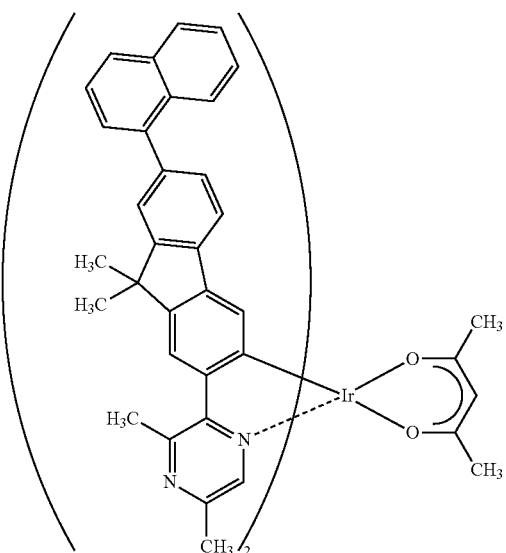
(143)

(144)

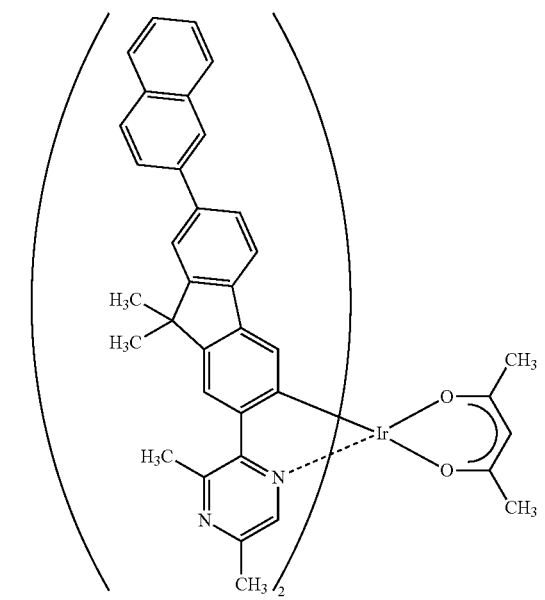

(145)

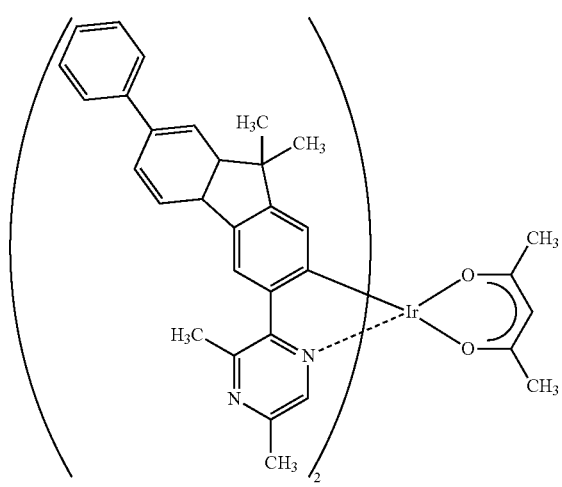

(146)

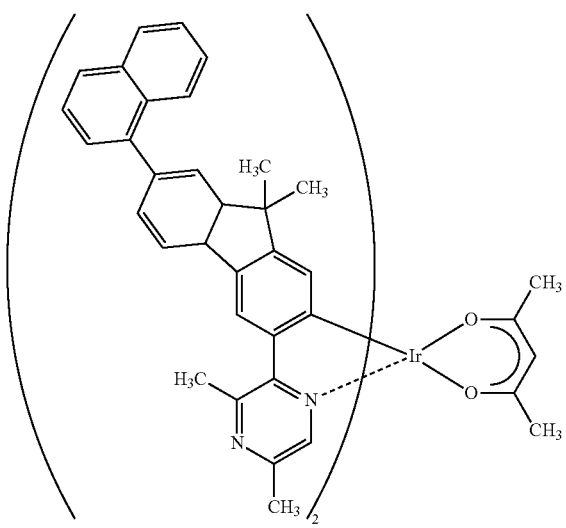

(147)

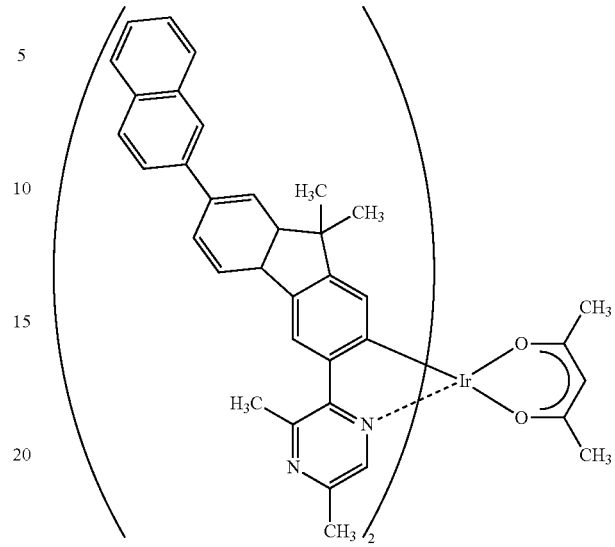

Depending on the type of the ligand, there can be stereoisomers of the organometallic complexes represented by the above Structural Formulae (100) to (147), and such isomers are included in the category of organometallic complexes which are embodiments of the present invention.

Since the above organometallic complexes which are embodiments of the present invention are capable of intersystem crossing, they can each be used as a photosensitizer. Furthermore, since the organometallic complexes are capable of emitting phosphorescence, they can each be used as a light-emitting material or a light-emitting substance for a light-emitting element.

Embodiment 2

In Embodiment 2, as one embodiment of the present invention, a light-emitting element in which an organometallic complex is used for a light-emitting layer will be described with reference to FIG. 1.

FIG. 1 illustrates a light-emitting element in which an EL layer 102 including a light-emitting layer 113 is interposed between a first electrode 101 and a second electrode 103. The light-emitting layer 113 includes an organometallic complex which is one embodiment of the present invention as described in Embodiment 1.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. Thus, the organometallic complex which is one embodiment of the present invention functions as a light-emitting substance in the light-emitting element. Note that in the light-emitting element described in this embodiment, the first electrode 101 functions as an anode and the second electrode 103 functions as a cathode.

When the first electrode 101 functions as an anode, any of metals, alloys, electrically conductive compounds, mixtures thereof, and the like which has a high work function (specifically, a work function of 4.0 eV or more) is preferably used for the first electrode 101. Specific examples include indium oxide-tin oxide (ITO: indium tin oxide), indium tin oxide containing silicon or silicon oxide, indium oxide-zinc oxide (IZO: indium zinc oxide), indium oxide containing tungsten oxide and zinc oxide, and the like. Other examples of the substance that can be used are gold (Au), platinum (Pt), nickel (Ni), tungsten (W), chromium (Cr), molybdenum (Mo), iron (Fe), cobalt (Co), copper (Cu), palladium (Pd), titanium (Ti), and the like.

When a layer included in the EL layer 102 which is formed in contact with the first electrode 101 is formed using a later described composite material in which an organic compound and an electron acceptor (acceptor) are mixed, the first electrode 101 can be formed using any of various types of metals, alloys, and electrically-conductive compounds, a mixture thereof, and the like regardless of the work function. For example, aluminum (Al), silver (Ag), an alloy containing aluminum (e.g., Al—Si), or the like can be used.

Note that the first electrode 101 can be formed by, for example, a sputtering method, an evaporation method (including a vacuum evaporation method), or the like.

The EL layer 102 formed over the first electrode 101 has at least the light-emitting layer 113 and includes an organometallic complex which is one embodiment of the present invention. The EL layer 102 can also include a known substance as a part, which can be either a low molecular compound or a high molecular compound. Note that substances forming the EL layer 102 may consist of organic compounds or may include an inorganic compound as a part.

As illustrated in FIG. 1, the EL layer 102 is found by stacking, in addition to the light-emitting layer 113, a hole-injection layer 111 containing a substance having a high hole-injection property, a hole-transport layer 112 containing a substance having a high hole-transport property, an electron-transport layer 114 containing a substance having a high electron-transport property, an electron-injection layer 115 containing a substance having a high electron-injection property, and the like, as appropriate.

The hole-injection layer 111 is a layer containing a substance having a high hole-injection property. Examples of applicable substances having a high hole-injection property are metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Other examples of applicable substances are phthalocyanine-based compounds such as phthalocyanine (abbreviation: $H_2Pc$) and copper(II) phthalocyanine (abbreviation: CuPc).

Other examples of applicable substances are aromatic amine compounds which are low molecular organic compounds such as 4,4',4"-tris(N,N-diphenylamino)triphenylamine (abbreviation: TDATA), 4,4',4"-tris[N-3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of applicable substances are high molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl) benzidine] (abbreviation: Poly-TPD), and high molecular compounds to which acid is added, such as poly(3,4-ethylenedioxythiophene)/poly(styrenesulfonic acid) (PEDOT/PSS), or polyaniline/poly(styrenesulfonic acid) (PAni/PSS).

For the hole-injection layer 111, the composite material in which an organic compound and an electron acceptor (acceptor) are mixed may be used. Such a composite material, in which holes are generated in the organic compound by the electron acceptor, has excellent hole injection and transport properties. The organic compound here is preferably a material excellent in transporting the generated holes (a substance having a high hole-transport property).

Examples of the organic compound used for the composite material are a variety of compounds such as aromatic amine compounds, carbazole derivatives, aromatic hydrocarbons, and high molecular compounds (e.g., oligomers, dendrimers, and polymers), and preferably organic compounds having a high hole-transport property, and specifically preferably substances having a hole mobility of $10^{-6}$ cm$^2$/Vs or more. Note that other than these substances, any substance that has a property of transporting more holes than electrons may be used. The organic compounds which can be used for the composite material will be specifically described below.

Examples of the organic compound that can be used for the composite material are aromatic amine compounds such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), 9-phenyl-3-[4-(10-phenyl-9-anthryl)phenyl]-9H-carbazole (abbreviation: PCzPA), and 1,4-bis[4-(N-carbazoyl)phenyl]-2,3,5,6-tetraphenylbenzene.

Other examples of the organic compound that can be used are aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl] anthracene, and 2,3,6,7-tetramethyl-9,10-di (1-naphthyl)anthracene.

Other examples of the organic compound that can be used are aromatic hydrocarbon compounds such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis [4-(2,2-diphenylvinyl)phenyl]anthracene (abbreviation: DPVPA).

Further, examples of the electron acceptor are organic compounds such as 7,7,8,8-tetracyano-2,3,5,6-tetrafluoroquinodimethane (abbreviation: $F_4$-TCNQ) and chloranil, transition metal oxides, and oxides of metals that belong to Groups 4 to 8 in the periodic table. Specific preferred examples include vanadium oxide, niobium oxide, tantalum oxide, chromium oxide, molybdenum oxide, tungsten oxide, manganese oxide, and rhenium oxide because of their high electron-acceptor properties. Among these, molybdenum oxide is especially preferable since it is stable in the air and its hygroscopic property is low and is easily treated.

The composite material may be formed using the above-described electron acceptor and the above-described high molecular compound such as PVK, PVTPA, PTPDMA, or Poly-TPD and used for the hole-injection layer 111.

The hole-transport layer 112 is a layer that contains a substance having a high hole-transport property. Examples of the substance having a high hole-transport property are aromatic amine compounds such as NPB, TPD, BPAFLP, 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino] biphenyl (abbreviation: BSPB). The substances mentioned here are mainly substances that have a hole mobility of $10^{-6}$ $cm^2/Vs$ or more. Note that other than the above substances, any substance that has a property of transporting more holes than electrons may be used. Further, the layer including a substance having a high hole-transport property is not limited to a single layer, and may be a stack of two or more layers containing any of the above substances.

For the hole-transport layer 112, a carbazole derivative such as CBP, CzPA, or PCzPA or an anthracene derivative such as t-BuDNA, DNA, or DPAnth may be used.

For the hole-transport layer 112, a high molecular compound such as PVK, PVTPA, PTPDMA, or Poly-TPD can be used.

The light-emitting layer 113 is a layer containing an organometallic complex which is one embodiment of the present invention, and preferably a layer where the organometallic complex which is one embodiment of the present invention is dispersed as a guest in a substance as a host which has higher triplet excitation energy than the organometallic complex which is one embodiment of the present invention. Thus, quenching of light emitted from the organometallic complex caused depending on the concentration can be prevented. Note that the triplet excited energy indicates an energy gap between a ground state and a triplet excited state.

The substance (i.e. host) used for dispersing any of the above-described organometallic complexes is preferably, but not limited to, any of compounds having an arylamine skeleton, such as 2,3-bis(4-diphenylaminophenyl)quinoxaline (abbreviation: TPAQn) and NPB, carbazole derivatives such as CBP and 4,4',4"-tris(N-carbazolyl)triphenylamine (abbreviation: TCTA), and metal complexes such as bis[2-(2-hydroxyphenyl)pyridinato] zinc (abbreviation: $Znpp_2$), bis[2-(2-hydroxyphenyl)benzoxazolato] zinc (abbreviation: $Zn(BOX)_2$), bis(2-methyl-8-quinolinolato)(4-phenylphenolato)aluminum (abbreviation: BAlq), and tris(8-quinolinolato)aluminum (abbreviation: $Alq_3$). Alternatively, a high molecular compound such as PVK can be used.

The electron-transport layer 114 is a layer containing a substance having a high electron-transport property. Examples of the substance for the electron-transport layer 114 are metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, and bis[2-(2-hydroxyphenyl)benzothiazolato] zinc (abbreviation: $Zn(BTZ)_2$). Other examples of the substance that can be used are heteroaromatic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl) stilbene (abbreviation: BzOs), and high molecular compounds such as poly(2,5-pyridinediyl) (abbreviation: PPy), poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy). The substances described here are mainly substances having an electron mobility of $10^{-6}$ $cm^2/Vs$ or more. Note that other than the above substances, any substance that has a property of transporting more electrons than holes may be used for the electron-transport layer.

Further, the electron-transport layer is not limited to a single layer, and may be a stack of two or more layers containing any of the above substances.

The electron-injection layer 115 is a layer that contains a substance having a high electron-injection property. Examples of the substance that can be used for the electron-injection layer 115 are alkali metals, alkaline earth-metals, and compounds thereof, such as lithium (Li), cesium (Cs), calcium (Ca), lithium fluoride (LiF), cesium fluoride (CsF), calcium fluoride ($CaF_2$), and lithium oxide (LiOx), rare earth-metal compounds such as erbium fluoride ($ErF_3$), and the above-mentioned substances for forming the electron-transport layer 114.

Alternatively, a composite material in which an organic compound and an electron donor (donor) are mixed may be used for the electron-injection layer 115. Such a composite material, in which electrons are generated in the organic compound by the electron donor, has excellent electron injection and transport properties. The organic compound here is preferably a material excellent in transporting the generated electrons, as which specifically any of the above substances (such as metal complexes and heteroaromatic compounds) for the electron-transport layer 114 can be used. The electron donor can be a substance exhibiting an electron-donating property for the organic compound. Specific examples of the electron donor are alkali metals, alkaline-earth-metals, and rare earth-metals, such as lithium, cesium, magnesium, calcium, erbium, and ytterbium. Any of alkali metal oxides and alkaline-earth-metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, and the electron-injection layer 115 which are described above can each be formed by a method such as an evaporation method (e.g., a vacuum evaporation method), an inkjet method, or a coating method.

When the second electrode 103 functions as a cathode, any of metals, alloys, electrically conductive compounds, mixtures thereof, and the like which has a low work function (specifically, a work function of 3.8 eV or less) is preferably used for the second electrode 103. Specific examples of the substance that can be used are elements that belong to Groups 1 and 2 in the periodic table, that is, alkali metals such as lithium (Li) and cesium (Cs), alkaline earth-metals such as magnesium (Mg), calcium (Ca), and strontium (Sr), alloys thereof (e.g., Mg—Ag and Al—Li), rare earth-metals such as europium (Eu) and ytterbium (Yb), alloys thereof, aluminum (Al), silver (Ag), and the like.

When a layer included in the EL layer 102 which is formed in contact with the second electrode 103 is formed using the composite material in which the organic compound and the electron donor (donor), which are described above, are mixed, a variety of conductive materials such as Al, Ag, ITO, and indium tin oxide containing silicon or silicon oxide can be used regardless of the work function.

Note that the second electrode 103 can be formed by a vacuum evaporation method or a sputtering method. In the case of using a silver paste or the like, a coating method, an inkjet method, or the like can be used.

In the above-described light-emitting element, a current flows due to a potential difference generated between the first electrode 101 and the second electrode 103 and holes and electrons recombine in the EL layer 102, whereby light is emitted. Then, this emitted light is extracted outside through one or both of the first electrode 101 and the second electrode 103. Therefore, one or both of the first electrode 101 and the second electrode 103 are electrodes having a property of transmitting visible light.

By use of the light-emitting element described in this embodiment, a passive matrix light-emitting device or an active matrix light-emitting device in which driving of the light-emitting element is controlled by a thin film transistor (TFT) can be manufactured.

In the case where an active matrix light-emitting device is manufactured, there is no particular limitation on the structure of the TFT: for example, a staggered TFT or an inverted staggered TFT can be used as appropriate; and a driver circuit formed over a TFT substrate may be formed with an n-type TFT and a p-type TFT, or with either an n-type TFT or a p-type TFT. In addition, there is no particular limitation on the crystallinity of a semiconductor film used for the TFT, and any of the following can be used: amorphous semiconductor films, crystalline semiconductor films, oxide semiconductor films, and the like.

Note that, in this embodiment, the organometallic complex of one embodiment of the present invention, which is used for the light-emitting layer 113, emits red light with high color purity. Thus, a light-emitting element that emits red light with high color purity can be obtained.

Note that in this embodiment, any of the structures described in Embodiment 1 can be used in appropriate combination.

Embodiment 3

The light-emitting element which is one embodiment of the present invention may have a plurality of light-emitting layers. A plurality of light-emitting layers is provided so that each light-emitting layer emits light, whereby a mixture of the light can be obtained. Thus, for example, emission of white light can be obtained. In Embodiment 3, a mode of a light-emitting element having a plurality of light-emitting layers will be described with reference to FIG. 2.

Figure 2:
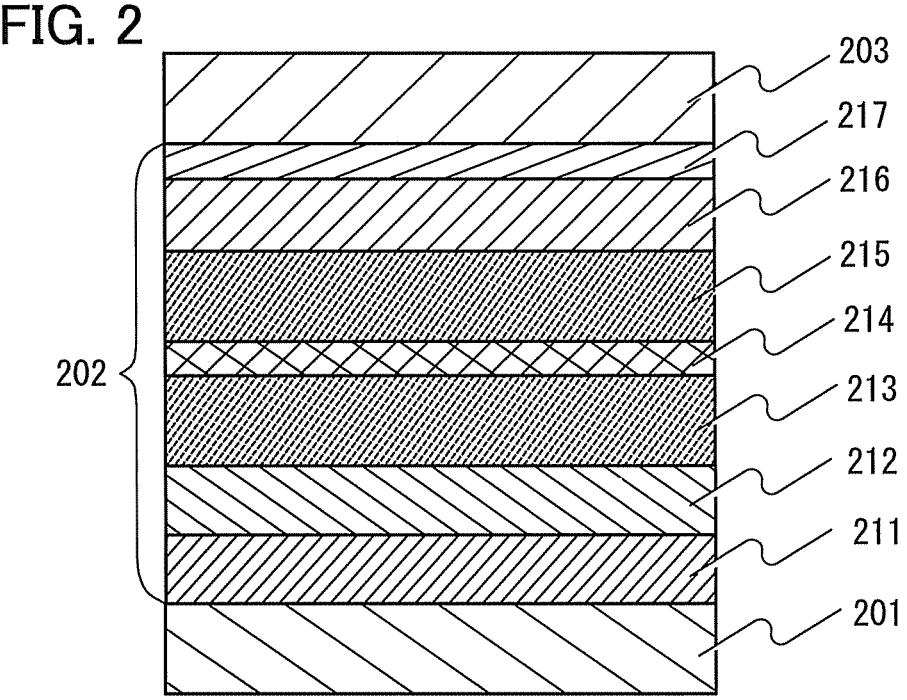
FIG. 2 illustrates a light-emitting element which is one embodiment of the present invention.

In FIG. 2, a first light-emitting layer 213 and a second light-emitting layer 215 are provided in an EL layer 202 between a first electrode 201 and a second electrode 203, so that emission of light that is a mixture of light emitted from the first light-emitting layer 213 and light emitted from the second light-emitting layer 215 can be obtained. A separation layer 214 is preferably formed between the first light-emitting layer 213 and the second light-emitting layer 215.

When a voltage is applied so that the potential of the first electrode 201 is higher than the potential of the second electrode 203, a current flows between the first electrode 201 and the second electrode 203, and holes and electrons recombine in the first light-emitting layer 213, the second light-emitting layer 215, or the separation layer 214. Generated excitation energy is distributed to both the first light-emitting layer 213 and the second light-emitting layer 215 to raise each of a first light-emitting substance included in the first light-emitting layer 213 and a second light-emitting substance included in the second light-emitting layer 215 to an excited state. The first and second light-emitting substances each in the excited state emit light while returning to the ground state.

The first light-emitting layer 213 contains the first light-emitting substance, typical examples of which are fluorescent compounds such as perylene, 2,5,8,11-tetra(tert-butyl)perylene (abbreviation: TBP), DPVBi, 4,4'-bis[2-(N-ethylcarbazol-3-yl)vinyl]biphenyl (abbreviation: BCzVBi), BAlq, and bis(2-methyl-8-quinolinolato)galliumchloride (abbreviation: $Gamq_2Cl$), and phosphorescent compounds such as bis{2-[3,5-bis(trifluoromethyl)phenyl]pyridinato-N,$C^{2'}$}iridium(III)picolinate (abbreviation: $[Ir(CF_3\ ppy)_2(pic)]$), bis[2-(4,6-difluorophenyl)pyridinato-N,$C^{2'}$]iridium(III)acetylacetonate (abbreviation: FIr(acac)), bis[2-(4,6-difluorophenyl)pyridinato-N,$C^{2'}$]iridium(III)picolinate (abbreviation: FIrpic), and bis[2-(4,6-difuluorophenyl)pyridinato-N,$C^{2'}$]iridium(III)tetra(1-pyrazolyl)borate (abbreviation: FIr6), to emit light having an emission spectrum with a peak at 450 nm to 510 nm (i.e. blue light to blue green light).

In addition, when the first light-emitting substance is a fluorescent compound, the first light-emitting layer 213 preferably has a structure in which the first light-emitting substance is dispersed as a guest in a substance as a first host which has higher singlet excitation energy than the first light-emitting substance. When the first light-emitting substance is a phosphorescent compound, the first light-emitting layer 213 preferably has a structure in which the first light-emitting substance is dispersed as a guest in a substance as a first host which has higher triplet excitation energy than the first light-emitting substance. As the first host, DNA, t-BuDNA, or the like can be used other than NPB, CBP, TCTA, and the like described above. Note that the singlet excitation energy is an energy difference between a ground state and a singlet excited state.

The second light-emitting layer 215 includes an organometallic complex which is one embodiment of the present invention and emits red light. The second light-emitting layer 215 can have the same structure as the light-emitting layer 113 described in Embodiment 2.

Specifically, the separation layer 214 can be formed using TPAQn, NPB, CBP, TCTA, $Znpp_2$, ZnBOX or the like described above. By thus providing the separation layer 214, it is possible to prevent a defect in which only one of the first light-emitting layer 213 and the second light-emitting layer 215 has an excessively high emission intensity. Note that although not necessarily needed, the separation layer 214 may be provided as appropriate to adjust the ratio in emission intensity of the first light-emitting layer 213 to the second light-emitting layer 215.

Although the organometallic complex which is one embodiment of the present invention is used for the second light-emitting layer 215 and another light-emitting substance is used for the first light-emitting layer 213 in this embodiment, an organometallic complex which is one embodiment of the present invention may be used for the first light-emitting layer 213 and another light-emitting substance may be used for the second light-emitting layer 215.

Further, although the light-emitting element in which two light-emitting layers are provided as illustrated in FIG. 2 is described in this embodiment, the number of the light-emitting layers is not limited to two and may be three, for example, so that light emitted from each light-emitting layer is mixed. Thus, emission of white light, for example, can be obtained.

Note that the first electrode 201 can have the same structure as the first electrode 101 described in Embodiment 2. Similarly, the second electrode 203 can have the same structure as the second electrode 103 described in Embodiment 2.

In this embodiment, a hole-injection layer 211, a hole-transport layer 212, an electron-transport layer 216, and an electron-injection layer 217 are provided as illustrated in FIG. 2. As for structures of these layers, the structures of the respective layers described in Embodiment 2 can be applied. However, these layers are not necessarily needed and may be provided as appropriate according to element characteristics.

Note that the structure described in this embodiment can be combined with any of the structures described in Embodiments 1 and 2 as appropriate.

Embodiment 4

Figure 3:
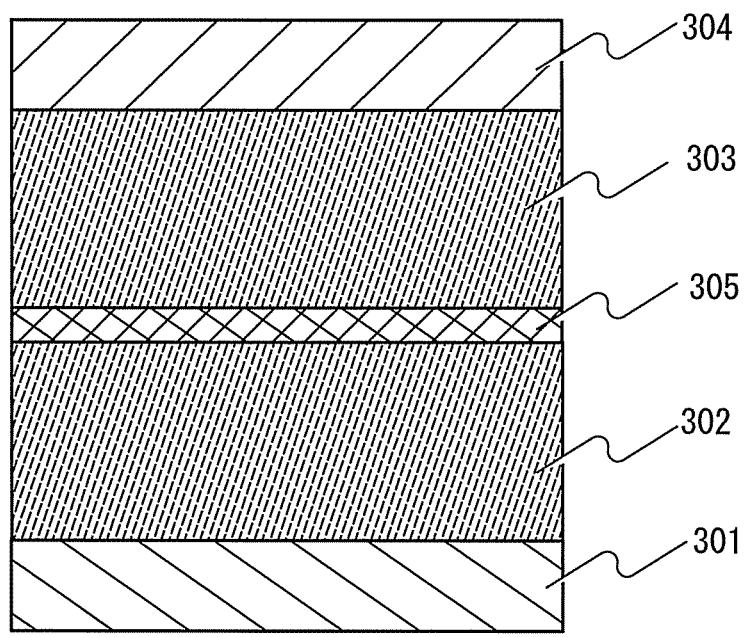
FIG. 3 illustrates a light-emitting element which is one embodiment of the present invention.

In Embodiment 4, as one embodiment of the present invention, a structure of a light-emitting element which includes a plurality of EL layers (hereinafter, referred to as a stacked-type element) will be described with reference to FIG. 3. This light-emitting element is a stacked-type light-emitting element having a plurality of EL layers (a first EL layer 302 and a second EL layer 303) between a first electrode 301 and a second electrode 304. Note that the number of the EL layers is two in this embodiment but may be three or more.

In this embodiment, the first electrode 301 functions as an anode, and the second electrode 304 functions as a cathode. Note that the first electrode 301 and the second electrode 304 can each have the same structures as in Embodiment 2. Further, all or any of the plurality of EL layers (the first EL layer 302 and the second EL layer 303) may have the same structure as the EL layer described in Embodiment 2. In other words, the structures of the first EL layer 302 and the second EL layer 303 may be the same as or different from each other and can be the same as in Embodiment 2.

Further, a charge generation layer 305 is provided between the plurality of EL layers (the first EL layer 302 and the second EL layer 303). The charge generation layer 305 has a function of injecting electrons into one of the EL layers and injecting holes into the other of the EL layers when a voltage is applied to the first electrode 301 and the second electrode 304. In the case of this embodiment, when a voltage is applied so that the potential of the first electrode 301 is higher than that of the second electrode 304, the charge generation layer 305 injects electrons into the first EL layer 302 and injects holes into the second EL layer 303.

Note that the charge generation layer 305 preferably has a property of transmitting visible light in terms of light extraction efficiency. Further, the charge generation layer 305 functions even if it has lower conductivity than the first electrode 301 or the second electrode 304.

The charge generation layer 305 may have a structure in which it includes the organic compound having a high hole-transport property and the electron acceptor (acceptor) or a structure in which it includes an organic compound having a high electron-transport property and the electron donor (donor), or may be a stack of both of these structures.

In the case of the structure in which the electron acceptor is added to the organic compound having a high hole-transport property, examples of the substance that can be used as the organic compound having a high hole-transport property are aromatic amine compounds such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ $cm^2/Vs$ or more. Note that other than the above substances, any substance that has a property of transporting more holes than electrons may be used.

Examples of the electron acceptor are 7,7,8,8-tetracyano-2,3,5,6-tetrafluoroquinodimethane (abbreviation: $F_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because of their high electron-acceptor properties. Among these, molybdenum oxide is especially preferable since it is stable in the air and its hygroscopic property is low and is easily treated.

In the case of the structure in which the electron donor is added to the organic compound having a high electron-transport property, examples of the organic compound having a high electron-transport property which can be used are: metal complexes having a quinoline skeleton or a benzoquinoline skeleton such as Alq, $Almq_3$, $BeBq_2$, and BAlq; metal complexes having an oxazole-based ligand or a thiazole-based ligand, such as $Zn(BOX)_2$ and $Zn(BTZ)_2$; and the like. Examples other than the metal complexes are PBD, OXD-7, TAZ, BPhen, BCP, and the like. The substances described here are mainly substances having an electron mobility of $10^{-6}$ $cm^2/Vs$ or more. Note that other than the above substances, any organic compound that has a property of transporting more electrons than holes may be used.

Examples of the electron donor that can be used are alkali metals, alkaline-earth metals, rare-earth metals, metals that belong to Group 13 in the periodic table and oxides or carbonates thereof, and preferably specifically lithium (Li), cesium (Cs), magnesium (Mg), calcium (Ca), ytterbium (Yb), indium (In), lithium oxide, cesium carbonate, and the like. An organic compound such as tetrathianaphthacene may be used as the electron donor.

By forming the charge generation layer 305 with any of the above materials, it is possible to suppress an increase in drive voltage caused when the EL layers are stacked.

Although the light-emitting element having two EL layers is described in this embodiment, the embodiment can be similarly applied to a light-emitting element in which three or more EL layers are stacked. When a plurality of EL layers with a charge generation layer interposed therebetween are arranged between a pair of electrodes, as in the light-emitting element of this embodiment, light emission in a high luminance region can be obtained. Thus, current density can be kept low, and an element having a long lifetime can be realized. Further, a voltage drop due to resistance of an electrode material can be reduced; accordingly, in application to lighting, uniform light emission in a large area can be obtained. Moreover, a light-emitting device which can be driven at low voltage with low power consumption can be achieved.

Furthermore, by making emission colors of the EL layers different, light having a desired color can be obtained from the light-emitting element as a whole. For example, the emission colors of first and second EL layers are complementary in a light-emitting element having the two EL layers, whereby the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors.

Further, the same can be applied to a light-emitting element having three EL layers. For example, the light-emitting element as a whole can emit white light when the emission color of the first EL layer is red, the emission color of the second EL layer is green, and the emission color of the third EL layer is blue.

Note that the structure described in this embodiment can be combined with any of the structures described in Embodiments 1 to 3 as appropriate.

Embodiment 5

In Embodiment 5, as one embodiment of the present invention, one mode of a light-emitting element in which an organometallic complex is used as a sensitizer will be described with reference to FIG. 1.

FIG. 1 illustrates the light-emitting element in which the EL layer 102 including the light-emitting layer 113 is interposed between the first electrode 101 and the second electrode 103. The light-emitting layer 113 includes an organometallic complex which is one embodiment of the present invention and a fluorescent compound that can emit light having a longer wavelength than light emitted from this organometallic complex.

In such a light-emitting element, holes injected from the first electrode 101 and electrons injected from the second electrode 103 side recombine in the light-emitting layer 113 to raise the fluorescent compound to an excited state. When the fluorescent compound in the excited state returns to the ground state, light is emitted. At this time, the organometallic complex which is one embodiment of the present invention acts as a sensitizer for the fluorescent compound, and increases the number of fluorescent compound molecules in a singlet excited state. With use of the organometallic complex of the present invention as a sensitizer in this manner, a light-emitting element having high emission efficiency can be obtained. Note that in the light-emitting element of this embodiment, the first electrode 101 functions as an anode and the second electrode 103 function as a cathode.

The light-emitting layer 113 includes the organometallic complex which is one embodiment of the present invention and the fluorescent compound that can emit light having a longer wavelength than light emitted from this organometallic complex. Preferably, the organometallic complex and the fluorescent compound are dispersed as guests in a substance used as a host which has higher singlet excitation energy than that of the fluorescent substance as well as higher triplet excitation energy than that of the organometallic complex.

Note that there is no particular limitation on the substance (i.e. host) used to disperse the organometallic complex and the fluorescent compound, and the substances given as examples of the host in Embodiment 2, or the like can be used.

Although there is also no particular limitation on the fluorescent compound, preferable examples thereof are compounds which can emit red light to infrared light such as 4-dicyanomethylene-2-isopropyl-6-[2-(1,1,7,7-tetramethyljulolidin-9-yl)ethenyl]-4H-pyran (abbreviation: DCJTI), magnesium phthalocyanine, magnesium porphyrin, phthalocyanine and the like.

Note that the first electrode 101 described in this embodiment can have the same structure as the first electrode described in Embodiment 2 and the second electrode 103 in this embodiment can have the same structure as the second electrode described in Embodiment 2.

Further, the hole-injection layer 111, the hole-transport layer 112, the electron-transport layer 114, and the electron-injection layer 115 are provided as illustrated in FIG. 1 in this embodiment, and as for structures of these layers, the structures of the respective layers described in Embodiment 2 can be applied. However, these layers are not necessarily needed, and can be provided as appropriate according to element characteristics.

The above-described light-emitting element can emit light with high efficiency by use of an organometallic complex which is one embodiment of the present invention as a sensitizer.

Note that the structure described in this embodiment can be combined with any of the structures described in Embodiments 1 to 4 as appropriate.

Embodiment 6

In Embodiment 6, as one embodiment of the present invention, a passive matrix light-emitting device and an active matrix light-emitting device each of which is a light-emitting device fabricated using a light-emitting element will be described.

FIGS. 4A to 4D and FIG. 5 illustrate examples of the passive matrix light-emitting device.

In the passive-matrix (also called simple-matrix) light-emitting device, a plurality of anodes arranged in stripes (in stripe form) is provided to intersect at right angles with a plurality of cathodes arranged in stripes. At their intersections, a light-emitting layer is interposed. Thus, light is emitted from a pixel at the intersection of an anode which is selected (to which a voltage is applied) and a cathode which is selected.

Figure 4A:
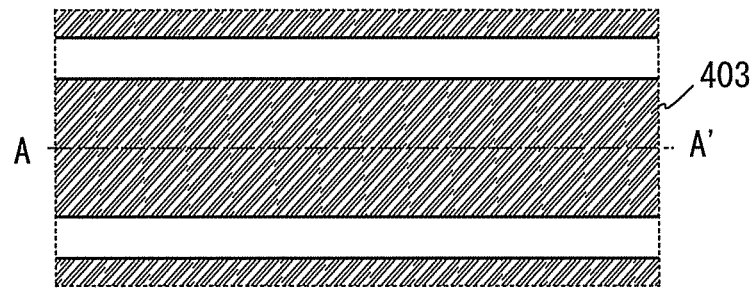
FIGS. 4A to 4D illustrate a passive matrix light-emitting device.
Figure 4B:
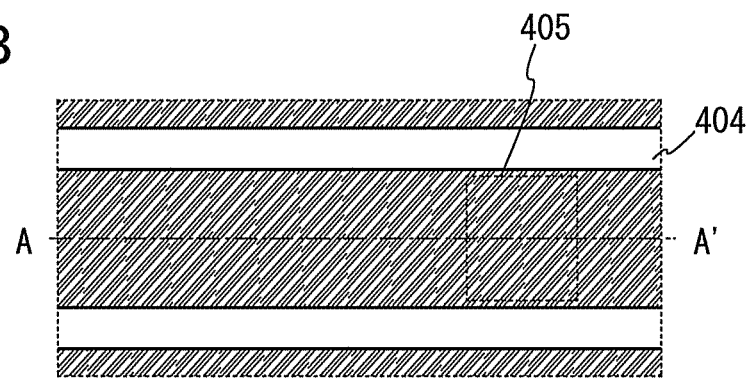
Figure 4C:
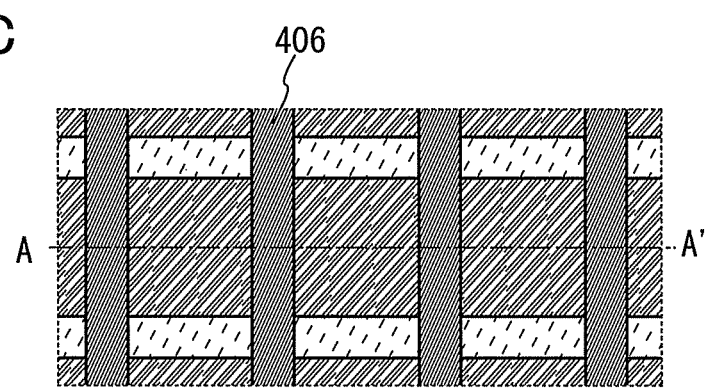
Figure 4D:
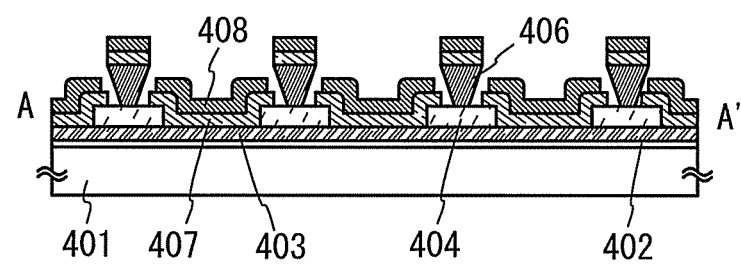

FIGS. 4A to 4C are top views of a pixel portion before sealing. FIG. 4D is a cross-sectional view taken along the chain line A-A' in FIGS. 4A to 4C.

Over a substrate 401, an insulating layer 402 is formed as a base insulating layer. Note that the base insulating layer is not necessarily formed if not needed. Over the insulating layer 402, a plurality of first electrodes 403 is arranged in stripes at regular intervals (FIG. 4A).

In addition, partition 404 having openings corresponding to the pixels is provided over the first electrodes 403. The partition 404 having the openings is formed with an insulating material, such as a photosensitive material or a nonphotosensitive organic material (polyimide, acrylic, polyamide, polyimide amide, resist, or benzocyclobutene) or a SOG film (e.g., a $SiO_x$ film containing an alkyl group). Note that openings 405 corresponding to the pixels serve as light-emitting regions (FIG. 4B).

Over the partition 404 having the openings, a plurality of reversely tapered partitions 406 which are parallel to each other is provided to intersect with the first electrodes 403 (FIG. 4C). The reversely tapered partitions 406 are formed in such a manner that, according to a photolithography method, a positive photosensitive resin, an unexposed portion of which serves as a pattern, is used and the amount of exposed light or the length of development time is adjusted so that a lower portion of the pattern is etched more.

After the reversely tapered partitions 406 are formed as illustrated in FIG. 4C, an EL layer 407 and a second electrode 408 are sequentially formed as illustrated in FIG. 4D. The sum of the heights of the partition 404 having the openings and the reversely tapered partition 406 is set to exceed the sum of the thicknesses of the EL layer 407 and the second electrode 408. Consequently, as illustrated in FIG. 4D, a plurality of divided regions each including the EL layer 407 and the second electrode 408 is formed. Note that the plurality of divided regions is electrically isolated from one another.

The second electrodes 408 are electrodes that extend in the direction in which they intersect with the first electrodes 403 and that are arranged in stripes to be parallel to one another. Although a part of the EL layer 407 and a part of a conductive layer for forming the second electrode 408 are formed even over the reversely tapered partition 406, these parts are isolated from the EL layer 407 and the second electrodes 408.

Note that there is no limitation on the first electrode 403 and the second electrode 408 in this embodiment as long as one of them is an anode and the other is a cathode. Further, the stack structure of the EL layer 407 can be adjusted as appropriate depending on the polarities of the electrodes.

Further, if necessary, a sealing material such as a sealing can or a glass substrate may be attached to the substrate 401 to perform sealing with an adhesive such as a sealant so that a light-emitting element is placed in the sealed space. This can prevents deterioration of the light-emitting element. Note that the sealed space may be filled with a filler or a dry inert gas. Further, a desiccant or the like may be put between the substrate and the sealing material to prevent deterioration of the light-emitting element due to moisture or the like. The desiccant removes a minute amount of moisture, thereby achieving sufficient desiccation. The desiccant can be a substance that absorbs moisture by chemical adsorption, such as an oxide of an alkaline-earth metal typified by calcium oxide or barium oxide. As a desiccant other than the above, a substance that absorbs moisture by physical adsorption, such as zeolite or silica gel, may be used.

Figure 5:
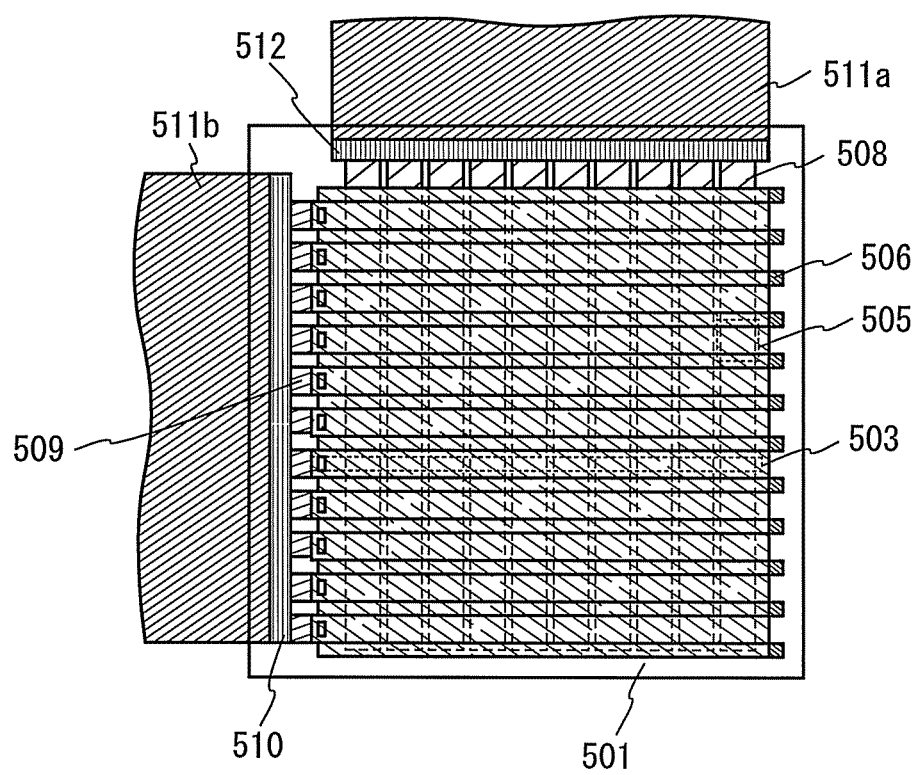
FIG. 5 illustrates a passive matrix light-emitting device.

FIG. 5 is a top view of the passive matrix light-emitting device illustrated in FIGS. 4A to 4D, on which an FPC and the like are mounted.

In FIG. 5, scan lines and data lines intersect at right angles in the pixel portion for displaying images.

Here, the first electrode 403 in FIGS. 4A to 4D corresponds to a scan line 503 in FIG. 5, the second electrode 408 in FIGS. 4A to 4D corresponds to a data line 508 in FIG. 5, and the reversely tapered partition 406 corresponds to a partition 506. The EL layer 407 in FIGS. 4A to 4D is interposed between the data lines 508 and the scan lines 503, and an intersection indicated as a region 505 corresponds to one pixel.

Note that the scanning lines 503 are electrically connected at their ends to connection wirings 509, and the connection wirings 509 are connected to an FPC 511b via an input terminal 510. In addition, the data lines are connected to an FPC 511a via an input terminal 512.

If necessary, an optical film such a polarizing plate, a circularly polarizing plate (including an elliptically polarizing plate), a retardation plate (a quarter-wave plate or a half-wave plate), and a color filter may be provided as appropriate on a surface through which light is emitted. The polarizing plate or the circularly polarizing plate may be provided with an anti-reflection film. For example, anti-glare treatment by which reflected light can be diffused by projections and depressions on the surface so as to reduce the glare can be performed.

Note that, although FIG. 5 illustrates an example in which a driver circuit is not provided over the substrate 501, an IC chip including a driver circuit may be mounted on the substrate 501.

When the IC chip is mounted, in the peripheral (outside) region of the pixel portion, ICs, in which a driver circuit for transmitting a signal to the pixel portion is formed, are mounted on the data line side and/or the scan line side by a COG method. As the mounting technique other than the COG method, a TCP or a wire bonding method may be used. The TCP is obtained by mounting an IC on a TAB tape in such a manner that the TAB tape is connected to a wiring over an element formation substrate and the IC is mounted. The ICs on the data line side and the scan line side may be formed using a silicon substrate, or may be obtained by formation of a driver circuit with a TFT over a glass substrate, a quartz substrate, or a plastic substrate.

Figure 6A:
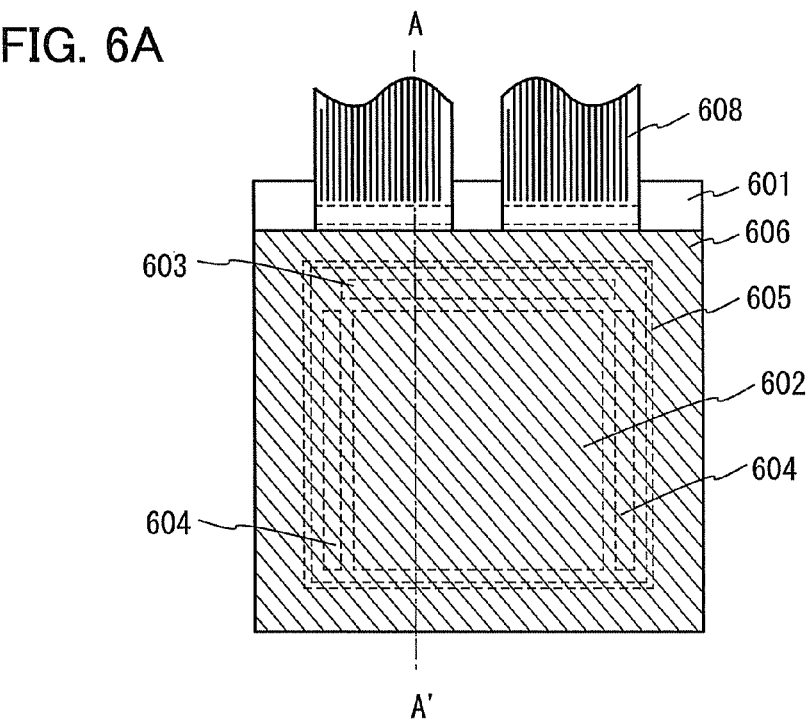
FIGS. 6A and 6B illustrate an active matrix light-emitting device.
Figure 6B:
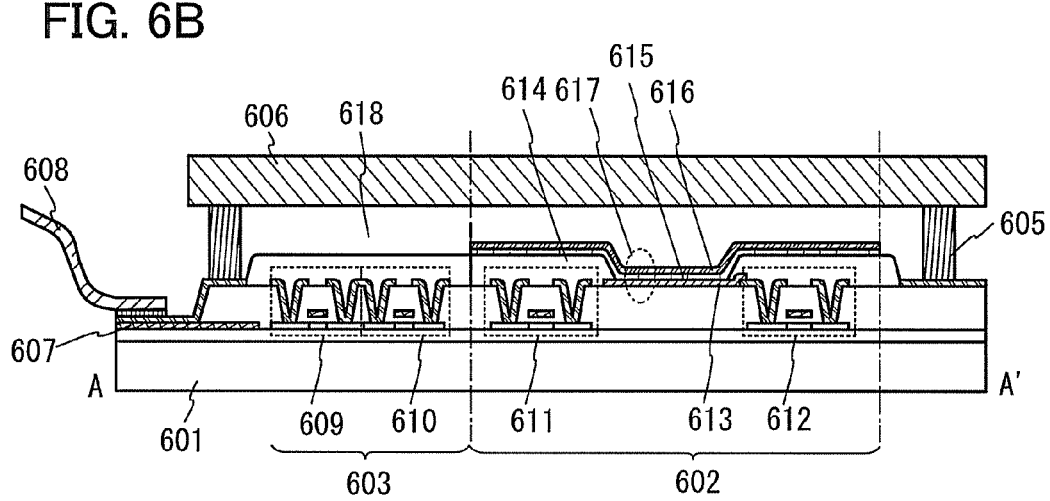

Next, an example of an active-matrix light-emitting device will be described with reference to FIGS. 6A and 6B. Note that FIG. 6A is a top view illustrating the light-emitting device and FIG. 6B is a cross-sectional view taken along the chain line A-A' in FIG. 6A. The active matrix light-emitting device according to this embodiment includes a pixel portion 602 provided over an element substrate 601, a driver circuit portion (a source driver circuit) 603, and a driver circuit portion (a gate driver circuit) 604. The pixel portion 602, the driver circuit portion 603, and the driver circuit portion 604 are sealed between the element substrate 601 and the sealing substrate 606 by the sealing material 605.

In addition, over the element substrate 601, a lead wiring 607 for connecting an external input terminal, through which signals (e.g., a video signal, a clock signal, a start signal, and a reset signal) or a potential from the outside is transmitted to the driver circuit portion 603 and the driver circuit portion 604, is provided. Here, an example in which an FPC (flexible printed circuit) 608 is provided as the external input terminal is described. Although only the FPC is illustrated here, a printed wiring board (PWB) may be attached to this FPC. The light-emitting device in this specification includes not only a light-emitting device itself but also a light-emitting device provided with an FPC or a PWB.

Next, a cross-sectional structure will be described with reference to FIG. 6B. The driver circuit portion and the pixel portion are formed over the element substrate 601, and here the driver circuit portion 603 which is the source driver circuit and the pixel portion 602 are illustrated.

As an example of the driver circuit portion 603, a CMOS circuit which is a combination of an n-channel TFT 609 and a p-channel TFT 610 is formed. Note that a circuit included in the driver circuit portion may be formed with various types of circuits such as CMOS circuits, PMOS circuits, or NMOS circuits. Although a driver integrated type in which the driver circuit is formed over the substrate is illustrated in this embodiment, the driver circuit may not necessarily be formed over the substrate, and the driver circuit can be formed outside, not over the substrate.

The pixel portion 602 includes a plurality of pixels each of which includes a switching TFT 611, a current control TFT 612, and an anode 613 electrically connected to a wiring (a source electrode or a drain electrode) of the current control TFT 612. Note that an insulator 614 is formed to cover an end portion of the anode 613. Here, the insulator 614 is formed using a positive photosensitive acrylic resin.

The insulator 614 is preferably formed so as to have a curved surface with curvature at an upper end portion or a lower end portion thereof in order to obtain favorable coverage by a film which is to be stacked over the insulator 614. For example, in the case where a positive photosensitive acrylic resin is used as a material of the insulator 614, the insulator 614 is preferably formed so as to have a curved surface with a curvature radius (0.2 μm to 3 μm) at the upper end portion. For the insulator 614, either a negative photosensitive material that becomes insoluble in an etchant by light irradiation or a positive photosensitive material that becomes soluble in an etchant by light irradiation can be used, and without limitation to an organic compound, either an organic compound or an inorganic compound such as silicon oxide or silicon oxynitride can be used.

An EL layer 615 and a cathode 616 are stacked over the anode 613. Note that when an ITO film is used as the anode 613, and a stacked film of a titanium nitride film and a film containing aluminum as its main component or a stacked film of a titanium nitride film, a film containing aluminum as its main component, and a titanium nitride film is used as the wiring of the current controlling TFT 612 which is connected to the anode 613, resistance of the wiring is low and favorable ohmic contact with the ITO film can be obtained. Note that, although not illustrated here, the cathode 616 is electrically connected to the FPC 608 which is an external input terminal.

Note that in the EL layer 615, at least a light-emitting layer is provided, and in addition to the light-emitting layer, a hole-injection layer, a hole-transport layer, an electron-transport layer, and an electron-injection layer are provided as appropriate. A light-emitting element 617 has a stacked structure of the anode 613, the EL layer 615, and the cathode 616.

Although the cross-sectional view of FIG. 6B illustrates only one light-emitting element 617, a plurality of light-emitting elements is arranged in matrix in the pixel portion 602. Light-emitting elements which emit three-color (R, G, and B) light are selectively formed in the pixel portion 602, so that a light-emitting device capable of full color display can be formed. Alternatively, a light-emitting device capable of full color display may be obtained by being combined with color filters.

Further, the sealing substrate 606 is attached to the element substrate 601 with the sealing material 605, whereby the light-emitting element 617 is provided in a space 618 enclosed by the element substrate 601, the sealing substrate 606, and the sealing material 605. The space 618 may be filled with an inert gas (such as nitrogen or argon), or the sealing material 605.

Note that an epoxy-based resin is preferably used as the sealing material 605. Such a material preferably allows as little moisture and oxygen as possible to penetrate. As a material used for the sealing substrate 606, a plastic substrate formed of FRP (fiberglass-reinforced plastics), PVF (polyvinyl fluoride), polyester, acrylic, or the like can be used other than a glass substrate or a quartz substrate.

As described above, the active matrix light-emitting device can be obtained.

Note that the structure described in this embodiment can be combined with any of the structures described in Embodiments 1 to 5 as appropriate.

Embodiment 7

In Embodiment 7, with reference to FIGS. 7A to 7E and FIG. 8, description is given of examples of a variety of electronic devices and lighting devices that are completed by using a light-emitting device which is one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 7A to 7E.

Figure 7A:
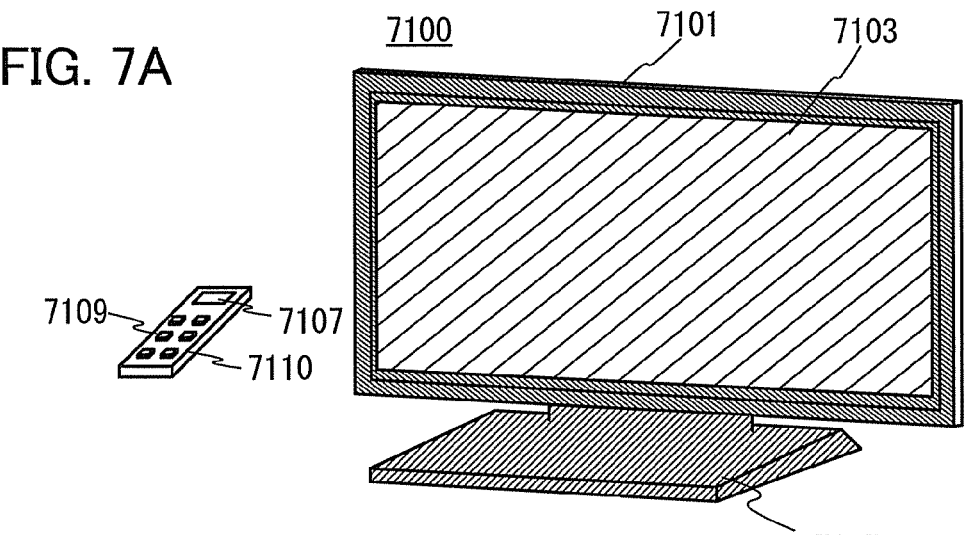
FIGS. 7A to 7E illustrate electronic devices.

FIG. 7A illustrates an example of a television device. In the television device 7100, a display portion 7103 is incorporated into a housing 7101. The display portion 7103 is capable of displaying images, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 7B:
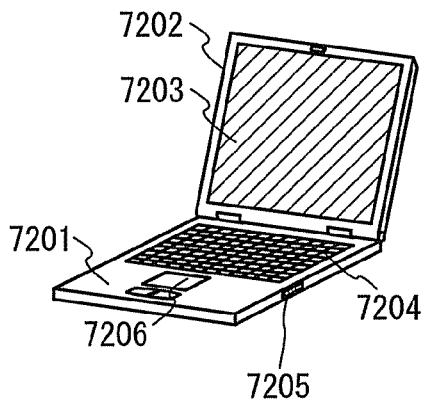

FIG. 7B illustrates a computer having a main body 7201, a housing 7202, a display portion 7203, a keyboard 7204, an external connecting port 7205, a pointing device 7206, and the like. This computer is manufactured by using a light-emitting device for the display portion 7203.

Figure 7C:
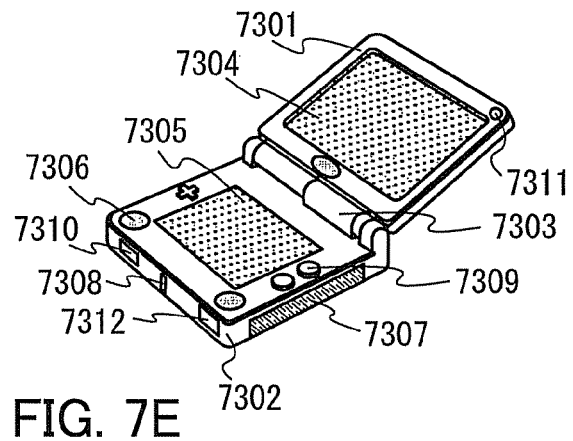

FIG. 7C illustrates a portable game machine having two housings, a housing 7301 and a housing 7302, which are connected with a joint portion 7303 so that the portable game machine can be opened or folded. A display portion 7304 is incorporated into the housing 7301 and a display portion 7305 is incorporated into the housing 7302. In addition, the portable game machine illustrated in FIG. 7C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable games machine is not limited to the above as long as a light-emitting device can be used for at least either the display portion 7304 or the display portion 7305, or both, and may include other accessories arbitrarily. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above.

Figure 7D:
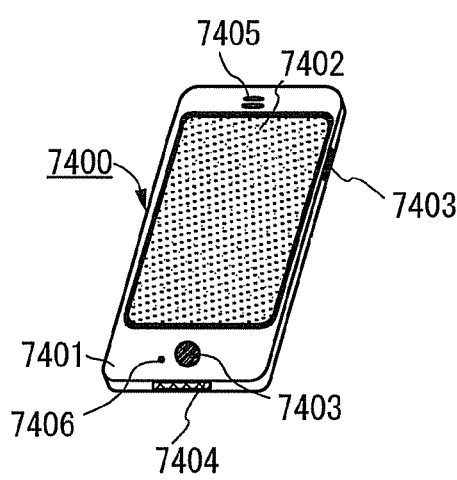

FIG. 7D illustrates an example of a cellular phone. The cellular phone 7400 is provided with operation buttons 7403, an external connection port 7404, a speaker 7405, a microphone 7406, and the like, in addition to a display portion 7402 incorporated into a housing 7401. Note that the cellular phone 7400 is manufactured using a light-emitting device for the display portion 7402.

When the display portion 7402 of the cellular phone 7400 illustrated in FIG. 7D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a text input mode mainly for inputting text is selected for the display portion 7402 so that text displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 can function as an image sensor. For example, an image of a palm print, a fingerprint, or the like is taken by touch on the display portion 7402 with the palm or the finger, whereby personal authentication can be performed. Furthermore, by provision of a backlight or a sensing light source emitting a near-infrared light for the display portion, an image of a finger vein, a palm vein, or the like can also be taken.

Figure 7E:
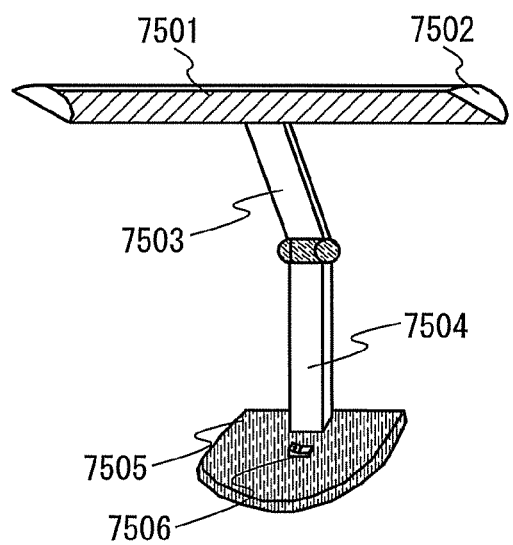

FIG. 7E illustrates a desk lamp including a lighting portion 7501, a shade 7502, an adjustable arm 7503, a support 7504, a base 7505, and a power supply 7506. The desk lamp is manufactured using a light-emitting device for the lighting portion 7501. Note that the "lighting device" also encompasses ceiling lights, wall lights, and the like.

Figure 8:
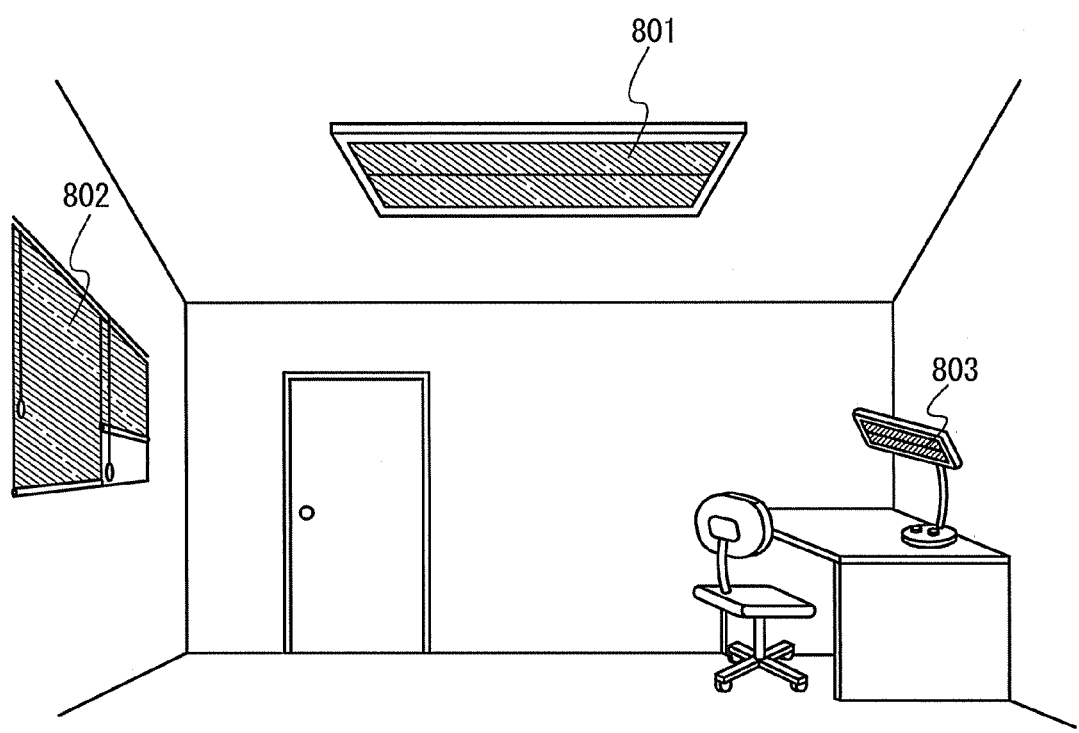
FIG. 8 illustrates lighting devices.

FIG. 8 illustrates an example in which a light-emitting device is used for an interior lighting device 801. Since the light-emitting device can have a larger area, it can be used as a lighting device having a large area. Furthermore, the light-emitting device can be used as a roll-type lighting device 802. As illustrated in FIG. 8, a desk lamp 803 described with reference to FIG. 7E may be used together in a room provided with the interior lighting device 801.

In the above-described manner, electronic devices or lighting devices can be obtained by application of a light-emitting device. Application range of the light-emitting device is so wide that the light-emitting device can be applied to electronic devices in a variety of fields.

Note that the structure described in this embodiment can be combined with any of the structures described in Embodiments 1 to 6 as appropriate.

Example 1

Synthesis Example 1

This example gives descriptions of a method of synthesizing (acetylacetonato)bis[3,5-dimethyl-2-(4-naphthalen-1-yl-phenyl)pyrazinato]iridium(III) (abbreviation: [Ir(dm1nppr)$_2$(acac)]), the organometallic complex represented by Structural Formula (100) in Embodiment 1 which is one embodiment of the present invention. A structure of [Ir(dm1nppr)$_2$(acac)] is illustrated below.

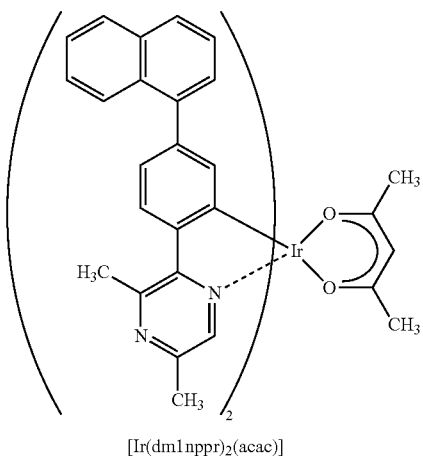

[Ir(dm1nppr)$_2$(acac)]

Step 1: Synthesis of 3,5-Dimethyl-2-(4-naphthalen-1-yl-phenyl)pyrazine (abbreviation: Hdm1nppr)

First, into a recovery flask equipped with a reflux pipe were placed 0.74 g of 2-chloro-3,5-dimethylpyrazine, 1.29 g of 4-(1-naphthyl)phenylboronic acid, 0.55 g of sodium carbonate, 0.024 g of bis(triphenylphosphine)palladium(II)dichloride (abbreviation: Pd(PPh$_3$)$_2$Cl$_2$), 10 mL of water, and 10 mL of acetonitrile, and the air in the flask was replaced with argon. This reaction container was irradiated with microwaves (2.45 GHz, 100 W) for 15 minutes, so that heating was performed. Then, the reaction container was cooled to 50° C. or less. Water was added to the reaction solution, and the organic layer was extracted with dichloromethane. The obtained organic layer was washed with water and dried with magnesium sulfate. The solution which had been dried was filtered. The solvent of this solution was distilled, and recrystallized using ethyl acetate, whereby Hdm1nppr, which is the pyrazine derivative to be produced, was obtained (as a white powder in 50% yield). Note that the microwave irradiation was performed using a microwave synthesis system (Discover, manufactured by CEM Corporation). The synthesis scheme of Step 1 is illustrated in the following (a-1).

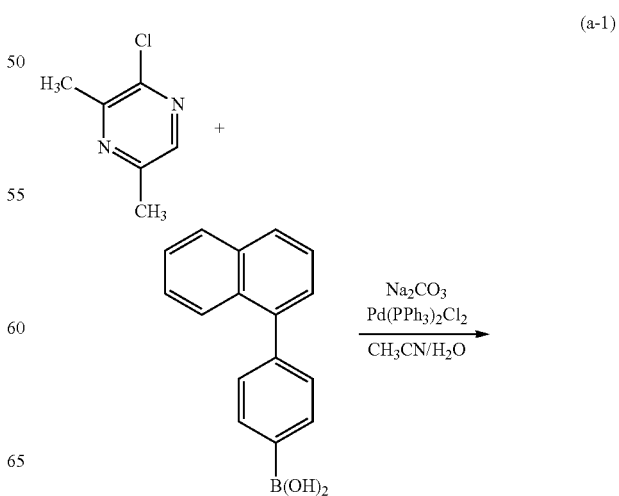

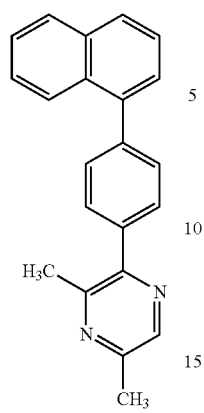

Hdm1nppr

Step 2: Synthesis of Di-μ-chloro-bis[bis{3,5-dimethyl-2-(4-naphthalen-1-yl-phenyl)pyrazinato} iridium(III) (abbreviation: [Ir(dm1nppr)$_2$Cl]$_2$)]

Next, into a recovery flask equipped with a reflux pipe were placed 9 mL of 2-ethoxyethanol, 3 mL of water, 0.80 g of Hdm1nppr obtained in the above Step 1, and 0.31 g of iridium chloride hydrate (IrCl$_3$.H$_2$O) (produced by Sigma-Aldrich Corp.), and the air in the flask was replaced with argon. Then, the mixture was heated by microwave irradiation (2.45 GHz, 100 W) for 30 minutes. Then, the reaction container was cooled to 50° C. or less, and the reaction solution was filtered. The substance obtained by the filtration was washed with ethanol to give a yellowish orange powder of [Ir(dm1nppr)$_2$Cl]$_2$, which is a binuclear complex (in 87% yield). The synthesis scheme of Step 2 is illustrated in the following (b-1).

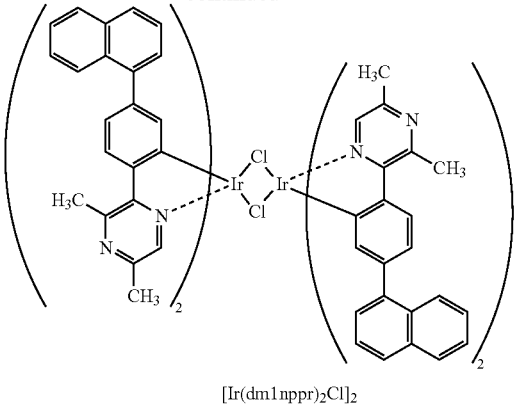

[Ir(dm1nppr)$_2$Cl]$_2$

Step 3: Synthesis of (Acetylacetonato)bis[3,5-dimethyl-2-(4-naphthalen-1-yl-phenyl)pyrazinato]iridium(III) (abbreviation: [Ir(dm1nppr)$_2$(acac)])

Furthermore, into a recovery flask equipped with a reflux pipe were placed 0.77 g of [Ir(dm1nppr)$_2$Cl]$_2$, which is the dinuclear complex obtained in the above Step 2, 10 mL of 2-ethoxyethanol, 0.14 mL of acetylacetone, and 0.48 g of sodium carbonate, and the air in the flask was replaced with argon. Then, the mixture was heated by microwave irradiation (2.45 GHz, 100 W) for 30 minutes. Then, the reaction container was cooled to 50° C. or less, and the reaction solution was filtered. The substance obtained by the filtration was washed sequentially with water, methanol, ethyl acetate, and acetone, whereby an orange powder of the substance to be produced was obtained (in 81% yield). The synthesis scheme of Step 3 is illustrated in the following (c-1).

(c-1)

2 IrCl$_3$·H$_2$O +

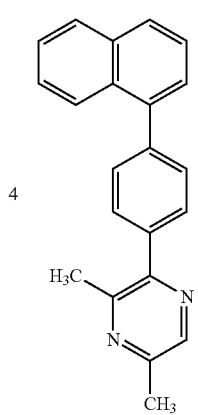

Hdm1nppr $\xrightarrow{\text{2-ethoxyethanol/H}_2\text{O}}$

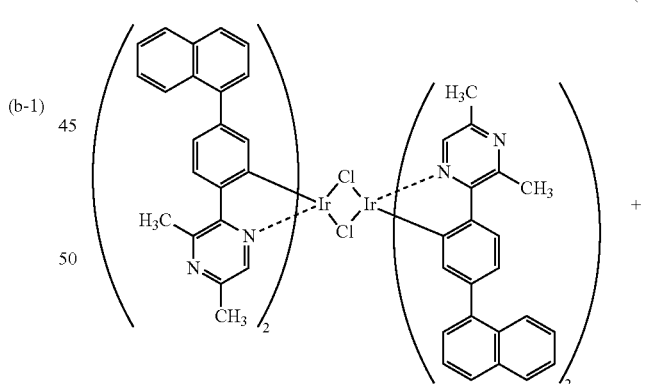

[Ir(dm1nppr)$_2$Cl]$_2$ +

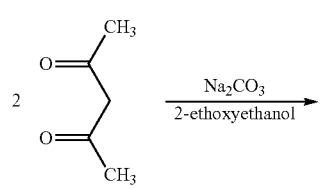

$\xrightarrow{\text{Na}_2\text{CO}_3}{\text{2-ethoxyethanol}}$

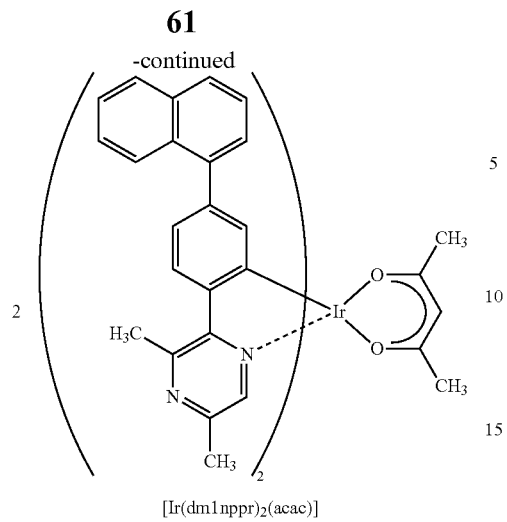

[Ir(dm1nppr)₂(acac)]

Figure 9:
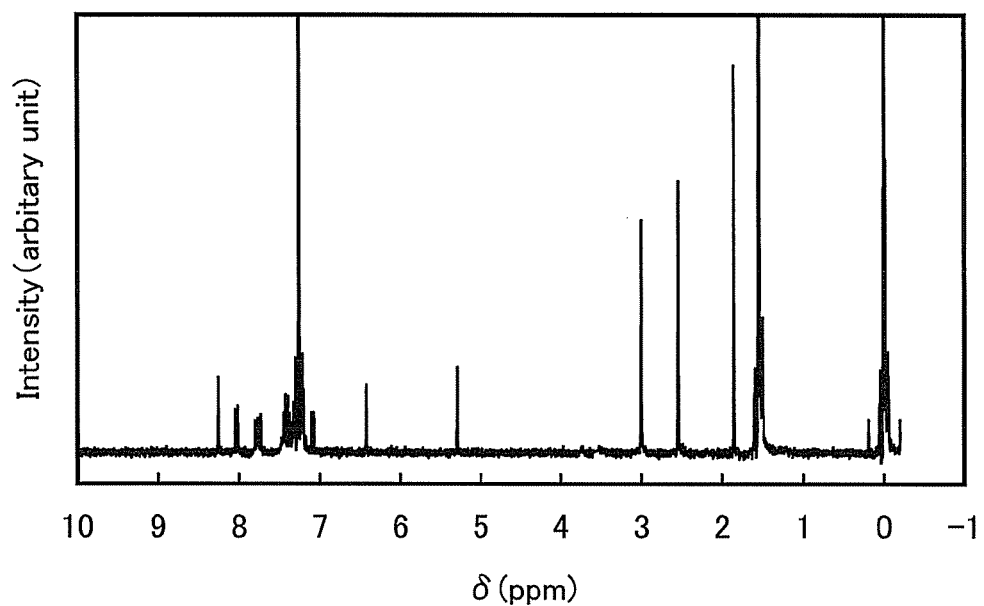
FIG. 9 shows a $^1$H NMR chart of the organometallic complex represented by Structural Formula (100).

The orange powder obtained in the above Step 3 which is the substance to be produced was analyzed by nuclear magnetic resonance (¹H NMR) spectroscopy, results of which are described below. In addition, the ¹H NMR chart is shown in FIG. 9. Thus, [Ir(dm1nppr)₂(acac)], the above-described organometallic complex represented by Structural Formula (100) which is one embodiment of the present invention, was found to be obtained in this example.

¹H NMR. δ (CDCl₃): 1.86 (s, 6H), 2.54 (s, 6H), 3.00 (s, 6H), 5.29 (s, 1H), 6.43 (d, 2H), 7.09 (dd, 2H), 7.21-7.45 (m, 10H), 7.76 (dd, 4H), 8.03 (d, 2H), 8.26 (s, 2H).

Figure 10:
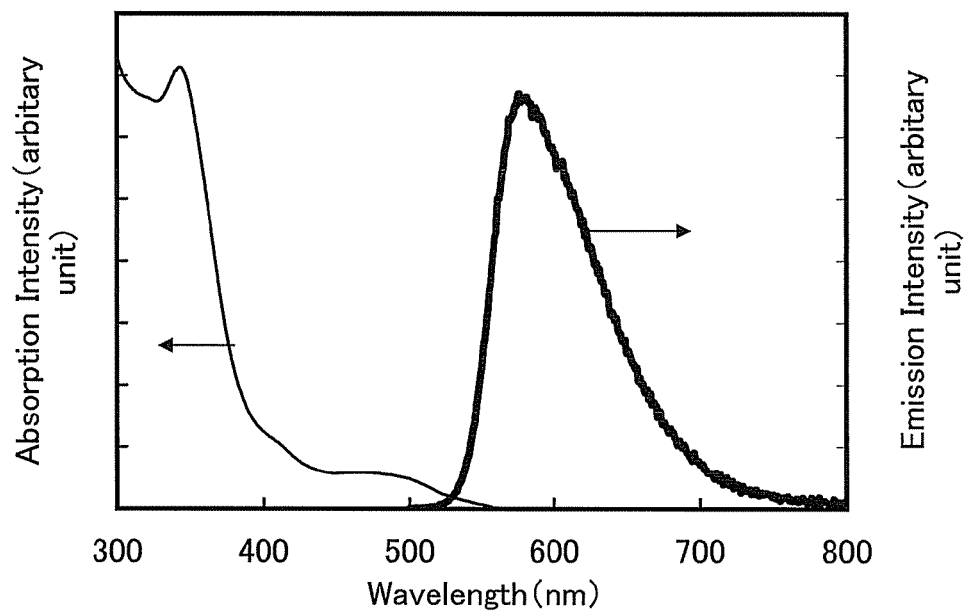
FIG. 10 shows an ultraviolet-visible absorption spectrum and an emission spectrum of an organometallic complex represented by Structural Formula (100).

Next, [Ir(dm1nppr)₂(acac)] was analyzed by ultraviolet-visible (UV-vis) absorption spectroscopy. A UV-vis spectrum was measured with an ultraviolet-visible spectrophotometer (V-550, manufactured by JASCO Corporation) using a dichloromethane solution (0.054 mmol/L) at room temperature. In addition, measurement of an emission spectrum of [Ir(dm1nppr)₂(acac)] was carried out. The emission spectrum was measured with a fluorescence spectrophotometer (FS920, manufactured by Hamamatsu Photonics Corporation) using a degassed dichloromethane solution (0.32 mmol/L) at room temperature. FIG. 10 shows results of the measurements, in which the horizontal axis represents wavelength (nm) and the vertical axis represents absorption intensity (arbitrary unit) and emission intensity (arbitrary unit).

As shown in FIG. 10, [Ir(dm1nppr)₂(acac)], the organometallic complex which is one embodiment of the present invention, has an emission peak at 580 nm, and orange light was observed from the dichloromethane solution.

The decomposition temperature of [Ir(dm1nppr)₂(acac)], the obtained organometallic complex which is one embodiment of the present invention, was measured with a high vacuum differential type differential thermal balance (TG-DTA2410SA, manufactured by Bruker AXS K.K.). The temperature was increased at a temperature increase rate of 10° C./min, whereby a 5% reduction in weight was observed at 350° C., which is indicative of high heat resistance.

Example 2

Synthesis Example 2

This example gives descriptions of a method of synthesizing (acetylacetonato)bis[3,5-dimethyl-2-(4-naphthalen-2-yl-phenyl)pyrazinato] iridium(III) (abbreviation: [Ir(dm2nppr)₂(acac)]), the organometallic complex represented by Structural Formula (116) in Embodiment 1 which is one embodiment of the present invention. A structure of [Ir(dm2nppr)₂(acac)] is illustrated below.

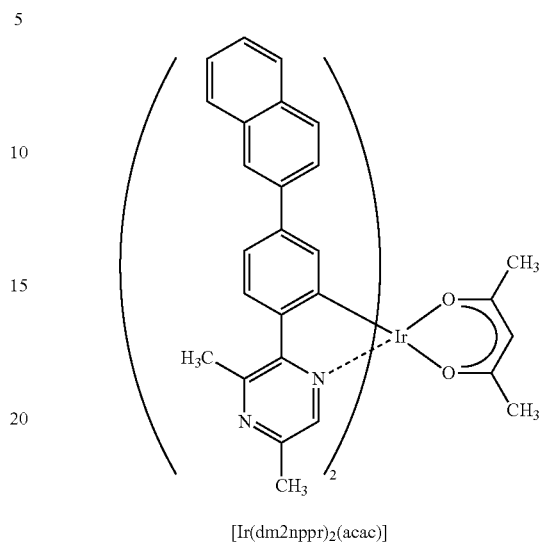

[Ir(dm2nppr)₂(acac)]

Step 1: Synthesis of 2-(4-Bromophenyl)naphthalene

First, into a 200-mL three-neck flask were placed 9.7 g of 4-bromoiodobenzene, 3.1 g of 2-naphthylboronic acid, and 0.35 g of tri(ortho-tolyl)phosphine (P(o-tolyl)₃), to which 30 mL of toluene, 6 mL of ethanol, and 10 mL of a 2.0M aqueous potassium carbonate solution were added. The mixture in this flask was degassed under reduced pressure, and the air in the flask was replaced with nitrogen. To this mixture was added 0.037 g of palladium(II) acetate, and the mixture was refluxed under a nitrogen stream at 90° C. for 6 hours. After the reflux, organic substances were extracted from the aqueous layer of this mixture with toluene. The solution of the extract was combined with the organic layer of the mixture. The resulting mixture was washed with a saturated aqueous solution of sodium hydrogen carbonate and then saturated brine. After the washing, anhydrous magnesium sulfate was added for drying. The obtained mixture was separated by gravity filtration, and the filtrate was concentrated to give a solid. The obtained solid was purified by silica gel column chromatography. In the column chromatography, hexane was first used as a developing solvent, and then a mixed solvent in which a hexane/ethyl acetate ratio was 20:1 (v/v) was used. The obtained fractions were concentrated to give a solid. The obtained solid was recrystallized using a mixed solvent of toluene and hexane to give 2-(4-bromophenyl)naphthalene (as a white solid in 61% yield). The synthesis scheme of Step (a-2) is illustrated below.

(a-2)

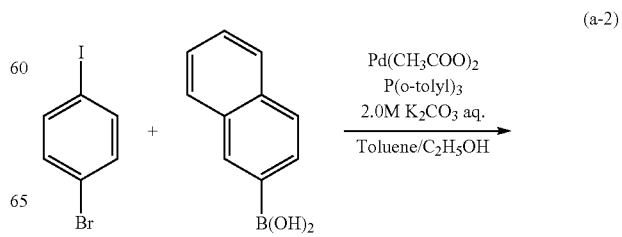

Step 2: Synthesis of 4-(2-Naphthyl)phenylboronic acid

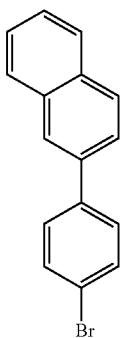

Next, 5.0 g of 2-(4-bromophenyl)naphthalene obtained in the above Step 1 was placed into a 300-mL three-neck flask, and the air in the flask was replaced with nitrogen. To this compound was added 100 mL of tetrahydrofuran (THF), and this mixture solution was stirred at −78° C. for 20 minutes. Then, 13 mL of a 1.7M hexane solution of n-butyllithium (n-BuLi) was dripped into this mixture solution, followed by stirring at −78° C. for 2 hours. After the predetermined time had elapsed, 4.0 mL of trimethyl borate was added, and the mixture was stirred for 19 hours while the temperature was raised to room temperature. After the predetermined time had elapsed, 100 mL of 1.0M hydrochloric acid was poured into this reaction solution, and the mixture was stirred for 1 hour. Then, this mixture solution was separated into an organic layer and an aqueous layer. Organic substances were extracted with ethyl acetate from the obtained aqueous layer. The solution of this extract was combined with the organic layer that had been first obtained, and the mixture was washed with saturated brine and dried with anhydrous magnesium sulfate. Then, the filtrate obtained by gravity filtration was concentrated to give a white solid. The obtained solid was recrystallized using a mixed solvent of chloroform and hexane, whereby 4-(2-naphthyl)phenylboronic acid was obtained (as a white powder in 36% yield). The synthesis scheme of Step (b-2) is illustrated below.

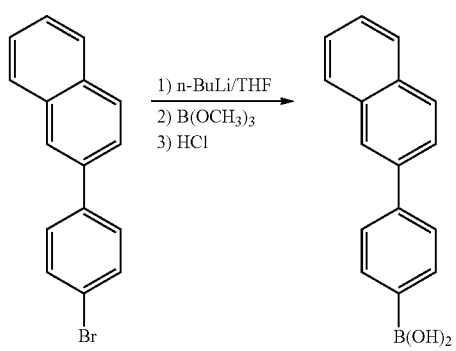

(b-2)

Step 3: Synthesis of 3,5-Dimethyl-2-(4-naphthalen-2-yl-phenyl)pyrazine (abbreviation: Hdm2nppr)

First, into a recovery flask equipped with a reflux pipe were placed 0.55 g of 2-chloro-3,5-dimethylpyrazine, 0.96 g of 4-(2-naphthyl)phenylboronic acid, 0.41 g of sodium carbonate, 0.018 g of bis(triphenylphosphine)palladium(II)dichloride (abbreviation: Pd(PPh₃)₂Cl₂), 10 mL of water, and 10 mL of acetonitrile, and the air in the flask was replaced with argon. This reaction container was irradiated with microwaves (2.45 GHz, 100 W) for 50 minutes, so that heating was performed. Then, the reaction container was cooled to 50° C. or less. Water was added to the reaction solution, and the organic layer was extracted with dichloromethane. The obtained organic layer was washed with water and dried with magnesium sulfate. The solution which had been dried was filtered. The solvent of this solution was distilled, and recrystallized using methanol, whereby Hdm2nppr, which is the pyrazine derivative to be produced, was obtained (as a white powder in 85% yield). Note that the microwave irradiation was performed using a microwave synthesis system (Discover, manufactured by CEM Corporation). The synthesis scheme of Step 3 is illustrated in the following (c-2).

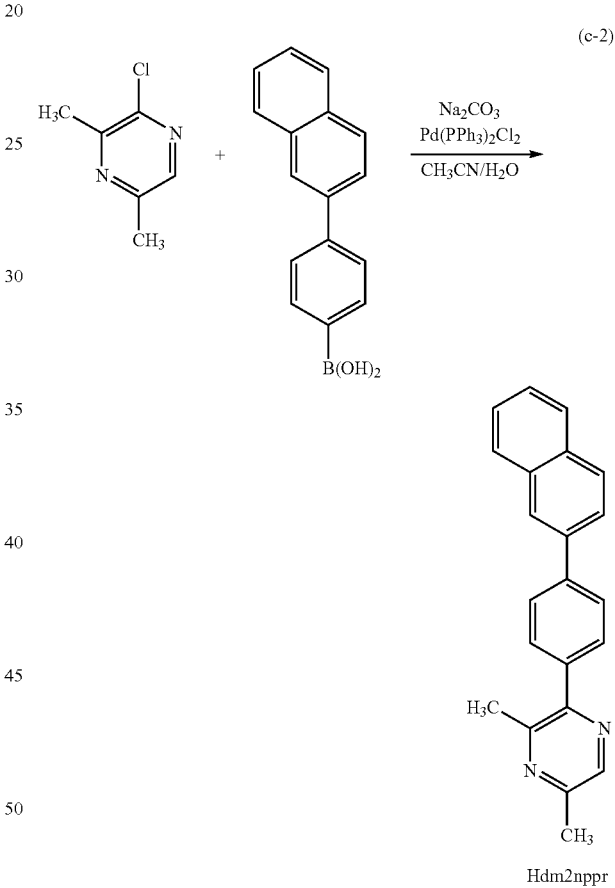

(c-2)

Step 4: Synthesis of Di-μ-chloro-bis[bis {3,5-dimethyl-2-(4-naphthalen-2-yl-phenyl)pyrazinato}iridium(III) (abbreviation: [Ir(dm2nppr)₂Cl]₂)]

Next, into a recovery flask equipped with a reflux pipe were placed 1.03 g of Hdm2nppr obtained in the above Step 3, 12 mL of 2-ethoxyethanol, 4 mL of water, and 0.47 g of iridium chloride hydrate (IrCl₃.H₂O) (produced by Sigma-Aldrich Corp.), and the air in the flask was replaced with argon. Then, the mixture was heated by microwave irradiation (2.45 GHz, 100 W) for 30 minutes. Then, the reaction container was cooled to 50° C. or less, and the reaction solution was filtered. The substance obtained by the filtration was washed with ethanol to give an orange powder of [Ir(dm2nppr)$_2$Cl]$_2$, which is a binuclear complex (in 54% yield). The synthesis scheme of Step 4 is illustrated in the following (d-2).

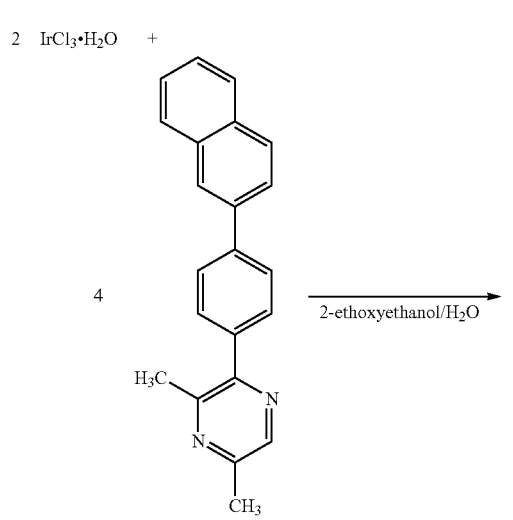

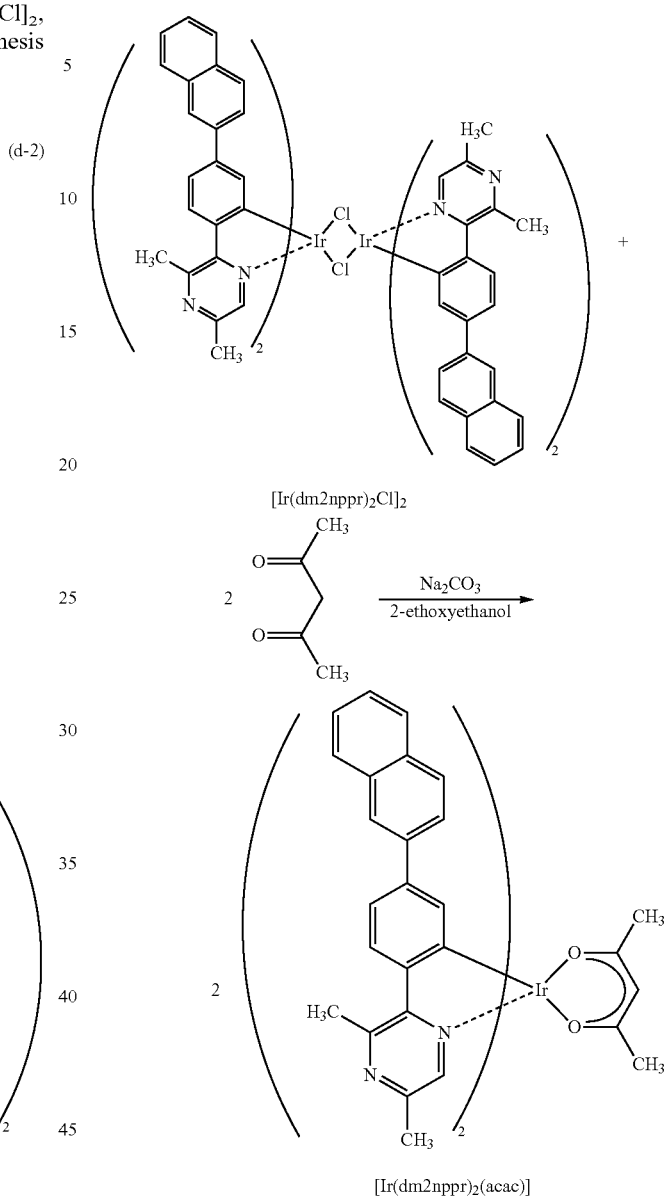

Step 5: Synthesis of (Acetylacetonato)bis[3,5-dimethyl-2-(4-naphthalen-2-yl-phenyl)pyrazinato] iridium(III) (abbreviation: [Ir(dm2nppr)$_2$(acac)])

Furthermore, into a recovery flask equipped with a reflux pipe were placed 0.77 g of [Ir(dm2nppr)$_2$Cl]$_2$, which is the dinuclear complex obtained in the above Step 4, 10 mL of 2-ethoxyethanol, 0.13 mL of acetylacetone, and 0.46 g of sodium carbonate, and the air in the flask was replaced with argon. Then, the mixture was heated by microwave irradiation (2.45 GHz, 100 W) for 30 minutes. Then, the reaction container was cooled to 50° C. or less, and the reaction solution was filtered. The substance obtained by the filtration was washed sequentially with water, ethanol, and ether, whereby a reddish orange powder of the substance to be produced was obtained (in 74% yield). The synthesis scheme of Step 5 is illustrated in the following (e-2).

Figure 12:
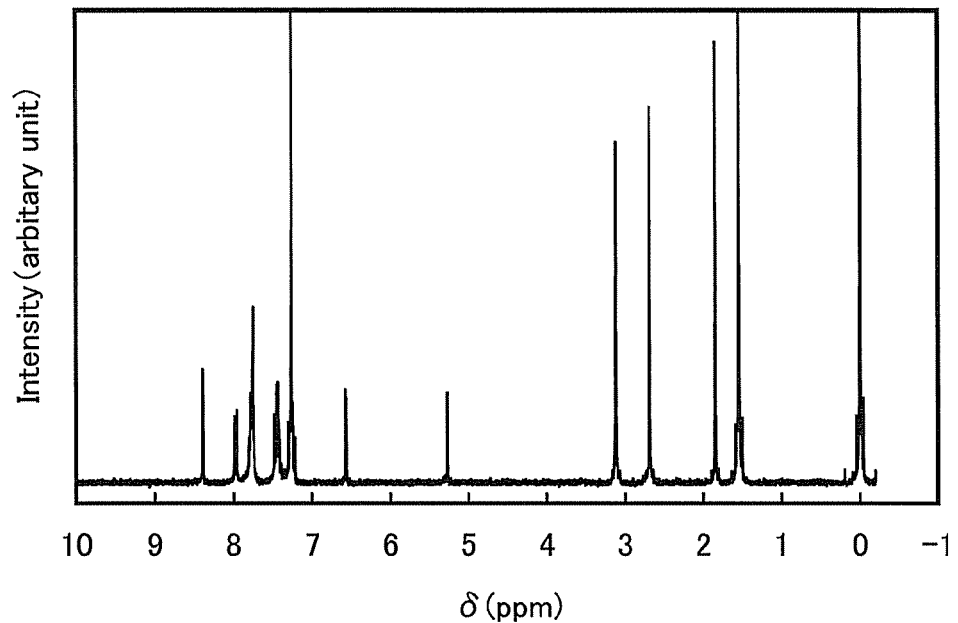
FIG. 12 shows a $^1$H NMR chart of an organometallic complex represented by Structural Formula (116).

The reddish orange powder obtained in the above Step 5 which is the substance to be produced was analyzed by nuclear magnetic resonance ($^1$H NMR) spectroscopy, results of which are described below. In addition, the $^1$H NMR chart is shown in FIG. 12. Thus, [Ir(dm2nppr)$_2$(acac)], the above-described organometallic complex represented by Structural Formula (116) which is one embodiment of the present invention, was found to be obtained in this example.

$^1$H NMR. δ (CDCl$_3$): 1.85 (s, 6H), 2.69 (s, 6H), 3.12 (s, 6H), 5.27 (s, 1H), 6.57 (d, 2H), 7.27 (m, 6H), 7.41 (m, 4H), 7.75 (m, 6H), 7.97 (d, 2H), 8.39 (s, 2H).

Figure 13:
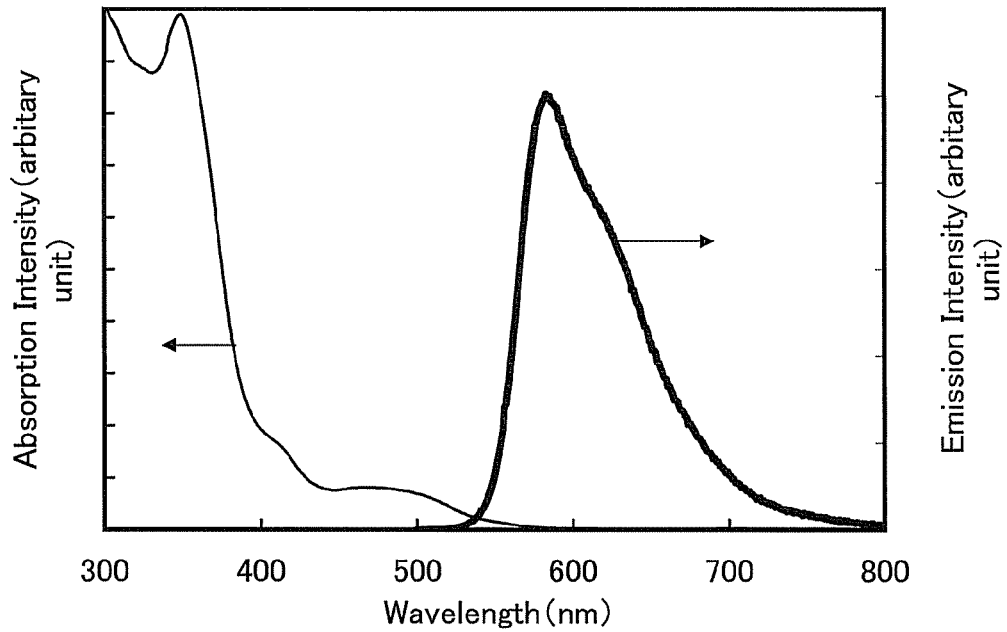
FIG. 13 shows an ultraviolet-visible absorption spectrum and an emission spectrum of an organometallic complex represented by Structural Formula (116).

Next, [Ir(dm2nppr)$_2$(acac)] was analyzed by ultraviolet-visible (UV-vis) absorption spectroscopy. A UV-vis spectrum was measured with an ultraviolet-visible spectrophotometer (V-550, manufactured by JASCO Corporation) using a dichloromethane solution (0.061 mmol/L) at room temperature. In addition, measurement of an emission spectrum of [Ir(dm2nppr)$_2$(acac)] was carried out. The emission spectrum was measured with a fluorescence spectrophotometer (FS920, manufactured by Hamamatsu Photonics Corporation) using a degassed dichloromethane solution (0.37 mmol/L) at room temperature. FIG. 13 shows results of the measurements, in which the horizontal axis represents wavelength (nm) and the vertical axis represents absorption intensity (arbitrary unit) and emission intensity (arbitrary unit).

As shown in FIG. 13, [Ir(dm2nppr)$_2$(acac)], the organometallic complex which is one embodiment of the present invention, has an emission peak at 584 nm, and orange light was observed from the dichloromethane solution.

The decomposition temperature of [Ir(dm2nppr)$_2$(acac)], the obtained organometallic complex which is one embodiment of the present invention, was measured with a high vacuum differential type differential thermal balance (TG-DTA2410SA, manufactured by Bruker AXS K.K.). The temperature was increased at a temperature increase rate of 10° C./min, whereby a 5% reduction in weight was observed at 352° C., which is indicative of high heat resistance.

Example 3

Figure 11:
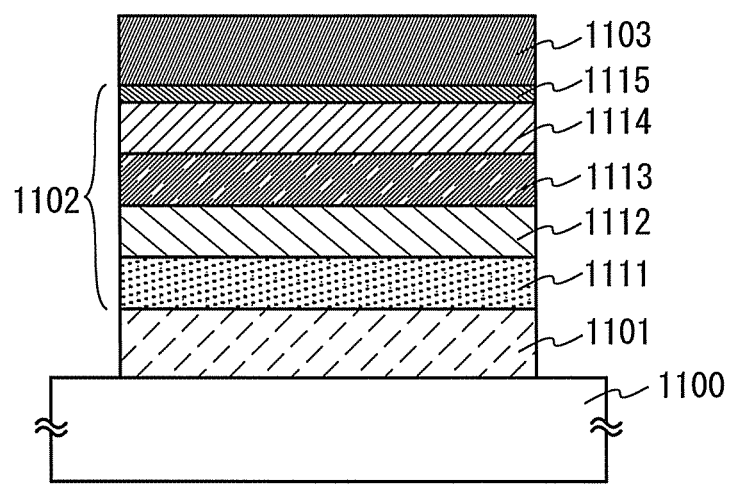
FIG. 11 illustrates a light-emitting element which is one embodiment of the present invention.

This example gives description of a light-emitting element (Light-Emitting Element 1) including [Ir(dm1nppr)$_2$(acac)] (Structural Formula (100)), the organometallic complex which is one embodiment of the present invention and was synthesized in Example 1, as a light-emitting substance, and a light-emitting element (Light-Emitting Element 2) including [Ir(dm2nppr)$_2$(acac)] (Structural Formula (116)), the organometallic complex which is one embodiment of the present invention and was synthesized in Example 2, as a light-emitting substance. Further, the description contains a reference light-emitting element (Light-Emitting Element 3) including (acetylacetonato)bis(5-isopropyl-3-methyl-2-phenylpyrazinato)iridium(III) (abbreviation: [Ir(mppr-iPr)$_2$(acac)]), which is a substance represented by Structural Formula (i) below, as a light-emitting substance. Note that structures of other organic compounds used in this example are represented by Structural Formulae (i) to (v) below. Furthermore, an example of a method of synthesizing Cz1PQ-III represented by Structural Formula (iii) below will be given. In addition, element structures of the light-emitting elements will be described on the basis of FIG. 11.

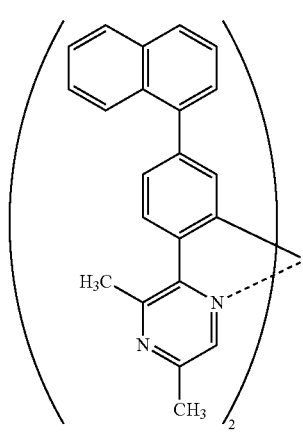

Ir(dm1nppr)$_2$(acac) (100)

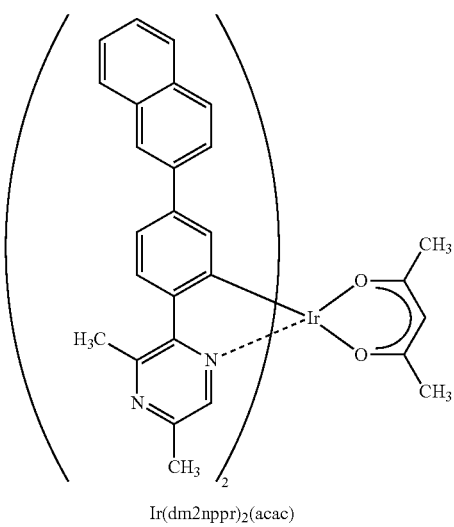

Ir(dm2nppr)$_2$(acac) (116)

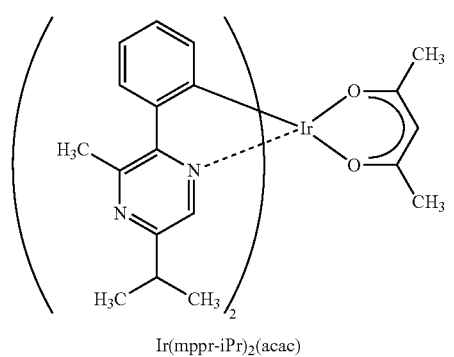

Ir(mppr-iPr)$_2$(acac) (i)

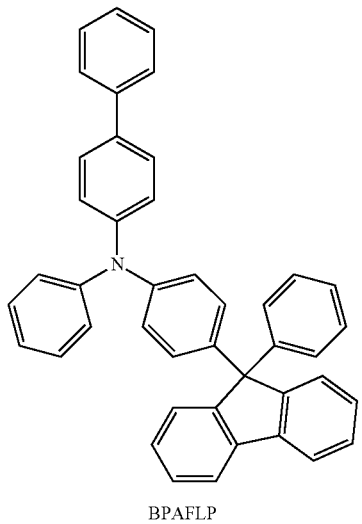

BPAFLP (ii)

-continued (iii)

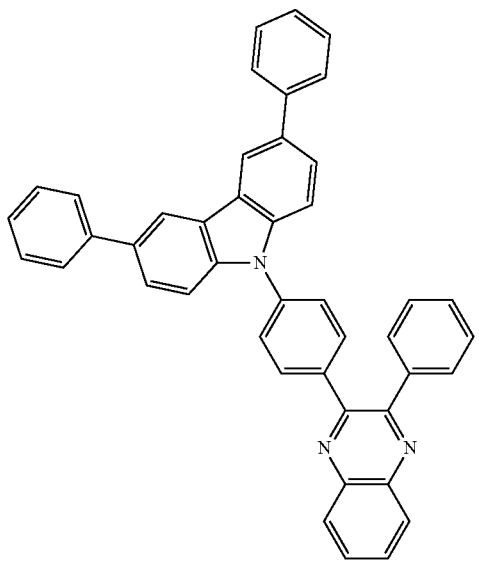

Cz1PQ-III (iv)

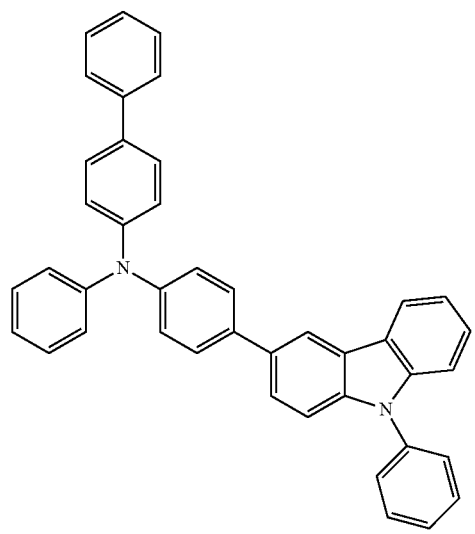

PCBA1BP (v)

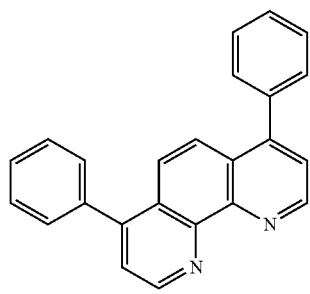

BPhen

Method of Synthesizing 2-[4-(3,6-Diphenyl-9H-carbazol-9-yl)phenyl]-3-phenylquinoxaline (abbreviation: Cz1PQ-III)

First, into a 200-mL three-neck flask were placed 2.2 g (6.0 mmol) of 2-(4-bromophenyl)-3-phenylquinoxaline, 1.9 g (6.0 mmol) of 3,6-diphenyl-9H-carbazole, and 1.1 g (12.0 mmol) of sodium tert-butoxide. The air in the flask was replaced with nitrogen, and 60 mL of xylene was placed into this flask. The mixture was degassed by stirring under reduced pressure. To this mixture were added 0.2 mL of tri(tert-butyl)phosphine and 71 mg (0.12 mmol) of bis(benzylideneacetone)palladium(0). This mixture was stirred under a nitrogen stream at 140° C. for 6 hours. After the predetermined time had elapsed, water was added to the obtained mixture, and the mixture was separated into an organic layer and an aqueous layer. Organic substances were extracted with toluene from the aqueous layer. The solution of the obtained extract was combined with the organic layer, and the mixture was washed with saturated brine and dried with magnesium sulfate. The obtained mixture was gravity filtered, and the filtrate was concentrated to give an oily substance. This oily substance was purified by silica gel column chromatography (with a developing solvent of toluene), followed by recrystallization from toluene, whereby 3.0 g of a yellow powder of Cz1PQ-III, which is the substance to be produced, was obtained in 81% yield.

By a train sublimation method, 3.2 g of the obtained yellow powder of Cz1PQ-III, which is the substance to be produced, was sublimated and purified. In the sublimation and the purification, the yellow powder was heated at 300° C. under a pressure of 2.3 Pa with a flow rate of argon gas of 5 mL/min. After that, 3.1 g of a yellow powder of Cz1PQ-III, which is the substance to be produced, was obtained in 96% yield. The synthesis scheme of Cz1PQ-III is illustrated in the following (a-3).

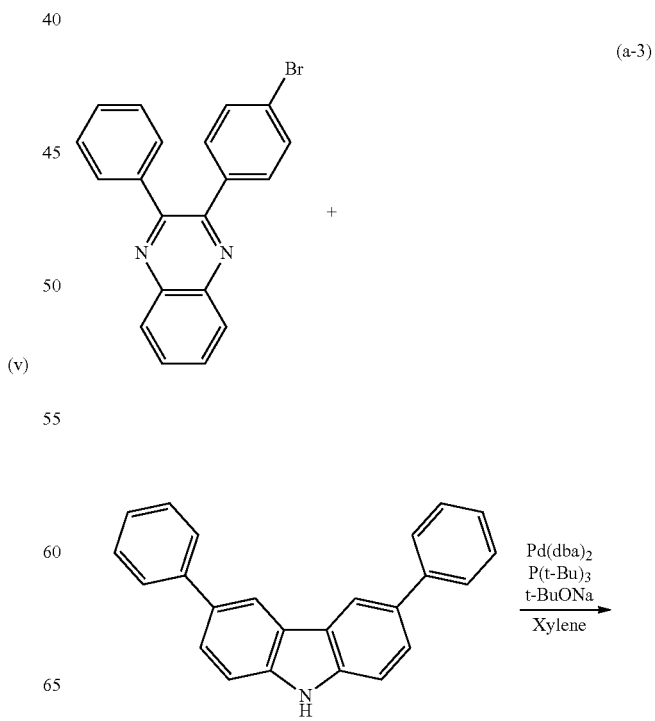

(a-3)

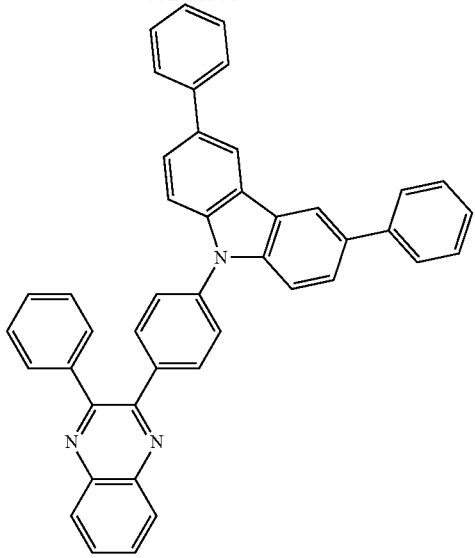

Further, $^1$H NMR data of the obtained compound are as follows: $^1$H NMR (CDCl$_3$, 300 MHz): δ=7.34-7.38 (m, 2H), 7.43-7.53 (m, 9H), 7.60-7.86 (m, 14H), 8.22-8.26 (m, 2H), 8.40 (d, J=1.5 Hz, 2H).

[Formation of Light-Emitting Elements 1 to 3]

First, as a first electrode 1101, an indium tin oxide containing silicon oxide (ITSO) is formed to a thickness of 110 nm over a substrate 1100 made of glass. Note that a surface of the ITSO film is covered with an insulating film so that a 2 mm square portion of the surface is exposed. Here, the first electrode 1101 is an electrode that functions as an anode of the light-emitting element.

Next, as pretreatment for forming the light-emitting elements over the substrate 1100, a surface of the substrate was washed with water, baked at 200° C. for 1 hour, and subjected to UV ozone treatment for 370 seconds.

After that, the substrate was transferred into a vacuum evaporation apparatus in which the pressure had been reduced to approximately $10^{-4}$ Pa, and subjected to vacuum baking at 170° C. for 30 minutes in a heating chamber of the vacuum evaporation apparatus. Then, the substrate 1100 was cooled down for about 30 minutes.

Next, the substrate 1100 was fixed to a holder provided in the vacuum evaporation apparatus so that the surface of the substrate 1100 on which the first electrode 1101 was formed faced downward. In the case described in this example, a hole-injection layer 1111, a hole-transport layer 1112, a light-emitting layer 1113, an electron-transport layer 1114, and an electron-injection layer 1115 which are included in an EL layer 1102 are sequentially formed.

After the pressure in the vacuum evaporation apparatus was reduced to about $10^{-4}$ Pa, BPAFLP represented by the above Structural Formula (ii) and molybdenum oxide were co-evaporated with a mass ratio of BPAFLP to molybdenum oxide being 4:2, whereby the hole-injection layer 1111 was formed. The thickness thereof was 50 nm. Note that the co-evaporation refers to an evaporation method in which different substances are evaporated from the respective different evaporation sources at the same time.

Next, BPAFLP was evaporated to a thickness of 10 nm, whereby the hole-transport layer 1112 was formed.

Next, the light-emitting layer 1113 was formed over the hole-transport layer 1112. For Light-Emitting Element 1, Cz1PQ-III represented by the above Structural Formula (iii), 4-phenyl-4'-(9-phenyl-9H-carbazol-3-yl)triphenylamine (abbreviation: PCBA1BP) represented by the above Structural Formula (iv), and [Ir(dm1nppr)$_2$(acac)] represented by the above Structural Formula (100) were co-evaporated over the hole-transport layer 1112 with a mass ratio of Cz1PQ-III: PCBA1BP: [Ir(dm1nppr)$_2$(acac)] being 1:0.5:0.1. For Light-Emitting Element 2, Cz1PQ-III, PCBA1BP, and [Ir(dm2nppr)$_2$(acac)] represented by the above Structural Formula (116) were co-evaporated over the hole-transport layer 1112 with a mass ratio of Cz1PQ-III:PCBA1BP:[Ir(dm2nppr)$_2$(acac)] being 1:0.5:0.1. For Light-Emitting Element 3, Cz1PQ-III, PCBA1BP, and [Ir(mppr-iPr)$_2$(acac)] represented by the above Structural Formula (i) were co-evaporated over the hole-transport layer 1112 with a mass ratio of Cz1PQ-III:PCBA1BP:[Ir(mppr-iPr)$_2$(acac)] being 1:0.5:0.1. Thus, each light-emitting layer 1113 was formed. The thickness of each light-emitting layer was 40 nm.

Next, Cz1PQ-III represented by the above Structural Formula (iii) was evaporated to a thickness of 10 nm and then bathophenanthroline (abbreviation: BPhen) represented by the above Structural Formula (v) was evaporated to a thickness of 20 mu, whereby the electron-transport layer 1114 was formed. Furthermore, lithium fluoride was evaporated to a thickness of 2 nm over the electron-transport layer 1114, whereby the electron-injection layer 1115 was formed.

Next, an aluminum film was formed to a thickness of 200 nm as a second electrode 1103. Thus, Light-Emitting Elements 1 to 3 were obtained. Note that the second electrode 1103 is an electrode that functions as a cathode. Note that in all of the above evaporation steps, a resistance heating method was adopted.

Further, these light-emitting elements were sealed in a glove box under a nitrogen atmosphere to prevent from being exposed to the atmosphere.

[Operation Characteristics of Light-Emitting Elements 1 to 3]

Operation characteristics of the formed light-emitting elements (Light-Emitting Elements 1 to 3) were measured. Note that the measurements were carried out at room temperature (in an atmosphere kept at 25° C.).

Figure 14:
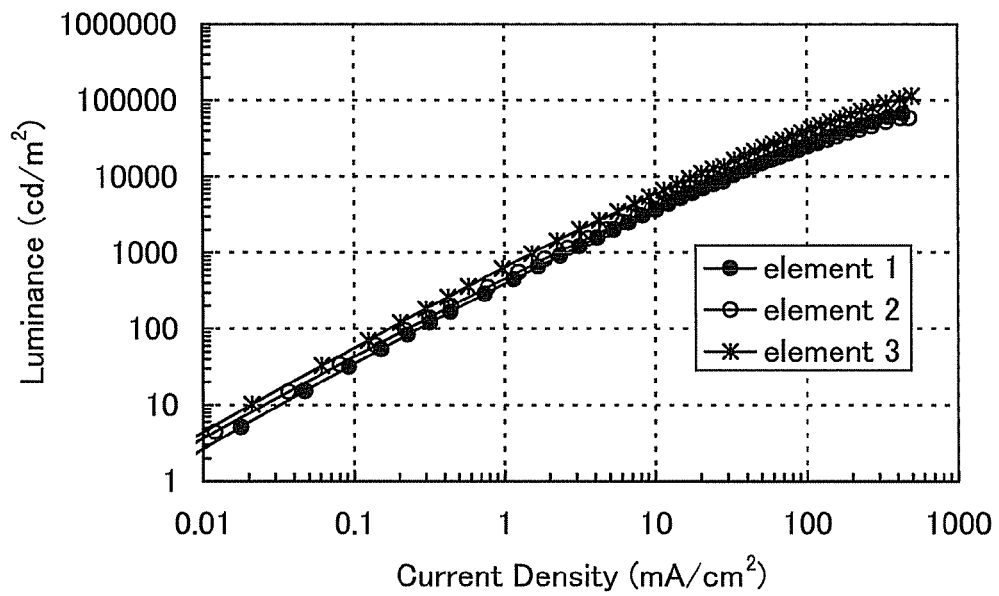
FIG. 14 shows current density versus luminance characteristics of light-emitting elements which are embodiments of the present invention.
Figure 15:
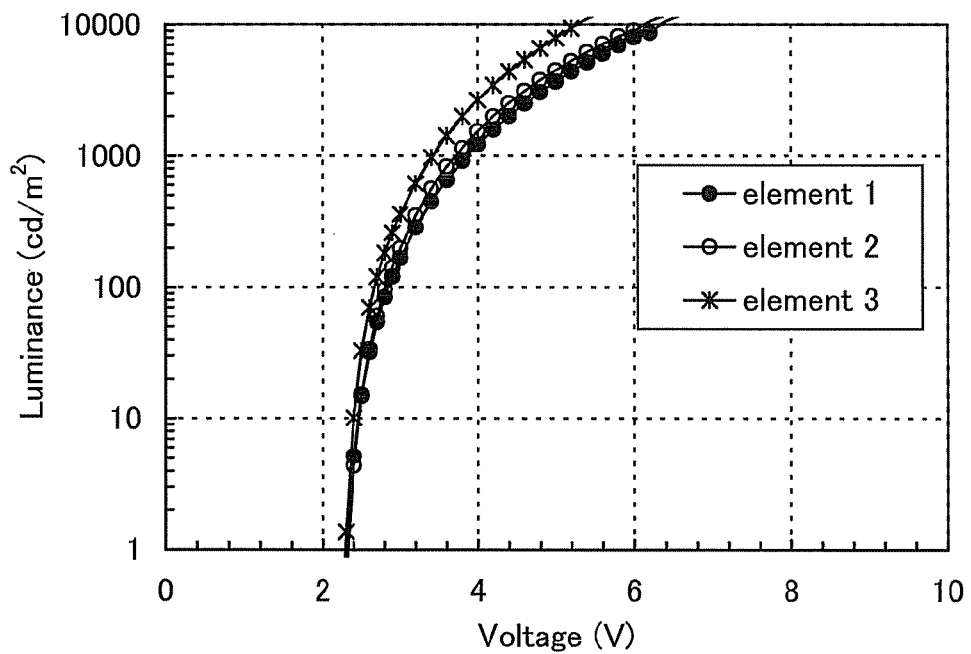
FIG. 15 shows voltage versus luminance characteristics of light-emitting elements which are embodiments of the present invention.

FIG. 14 shows current density versus luminance characteristics of the light-emitting elements. In FIG. 14, the vertical axis represents luminance (cd/m$^2$) and the horizontal axis represents current density (mA/cm$^2$). FIG. 15 shows voltage versus luminance characteristics of the light-emitting elements. In FIG. 15, the vertical axis represents luminance (cd/m$^2$) and the horizontal axis represents voltage (V).

Figure 16:
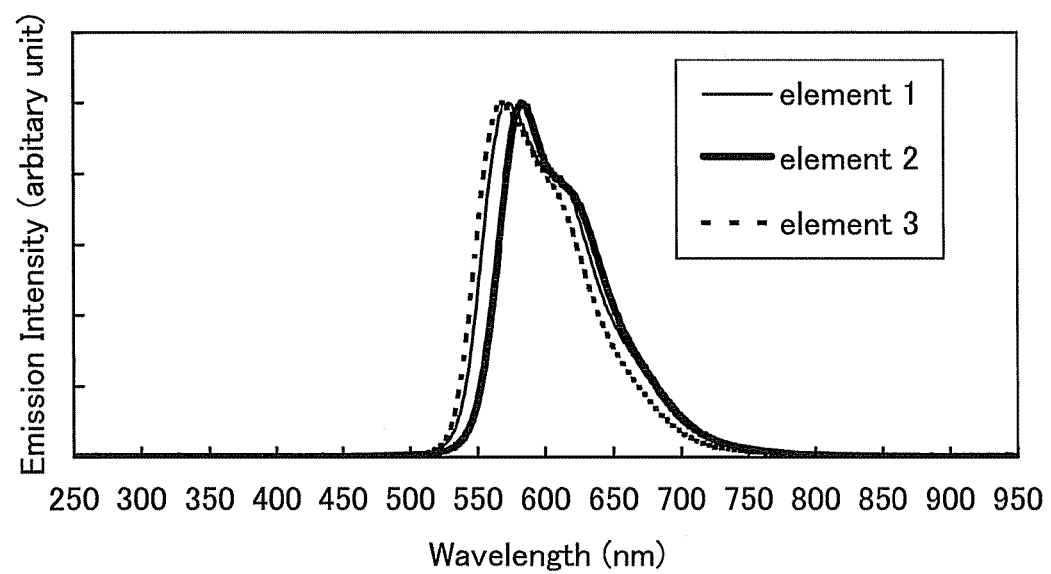
FIG. 16 shows emission spectra of light-emitting elements which are embodiments of the present invention.

FIG. 16 shows emission spectra obtained when current was supplied to the light-emitting elements at a current density of 0.1 mA/cm$^2$. As shown in FIG. 16, the emission spectrum of Light-Emitting Element 1 has a peak at 574 nm, that of Light-Emitting Element 2 has a peak at 583 nm, and that of Light-Emitting Element 3 has a peak at 568 nm. Furthermore, it might be found that the emission spectrum of Light-Emitting Element 1 is obtained from light emission of the organometallic complex which is one embodiment of the present invention ([Ir(dm1nppr)$_2$(acac)]), and the emission spectrum of Light-Emitting Element 2 is obtained from light emission of the organometallic complex which is one embodiment of the present invention ([Ir(dm2nppr)$_2$(acac)]). Light-Emitting Elements 1 and 2 are superior in color purity to Light-Emitting Element 3. Thus, it might be found that a light-emitting element which emits red light with high color purity can be realized by application of one embodiment of the present invention.

In the measurement of the decomposition temperature of [Ir(dm1nppr)$_2$(acac)], the 5% reduction in weight at 350° C.

was observed as described in Example 1. In the measurement of the decomposition temperature of [Ir(dm2nppr)$_2$(acac)], the 5% reduction in weight at 352° C. was observed as described in Example 2. In contrast, [Ir(mppr-iPr)$_2$(acac)], which was used as the light-emitting substance for comparison, showed a 5% reduction in weight at 300° C. Thus, it was found that the organometallic complexes which are embodiments of the present invention were materials having higher heat resistance than [Ir(mppr-iPr)$_2$(acac)] and suitable for use for a light-emitting element.

Example 4

Synthesis Example 3

This example gives descriptions of a method of synthesizing (acetylacetonato)bis[3,5-dimethyl-2-(6-phenylnaphthalen-2-yl)pyrazinato] iridium(III) (abbreviation: [Ir(dm6p2npr)$_2$(acac)]), the organometallic complex represented by Structural Formula (123) in Embodiment 1 which is one embodiment of the present invention. A structure of [Ir(dm6p2npr)$_2$(acac)] is illustrated below.

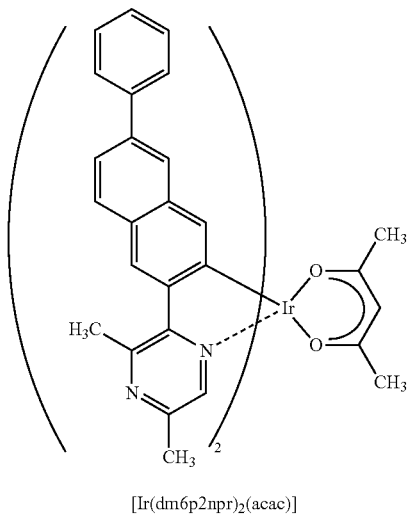

[Ir(dm6p2npr)$_2$(acac)]

Step 1: Synthesis of 6-Bromonaphthalene-2-boronic acid

First, 5.0 g of 2,6-dibromonaphthalene was placed into a 500-mL three-neck flask, and the air in the flask was replaced with nitrogen. To this compound was added 200 mL of tetrahydrofuran (THF), and this solution was stirred at −78° C. for 20 minutes. Then, 12 mL of a 1.7M hexane solution of n-butyllithium (n-BuLi) was dripped into this mixture solution, followed by stirring at −78° C. for 2 hours. After the predetermined time had elapsed, 3.5 mL of trimethyl borate was added to the mixture and this solution was stirred for 18 hours while the temperature was raised to room temperature. After the predetermined time had elapsed, 80 mL of 1.0M hydrochloric acid was poured into this solution, and the mixture was stirred for 1 hour. Then, the mixture solution was separated into an organic layer and an aqueous layer. Organic substances were extracted with ethyl acetate from the obtained aqueous layer. The solution of the extract was combined with the organic layer that had been first obtained, and the mixture was washed with saturated brine and dried by addition of anhydrous magnesium sulfate. Then, the filtrate obtained by gravity filtration was concentrated to give a white solid. The obtained white solid was washed with ethanol, whereby 6-bromonaphthalene-2-boronic acid was obtained (as a white powder in 35% yield). The synthesis scheme of Step 1 is illustrated in the following (a-4).

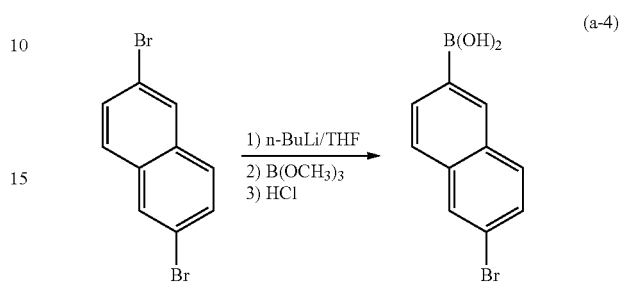

(a-4)

Step 2: Synthesis of 2-Bromo-6-phenylnaphthalene

Next, into a 100-mL three-neck flask were placed 1.5 g of 6-bromonaphthalene-2-boronic acid obtained in the above Step 1, 1.8 g of iodobenzene, and 0.13 g of tri(ortho-tolyl)phosphine (P(o-tolyl)$_3$). To this mixture were added 30 mL of toluene, 10 mL of ethanol, and 10 mL of a 2.0M aqueous potassium carbonate solution. This mixture was degassed under reduced pressure, and the air in the flask was replaced with nitrogen. To this mixture was added 0.015 g of palladium (II) acetate, and the mixture was refluxed under a nitrogen stream at 85° C. for 5 hours. After the reflux, the mixture solution was separated into an organic layer and an aqueous layer, and organic substances were extracted with toluene from the obtained aqueous layer. The solution of the extract was combined with the organic layer that had been first obtained. The resulting mixture was washed with a saturated aqueous solution of sodium hydrogen carbonate and then saturated brine. After the washing, anhydrous magnesium sulfate was added for drying. Then, the filtrate obtained by gravity filtration was concentrated to give a solid. The obtained solid was recrystallized using a mixed solvent of hexane and toluene, whereby 2-bromo-6-phenylnaphthalene was obtained (as a pale yellow solid in 53% yield). The synthesis scheme of Step 2 is illustrated in the following (b-4).

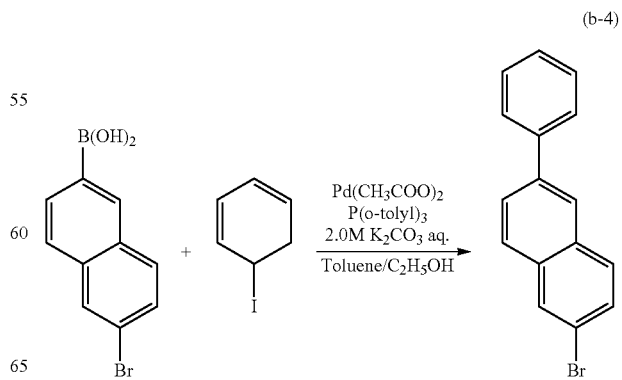

(b-4)

Step 3: Synthesis of 6-Phenylnaphthalene-2-boronic acid

First, 0.9 g of 2-bromo-6-phenylnaphthalene obtained in the above Step 2 was placed into a 200-mL three-neck flask, and the air in the flask was replaced with nitrogen. To this compound was added 100 mL of tetrahydrofuran (THF), and this solution was stirred at −78° C. for 20 minutes. Then, 2.4 mL of a 1.6M hexane solution of n-butyllithium (n-BuLi) was dripped into this solution, followed by stirring at −78° C. for 2 hours. After the predetermined time had elapsed, 0.8 mL of trimethyl borate was added to the mixture and this solution was stirred for 20 hours while the temperature was raised to room temperature. After the predetermined time had elapsed, 60 mL of 1.0M hydrochloric acid was poured into this solution, and the mixture was stirred for 30 minutes. Then, this mixture solution was separated into an organic layer and an aqueous layer. Organic substances were extracted with ethyl acetate from the obtained aqueous layer. The solution of the extract was combined with the organic layer that had been first obtained, and the mixture was washed with saturated brine and dried by addition of anhydrous magnesium sulfate. Then, the filtrate obtained by gravity filtration was concentrated to give a solid. The obtained solid was recrystallized using a mixed solvent of chloroform and hexane, whereby 6-phenylnaphthalene-2-boronic acid was obtained (as a white powder in 55% yield). The synthesis scheme of Step 3 is illustrated in the following (c-4).

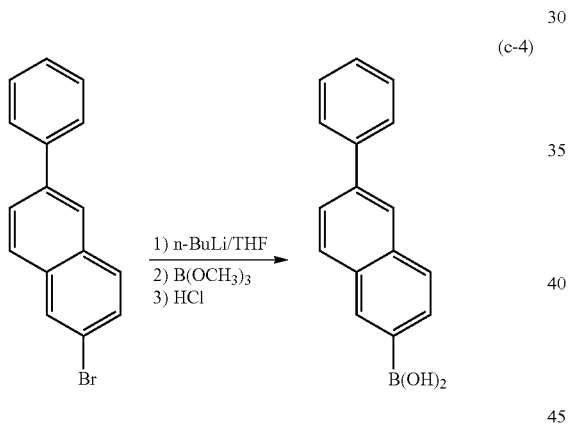

(c-4)

Step 4: Synthesis of 3,5-Dimethyl-2-(6-phenylnaphthalen-2-yl)pyrazine (abbreviation: Hdm6p2npr)

First, into a recovery flask equipped with a reflux pipe were placed 0.24 g of 2-chloro-3,5-dimethylpyrazine, 0.41 g of 6-phenylnaphthalene-2-boronic acid, 0.18 g of sodium carbonate, 0.008 g of bis(triphenylphosphine)palladium(II) dichloride (abbreviation: $Pd(PPh_3)_2Cl_2$), 10 mL of water, and 10 mL of acetonitrile, and the air in the flask was replaced with argon. This reaction container was irradiated with microwaves (2.45 GHz, 100 W) for 30 minutes, so that heating was performed. Then, the reaction container was cooled to 50° C. or less. Water was added to the reaction solution, and the organic layer was extracted with dichloromethane. The obtained organic layer was washed with water and dried with magnesium sulfate. The solution which had been dried was filtered. The solvent of this solution was distilled, whereby Hdm6p2npr, which is the pyrazine derivative to be produced, was obtained (as a white powder in 82% yield). Note that the microwave irradiation was performed using a microwave synthesis system (Discover, manufactured by CEM Corporation). The synthesis scheme of Step 4 is illustrated in the following (d-4).

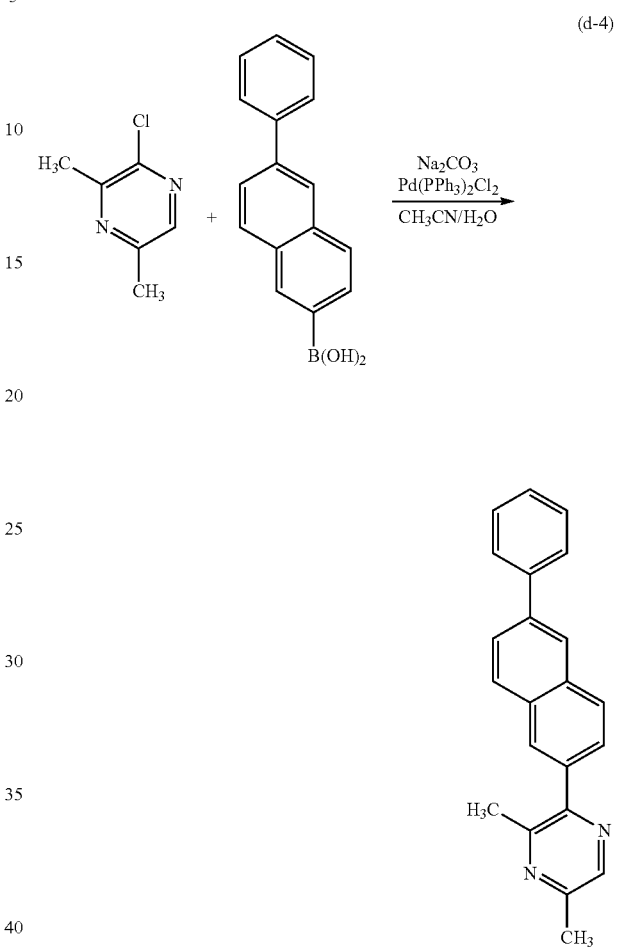

(d-4)

Step 5: Synthesis of Di-µ-chloro-bis[bis{3,5-dimethyl-2-(6-phenylnaphthalen-2-yl)pyrazinato} iridium(III)] (abbreviation: [Ir(dm6p2npr)$_2$Cl]$_2$)

Next, into a recovery flask equipped with a reflux pipe were placed 0.45 g of Hdm6p2npr obtained in the above Step 4, 9 mL of 2-ethoxyethanol, 3 mL of water, and 0.20 g of iridium chloride hydrate ($IrCl_3 \cdot H_2O$) (produced by Sigma-Aldrich Corp.), and the air in the flask was replaced with argon. Then, the mixture was heated by microwave irradiation (2.45 GHz, 100 W) for 90 minutes. Then, the reaction container was cooled to 50° C. or less, and the reaction solution was filtered. The substance obtained by the filtration was washed with ethanol to give a yellowish orange powder of [Ir(dm6p2npr)$_2$Cl]$_2$, which is a binuclear complex (in 69% yield). The synthesis scheme of Step 5 is illustrated in the following (e-4).

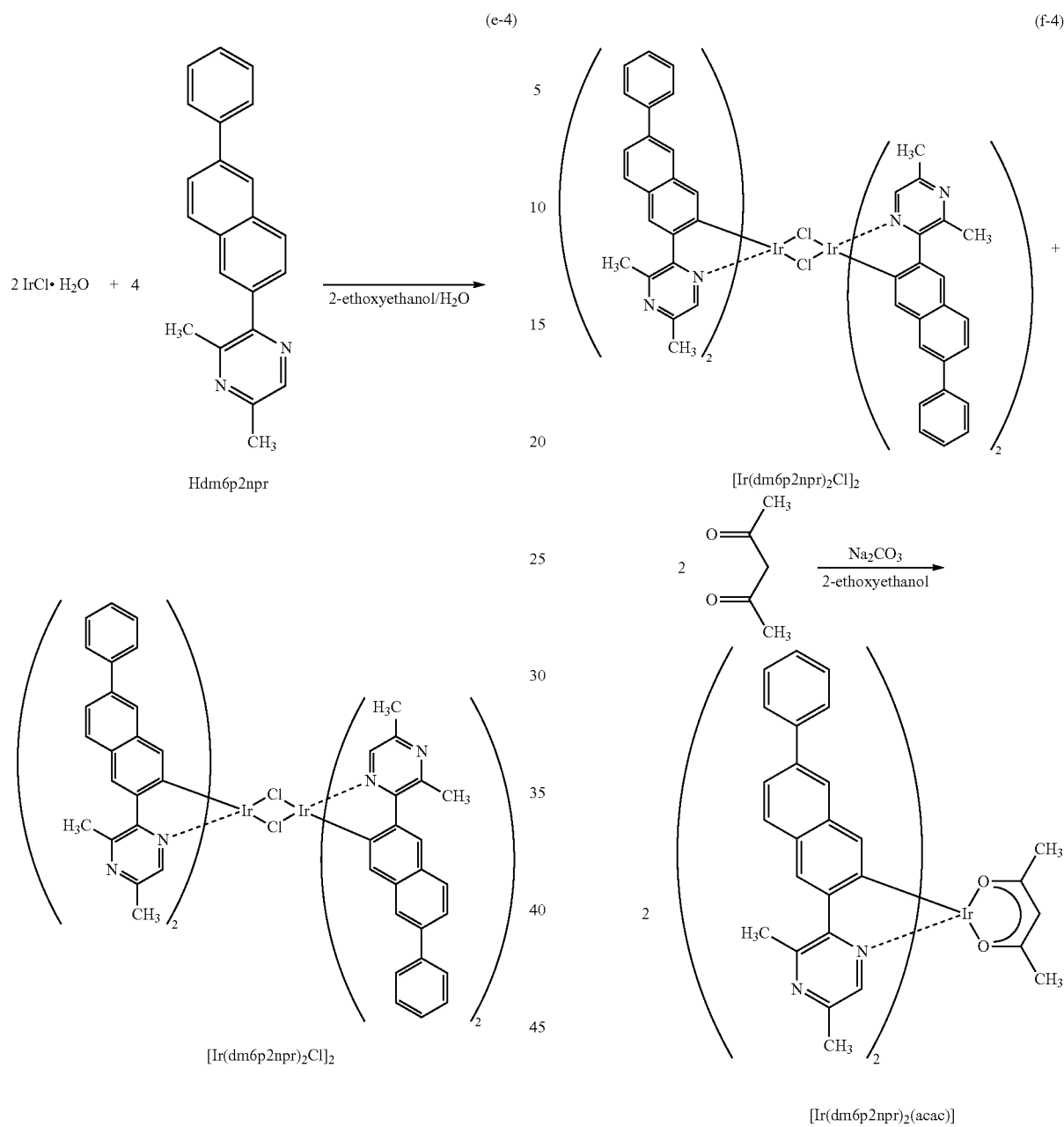

Step 6: Synthesis of (Acetylacetonato)bis[3,5-dimethyl-2-(6-phenylnaphthalen-2-yl)pyrazinato]iridium(III) (abbreviation: [Ir(dm6p2npr)₂(acac)])

Furthermore, into a recovery flask equipped with a reflux pipe were placed 0.39 g of [Ir(dm6p2npr)₂Cl]₂, which is the dinuclear complex obtained in the above Step 5, 15 mL of 2-ethoxyethanol, 0.072 mL of acetylacetone, and 0.24 g of sodium carbonate, and the air in the flask was replaced with argon. Then, the mixture was heated by microwave irradiation (2.45 GHz, 100 W) for 90 minutes. Then, the reaction container was cooled to 50° C. or less, and the reaction solution was filtered. The substance obtained by the filtration was washed sequentially with water, ethanol, acetone, methanol, and ether, whereby an orange powder of the substance to be produced was obtained (in 76% yield). The synthesis scheme of Step 6 is illustrated in the following (f-4).

Figure 17:
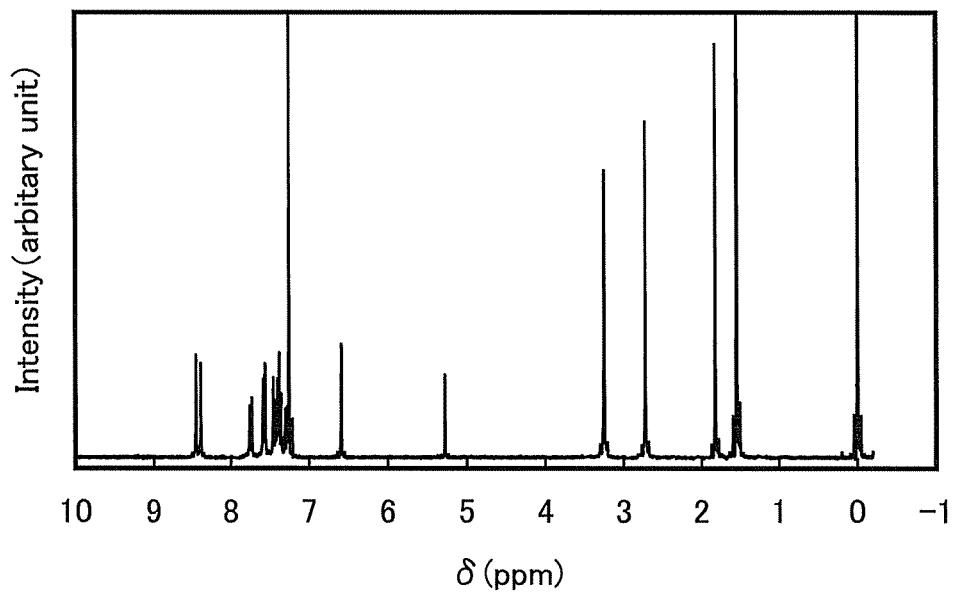
FIG. 17 shows a $^1$H NMR chart of an organometallic complex represented by Structural Formula (123).

The orange powder obtained in the above Step 6 which is the substance to be produced was analyzed by nuclear magnetic resonance (¹H NMR) spectroscopy, results of which are described below. In addition, the ¹H NMR chart is shown in FIG. 17. Thus, [Ir(dm6p2npr)₂(acac)], the above-described organometallic complex represented by Structural Formula (123) which is one embodiment of the present invention, was found to be obtained in this example.

¹NMR. δ (CDCl₃): 1.82 (s, 6H), 2.72 (s, 6H), 3.30 (s, 6H), 5.28 (s, 1H), 6.59 (d, 2H), 7.29 (d, 2H), 7.41 (m, 8H), 7.58 (m, 41), 7.75 (d, 2H), 8.39 (s, 2H), 8.45 (s, 2H).

Figure 18:
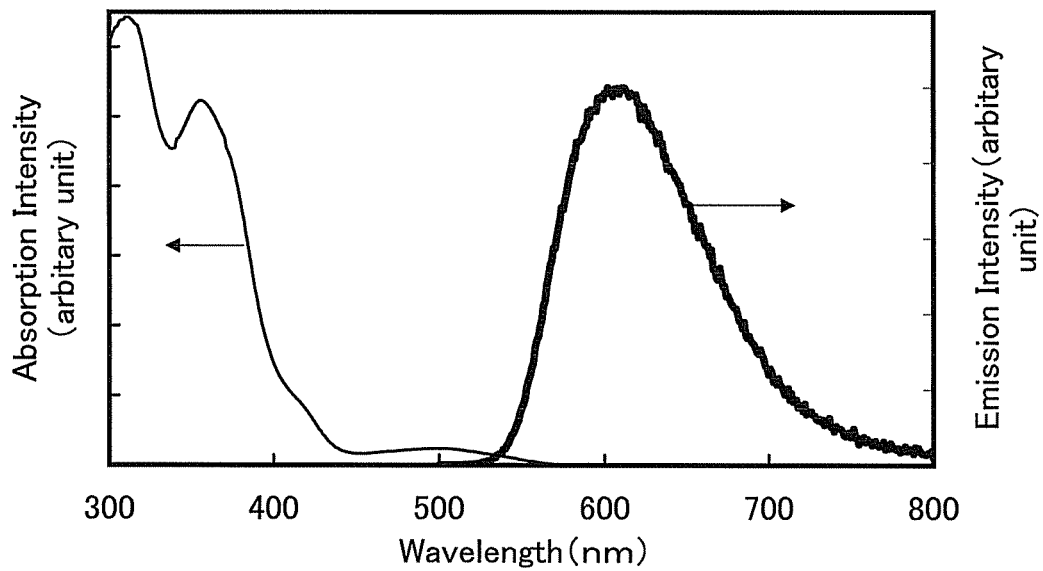
FIG. 18 shows an ultraviolet-visible absorption spectrum and an emission spectrum of an organometallic complex represented by Structural Formula (123).

Next, [Ir(dm6p2npr)₂(acac)] was analyzed by ultraviolet-visible (UV-vis) absorption spectroscopy. A UV-vis spectrum was measured with an ultraviolet-visible spectrophotometer (V-550, manufactured by JASCO Corporation) using a dichloromethane solution (0.051 mmol/L) at room temperature. In addition, measurement of an emission spectrum of [Ir(dm6p2npr)₂(acac)] was carried out. The emission spectrum was measured with a fluorescence spectrophotometer (FS920, manufactured by Hamamatsu Photonics Corporation) using a degassed dichloromethane solution (0.31 mmol/L) at room temperature. FIG. 18 shows results of the measurements, in which the horizontal axis represents wavelength (nm) and the vertical axis represents absorption intensity (arbitrary unit) and emission intensity (arbitrary unit).

As shown in FIG. 18, [Ir(dm6p2npr)₂(acac)], the organometallic complex which is one embodiment of the present invention, has an emission peak at 611 nm, and reddish orange light was observed from the dichloromethane solution.

The decomposition temperature of [Ir(dm6p2npr)₂(acac)], the obtained organometallic complex which is one embodiment of the present invention, was measured with a high vacuum differential type differential thermal balance (TG-DTA2410SA, manufactured by Bruker AXS K.K.). The temperature was increased at a temperature increase rate of 10° C./min, whereby a 5% reduction in weight was observed at 348° C., which is indicative of high heat resistance.

Example 5

This example gives description of a light-emitting element (Light-Emitting Element 4) including [Ir(dm6p2npr)₂(acac)] (Structural Formula (123)), the organometallic complex which is one embodiment of the present invention and was synthesized in Example 4, as a light-emitting substance. Further, the description contains a reference light-emitting element (Light-Emitting Element 5) including (acetylacetonato)bis[2-(2-naphthyl)-3,5-dimethylpyrazinato]iridium(III) (abbreviation: [Ir(dm2npr)₂(acac)]), which is a substance represented by Structural Formula (vi) below, as a light-emitting substance.

Note that illustration of the organic compounds used in this example described in Example 3 will be omitted here. In addition, a structure of the light-emitting element of the present invention will be described on the basis of FIG. 11.

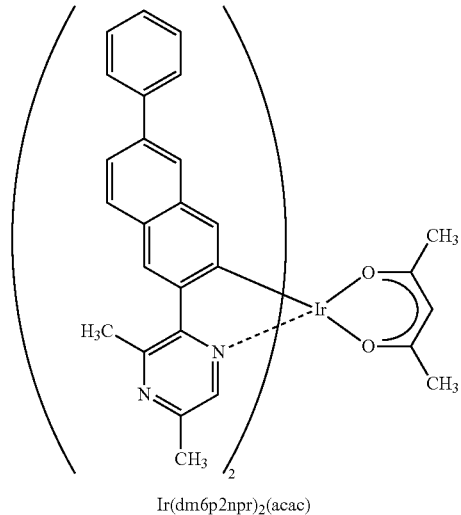

Ir(dm6p2npr)₂(acac)

(123)

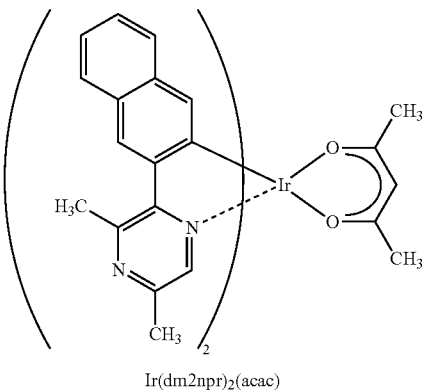

Ir(dm2npr)₂(acac)

(vi)

[Formation of Light-Emitting Elements 4 and 5]

First, as the first electrode 1101, an ITSO film is formed to a thickness of 110 nm over a substrate 1100 made of glass. Note that a surface of the ITSO film is covered with an insulating film so that a 2 mm square portion of the surface is exposed. Here, the first electrode 1101 is an electrode that functions as an anode of the light-emitting element.

Next, as pretreatment for forming the light-emitting elements over the substrate 1100, a surface of the substrate was washed with water, baked at 200° C. for 1 hour, and subjected to UV ozone treatment for 370 seconds.

After that, the substrate was transferred into a vacuum evaporation apparatus in which the pressure had been reduced to approximately 10⁻⁴ Pa, and subjected to vacuum baking at 170° C. for 30 minutes in a heating chamber of the vacuum evaporation apparatus. Then, the substrate 1100 was cooled down for about 30 minutes.

Next, the substrate 1100 was fixed to a holder provided in the vacuum evaporation apparatus so that the surface of the substrate 1100 on which the first electrode 1101 was formed faced downward. In the case described in this example, the hole-injection layer 1111, the hole-transport layer 1112, the light-emitting layer 1113, the electron-transport layer 1114, and the electron-injection layer 1115 which are included in the EL layer 1102 are sequentially formed.

After the pressure in the vacuum evaporation apparatus was reduced to about 10⁻⁴ Pa, BPAFLP represented by the above Structural Formula (ii) and molybdenum oxide were co-evaporated with a mass ratio of BPAFLP to molybdenum oxide being 4:2, whereby the hole-injection layer 1111 was formed. The thickness thereof was 50 nm.

Next, BPAFLP was evaporated to a thickness of 10 nm, whereby the hole-transport layer 1112 was formed.

Next, the light-emitting layer 1113 was formed over the hole-transport layer 1112. For Light-Emitting Element 4, Cz1PQ-III represented by the above Structural Formula (iii), PCBA1BP represented by the above Structural Formula (Iv), and [Ir(dm6p2npr)₂(acac)] represented by the above Structural Formula (123) were co-evaporated over the hole-transport layer 1112 with a mass ratio of Cz1PQ-III:PCBA1BP:[Ir(dm6p2npr)₂(acac)] being 1:0.5:0.1. For Light-Emitting Element 5, Cz1PQ-III, PCBA1BP, and [Ir(dm2npr)₂(acac)] represented by the above Structural Formula (vi) were co-evaporated over the hole-transport layer 1112 with a mass ratio of Cz1PQ-III:PCBA1BP [Ir(dm2npr)₂(acac)] being 1:0.5:0.1. Thus, each light-emitting layer 1113 was formed. The thickness of each light-emitting layer was 40 nm.

Next, Cz1PQ-III represented by the above Structural Formula (iii) was evaporated to a thickness of 10 nm and then BPhen represented by the above Structural Formula (v) was evaporated to a thickness of 20 nm, whereby the electron-transport layer 1114 was formed. Furthermore, lithium fluoride was evaporated to a thickness of 2 nm over the electron-transport layer 1114, whereby the electron-injection layer 1115 was formed.

Next, an aluminum film was formed to a thickness of 200 nm as the second electrode 1103. Thus, Light-Emitting Elements 4 and 5 were obtained. Note that the second electrode 1103 is an electrode that functions as a cathode. Note that in all of the above evaporation steps, a resistance heating method was adopted.

Further, these light-emitting elements were sealed in a glove box under a nitrogen atmosphere to prevent from being exposed to the atmosphere.

[Operation Characteristics of Light-Emitting Elements 4 and 5]

Operation characteristics of the formed light-emitting elements (Light-Emitting Elements 4 and 5) were measured. Note that the measurements were carried out at room temperature (in an atmosphere kept at 25° C.).

Figure 19:
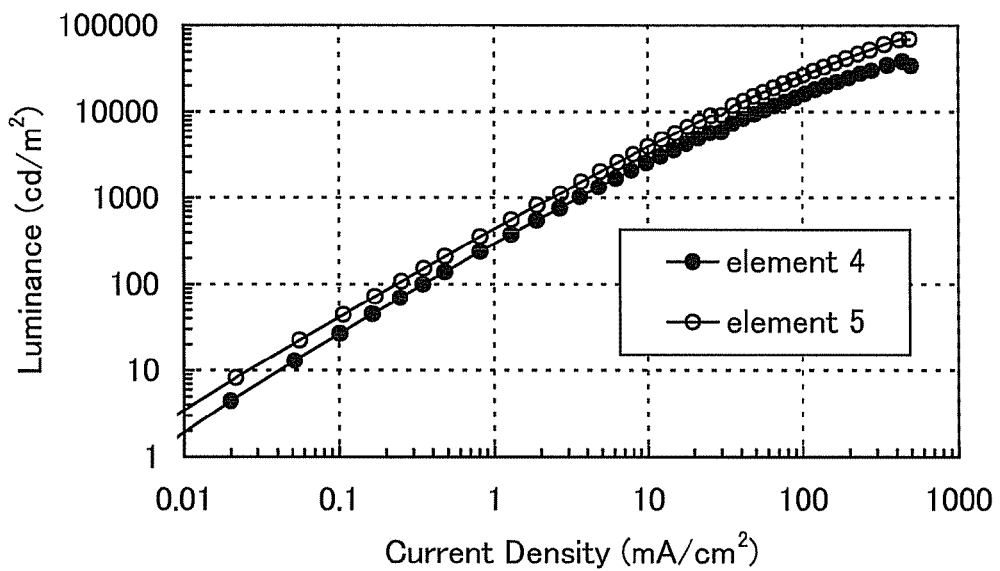
FIG. 19 shows current density versus luminance characteristics of light-emitting elements which are embodiments of the present invention.
Figure 20:
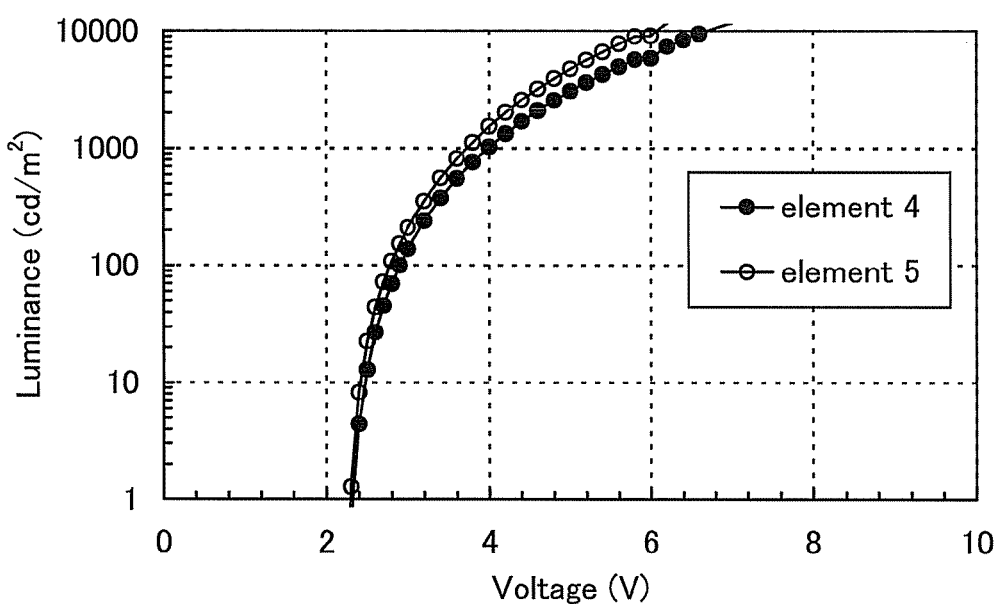
FIG. 20 shows voltage versus luminance characteristics of light-emitting elements which are embodiments of the present invention.

FIG. 19 shows current density versus luminance characteristics of the light-emitting elements. In FIG. 19, the vertical axis represents luminance (cd/m$^2$) and the horizontal axis represents current density (mA/cm$^2$). FIG. 20 shows voltage versus luminance characteristics of the light-emitting elements. In FIG. 20, the vertical axis represents luminance (cd/m$^2$) and the horizontal axis represents voltage (V).

Figure 21:
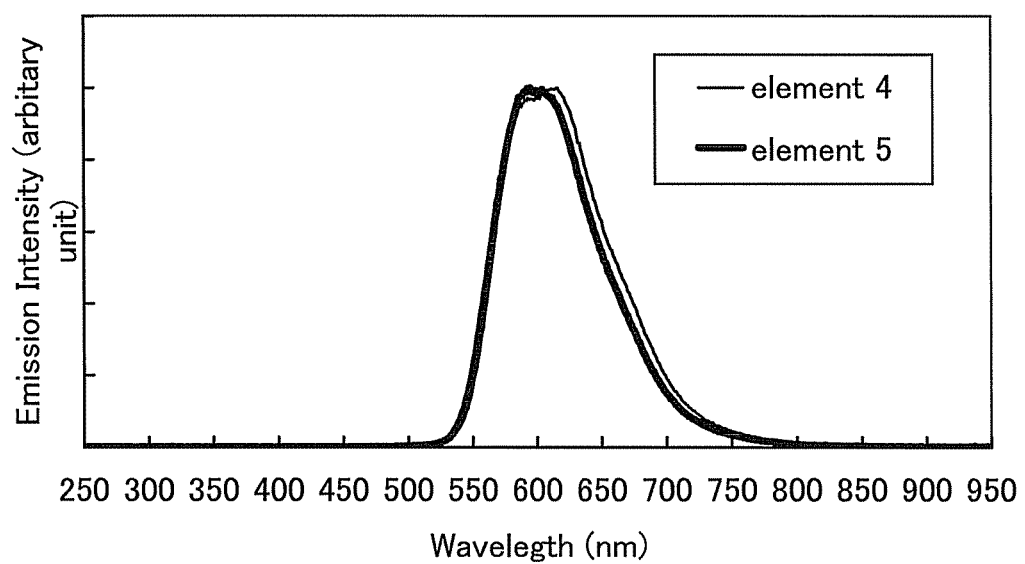
FIG. 21 shows emission spectra of light-emitting elements which are embodiments of the present invention.

FIG. 21 shows emission spectra obtained when current was supplied to the light-emitting elements at a current density of 0.1 mA/cm$^2$. As shown in FIG. 21, the emission spectrum of Light-Emitting Element 4 has a peak at 616 nm, and that of Light-Emitting Element 5 has a peak at 595 nm. Furthermore, it might be found that the emission spectrum of Light-Emitting Element 4 is obtained from light emission of the organometallic complex which is one embodiment of the present invention ([Ir(dm6p2npr)$_2$(acac)]). Light-Emitting Element 4 is superior in color purity to Light-Emitting Element 5. Thus, it might be found that a light-emitting element which emits red light with high color purity can be realized by application of one embodiment of the present invention.

In the measurement of the decomposition temperature of [Ir(dm6p2npr)$_2$(acac)], the 5% reduction in weight at 348° C. was observed as described in Example 4. In contrast, [Ir(dm2npr)$_2$(acac)], the light-emitting substance used for Light-Emitting Element 5 which is a reference light-emitting element, showed a 5% reduction in weight at 347° C.

Example 6

Synthesis Example 4

This example gives descriptions of a method of synthesizing (acetylacetonato)bis[3,5-dimethyl-2-(7-phenylnaphthalen-2-yl)pyrazinato] iridium(III) (abbreviation: [Ir(dm7p2npr)$_2$(acac)]), the organometallic complex represented by Structural Formula (126) in Embodiment 1 which is one embodiment of the present invention. A structure of [Ir(dm7p2npr)$_2$(acac)] is illustrated below.

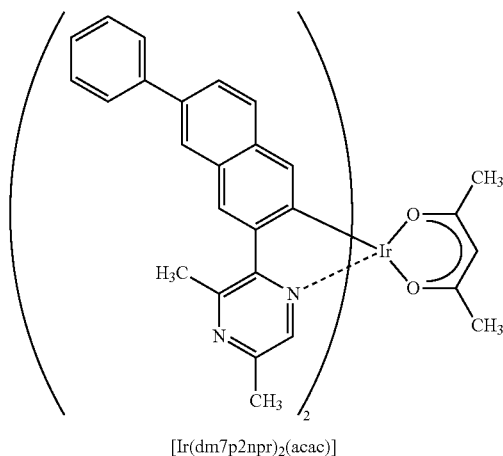

[Ir(dm7p2npr)$_2$(acac)]

Step 1: Synthesis of 7-Bromonaphthalene-2-boronic acid

First, 3.0 g of 2,7-dibromonaphthalene was placed into a 500-mL three-neck flask, and the air in the flask was replaced with nitrogen. To this compound was added 150 mL of tetrahydrofuran (THF), and this solution was stirred at −78° C. for 20 minutes. Then, 6.4 mL of a 1.7M hexane solution of n-butyllithium (n-BuLi) was dripped into this mixture solution, followed by stirring at −78° C. for 2 hours. After the predetermined time had elapsed, 2.4 mL of trimethyl borate was added to the mixture and this solution was stirred for 18 hours while the temperature was raised to room temperature. After the predetermined time had elapsed, 60 mL of 1.0M hydrochloric acid was poured into this solution, and the mixture was stirred for 1 hour. Then, this mixture solution was separated into an organic layer and an aqueous layer. Organic substances were extracted with ethyl acetate from the obtained aqueous layer. The solution of the extract was combined with the organic layer that had been first obtained, and the mixture was washed with saturated brine and dried by addition of anhydrous magnesium sulfate to the organic layer. Then, the filtrate obtained by gravity filtration was concentrated to give a white solid. The obtained white solid was washed with a mixed solvent of hexane and toluene, whereby 7-bromonaphthalene-2-boronic acid was obtained (as a white powder in 75% yield). The synthesis scheme of Step 1 is illustrated in the following (a-5).

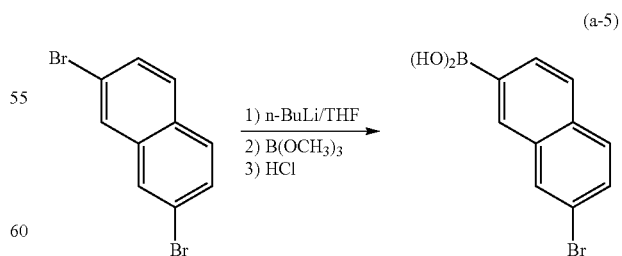

(a-5)

Step 2: Synthesis of 2-Bromo-7-phenylnaphthalene

Next, into a 100-mL three-neck flask were placed 2.0 g of 7-bromonaphthalene-2-boronic acid obtained in the above Step 1, 3.3 g of iodobenzene, and 0.17 g of tri(ortho-tolyl) phosphine (P(o-tolyl)₃). To this mixture were added 30 mL of toluene, 6 mL of ethanol, and 10 mL of a 2.0M aqueous potassium carbonate solution. This mixture was degassed under reduced pressure, and the air in the flask was replaced with nitrogen. To this mixture was added 0.024 g of palladium (II) acetate, and the mixture was refluxed under a nitrogen stream at 90° C. for 6 hours. After the reflux, the mixture solution was separated into an organic layer and an aqueous layer, and organic substances were extracted with toluene from the obtained aqueous layer. The solution of the extract was combined with the organic layer that had been first obtained. The resulting mixture was washed with a saturated aqueous solution of sodium hydrogen carbonate and then saturated brine. After the washing, anhydrous magnesium sulfate was added to the organic layer for drying. Then, the filtrate obtained by gravity filtration was concentrated to give a solid. The obtained solid was recrystallized using a mixed solvent of hexane and toluene, whereby 2-bromo-7-phenyl-naphthalene was obtained (as a white solid in 45% yield). The synthesis scheme of Step 2 is illustrated in the following (b-5).

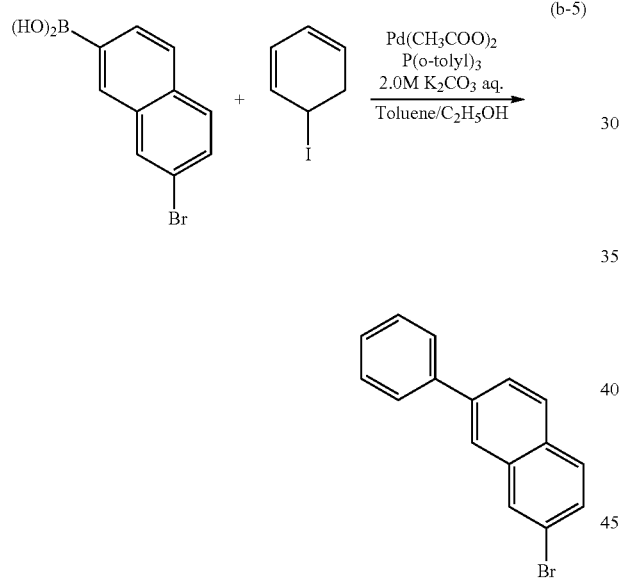

Step 3: Synthesis of 7-Phenylnaphthalene-2-boronic acid

First, 4.5 g of 2-bromo-7-phenylnaphthalene obtained in the above Step 2 was placed into a 300-mL three-neck flask, and the air in the flask was replaced with nitrogen. To this compound was added 100 mL of tetrahydrofuran (THF), and this solution was stirred at −78° C. for 20 minutes. Then, 11 mL of a 1.7M hexane solution of n-butyllithium (n-BuLi) was dripped into this solution, followed by stirring at −78° C. for 2 hours. After the predetermined time had elapsed, 3.5 mL of trimethyl borate was added to the mixture and this solution was stirred for 24 hours while the temperature was raised to room temperature. After the predetermined time had elapsed, 80 mL of 1.0 M hydrochloric acid was poured into this solution, and the mixture was stirred for 1 hour. Then, this mixture solution was separated into an organic layer and an aqueous layer. Organic substances were extracted with ethyl acetate from the obtained aqueous layer. The solution of the extract was combined with the organic layer that had been first obtained, and the mixture was washed with saturated brine and dried by addition of anhydrous magnesium sulfate to the organic layer. Then, the filtrate obtained by gravity filtration was concentrated to give a solid. The obtained solid was recrystallized with a mixed solvent of chloroform and hexane, whereby 7-phenylnaphthalene-2-boronic acid was obtained (as a white powder in 62% yield). The synthesis scheme of Step 3 is illustrated in the following (c-5).

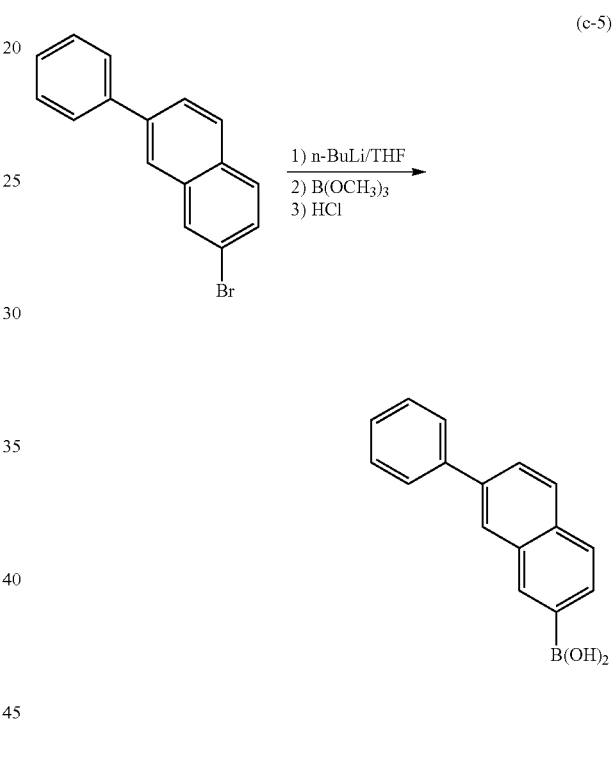

Step 4: Synthesis of 3,5-Dimethyl-2-(7-phenylnaphthalen-2-yl)pyrazine (abbreviation: Hdm7p2npr)

First, into a recovery flask equipped with a reflux pipe were placed 0.62 g of 2-chloro-3,5-dimethylpyrazine, 1.07 g of 7-phenylnaphthalene-2-boronic acid, 0.46 g of sodium carbonate, 0.020 g of bis(triphenylphosphine)palladium(II) dichloride (abbreviation: Pd(PPh₃)₂Cl₂), 10 mL of water, and 10 mL of acetonitrile, and the air in the flask was replaced with argon. This reaction container was irradiated with microwaves (2.45 GHz, 100 W) for 15 minutes, so that heating was performed. Then, the reaction container was cooled to 50° C. or less. Water was added to the reaction solution, and the organic layer was extracted with dichloromethane. The obtained organic layer was washed with water and dried with magnesium sulfate. The solution which had been dried was filtered. The solvent of this solution was distilled, and the obtained residue was purified by silica gel column chromatography with a developing solvent of dichloromethane, whereby Hdm7p2npr, which is the pyrazine derivative to be produced, was found to be obtained (as a white powder in 65% yield). Note that the microwave irradiation was performed using a microwave synthesis system (Discover, manufactured by CEM Corporation). The synthesis scheme of Step 4 is illustrated in the following (d-5).

(d-5)

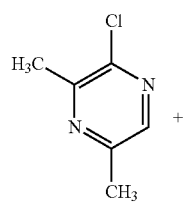

+

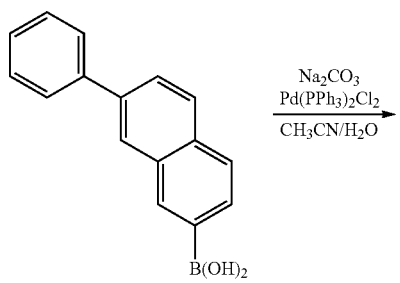

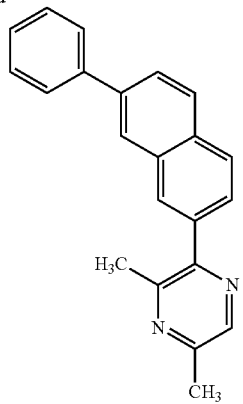

Hdm7p2npr

Step 5: Synthesis of Di-µ-chloro-bis[bis{3,5-dimethyl-2-(7-phenylnaphthalen-2-yl)pyrazinato} iridium (III)] (abbreviation: [Ir(dm7p2npr)$_2$Cl]$_2$)

Next, into a recovery flask equipped with a reflux pipe were placed 12 mL of 2-ethoxyethanol, 4 mL of water, 0.87 g of Hdm7p2npr obtained in the above Step 4, and 0.40 g of iridium chloride hydrate (IrCl$_3$.H$_2$O) (produced by Sigma-Aldrich Corp.), and the air in the flask was replaced with argon. Then, the mixture was heated by microwave irradiation (2.45 GHz, 100 W) for 30 minutes. Then, the reaction container was cooled to 50° C. or less, and the reaction solution was filtered. The substance obtained by the filtration was washed with ethanol to give an orange powder of [Ir(dm7p2npr)$_2$Cl]$_2$, which is a binuclear complex (in 78% yield). The synthesis scheme of Step 5 is illustrated in the following (e-5).

(e-5)

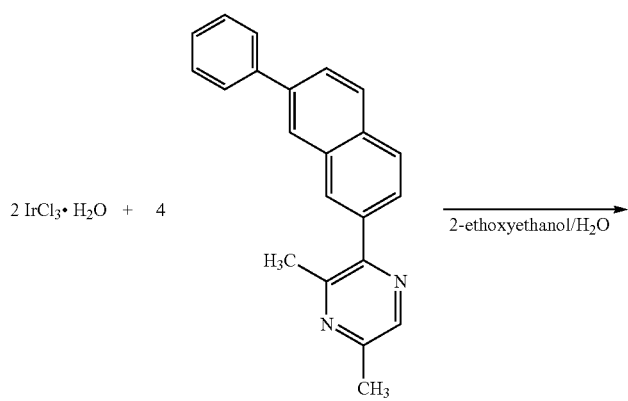

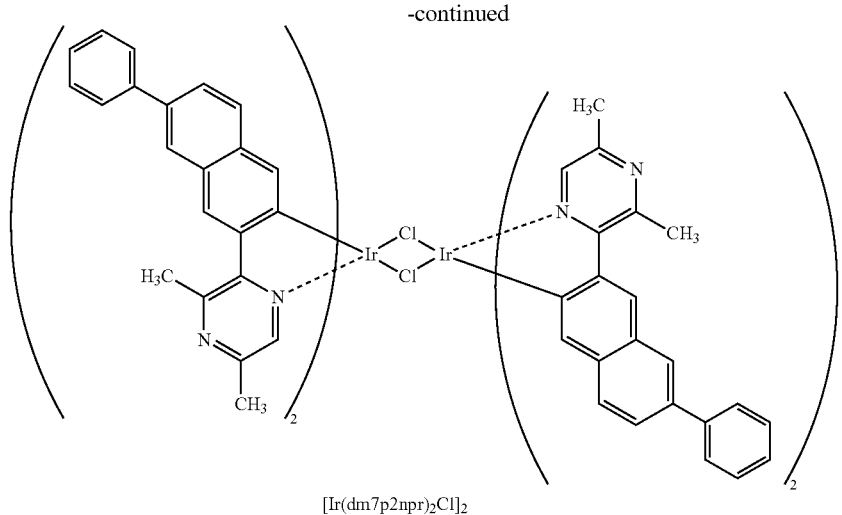

[Ir(dm7p2npr)₂Cl]₂

Step 6: Synthesis of (Acetylacetonato)bis[3,5-dimethyl-2-(7-phenylnaphthalen-2-yl)pyrazinato] iridium(III) (abbreviation: [Ir(dm7p2npr)₂(acac)])

Furthermore, into a recovery flask equipped with a reflux pipe were placed 0.86 g of [Ir(dm7p2npr)₂Cl]₂, which is the dinuclear complex obtained in the above Step 5, 15 mL of 2-ethoxyethanol, 0.16 mL of acetylacetone, and 0.54 g of sodium carbonate, and the air in the flask was replaced with argon. Then, the mixture was heated by microwave irradiation (2.45 GHz, 100 W) for 30 minutes. Then, the reaction container was cooled to 50° C. or less, and the reaction solution was filtered. The substance obtained by the filtration was washed with water and then ethanol, and recrystallized using dichloromethane, whereby an orange powder of the substance to be produced was obtained (in 2% yield). The synthesis scheme of Step 6 is illustrated in the following (f-5).

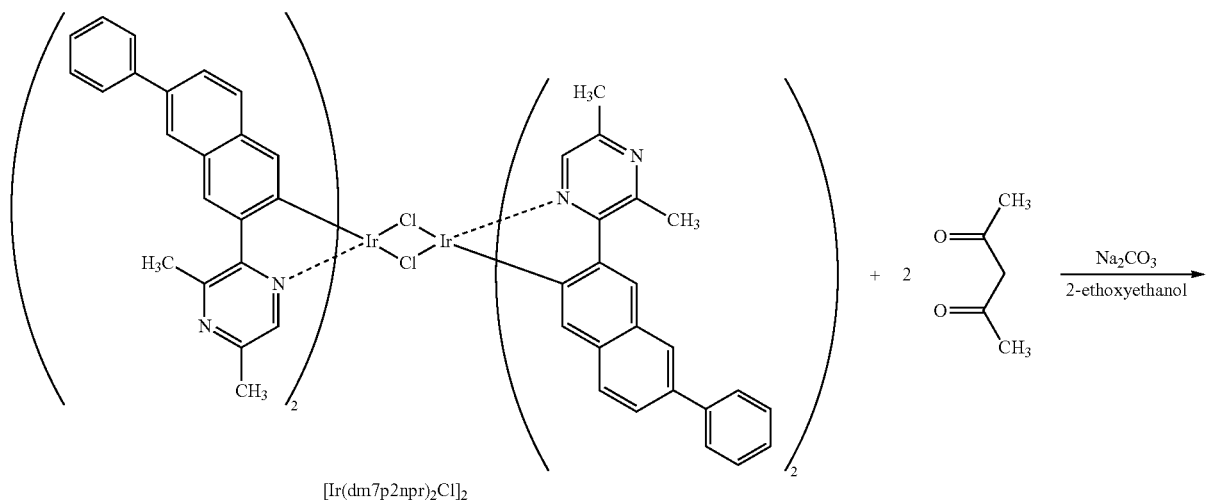

(f-5)

[Ir(dm7p2npr)₂Cl]₂

-continued

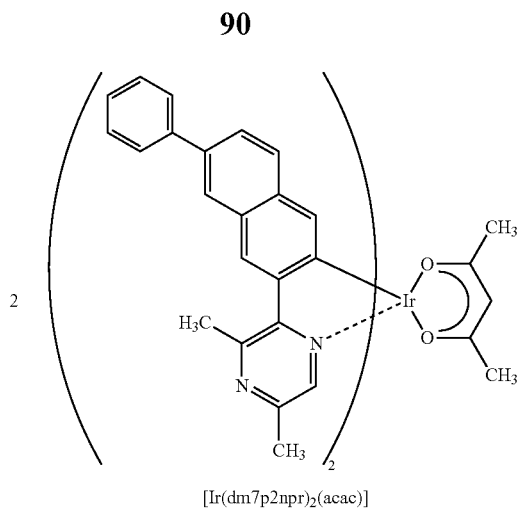

[Ir(dm7p2npr)₂(acac)]

Figure 22:
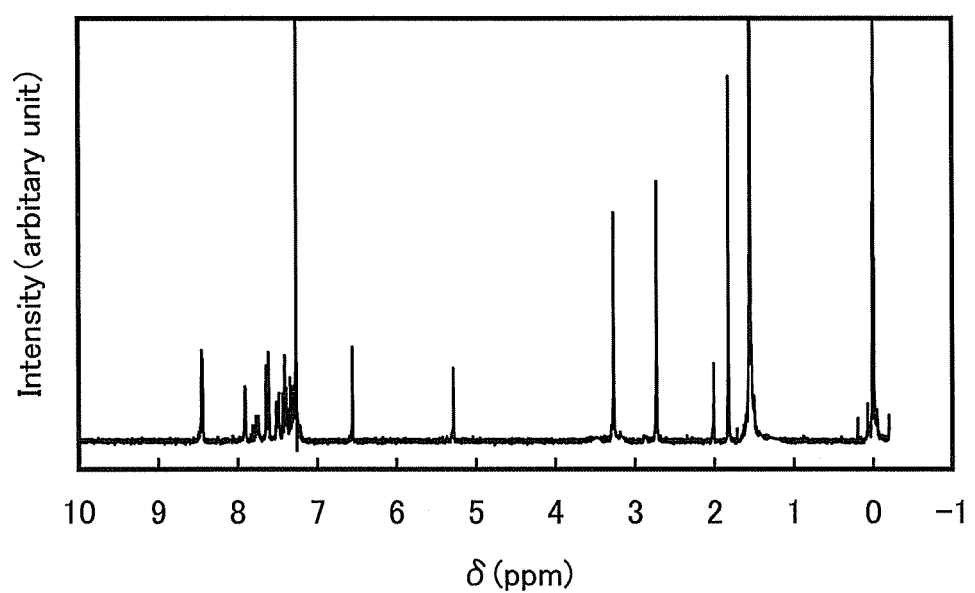
FIG. 22 shows a $^1$H NMR chart of an organometallic complex represented by Structural Formula (126).

The orange powder obtained in the above Step 6 was analyzed by nuclear magnetic resonance (¹H NMR) spectroscopy, results of which are described below. In addition, the ¹H NMR chart is shown in FIG. 22. Thus, [Ir(dm7p2npr)₂(acac)], the above-described organometallic complex represented by Structural Formula (126) which is one embodiment of the present invention, was found to be obtained in this example.

¹H NMR. δ (CDCl₃): 1.83 (s, 6H), 2.73 (s, 6H), 3.27 (s, 6H), 5.28 (s, 1H), 6.56 (s, 2H), 7.31 (m, 2H), 7.41 (m, 4H), 7.49 (m, 2H), 7.62 (m, 4H), 7.75 (m, 2H), 7.91 (m, 2H), 8.45 (d, 4H).

Figure 23:
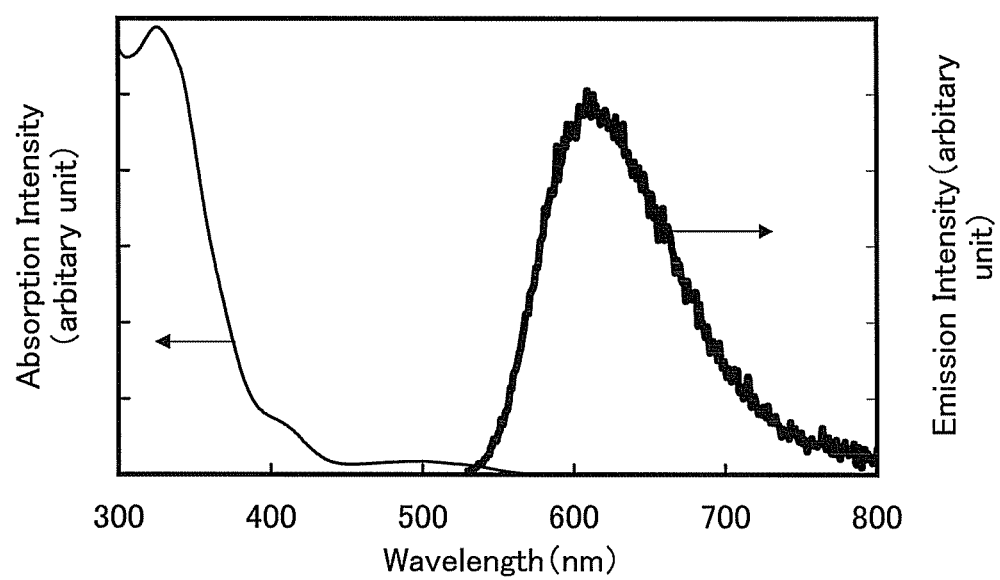
FIG. 23 shows an ultraviolet-visible absorption spectrum and an emission spectrum of an organometallic complex represented by Structural Formula (126).

Next, [Ir(dm7p2npr)₂(acac)] was analyzed by ultraviolet-visible (UV-vis) absorption spectroscopy. A UV-vis spectrum was measured with an ultraviolet-visible spectrophotometer (V-550, manufactured by JASCO Corporation) using a dichloromethane solution (0.045 mmol/L) at room temperature. In addition, measurement of an emission spectrum of [Ir(dm7p2npr)₂(acac)] was carried out. The emission spectrum was measured with a fluorescence spectrophotometer (FS920, manufactured by Hamamatsu Photonics Corporation) using a degassed dichloromethane solution (0.28 mmol/L) at room temperature. FIG. 23 shows results of the measurements, in which the horizontal axis represents wavelength (nm) and the vertical axis represents absorption intensity (arbitrary unit) and emission intensity (arbitrary unit).

As shown in FIG. 23, [Ir(dm7p2npr)₂(acac)], the organometallic complex which is one embodiment of the present invention, has an emission peak at 610 nm, and reddish orange light was observed from the dichloromethane solution.

The decomposition temperature of [Ir(dm7p2npr)₂(acac)], the obtained organometallic complex which is one embodiment of the present invention, was measured with a high vacuum differential type differential thermal balance (TG-DTA2410SA, manufactured by Bruker AXS K.K.). The temperature was increased at a temperature increase rate of 10° C./min, whereby a 5% reduction in weight was observed at 375° C. It was understood that [Ir(dm7p2npr)₂(acac)] described in this example had especially high heat resistance.

Reference Example 1

A method of synthesizing 4-phenyl-4'-(9-phenylfluoren-9-yl)triphenylamine (abbreviation: BPAFLP) used in the above Examples will be specifically described. A structure of BPAFLP is illustrated below.

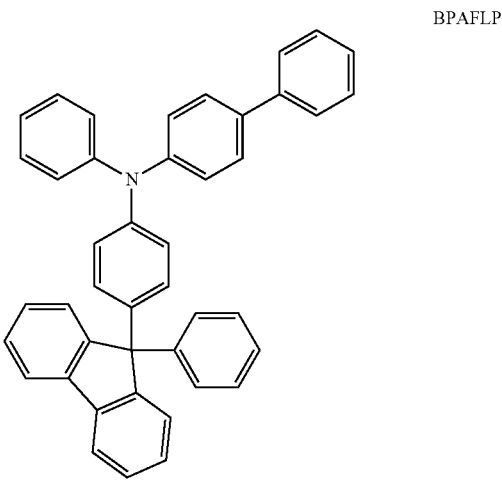 [SMILES: c1ccc(-c2ccc(N(c3ccccc3)c3ccc(C4(c5ccccc5)c5ccccc5-c5ccccc54)cc3)cc2)cc1]

BPAFLP

Step 1: Method of Synthesizing
9-(4-Bromophenyl)-9-phenylfluorene

In a 100-mL three-neck flask, 1.2 g (50 mmol) of magnesium was heated and stirred under reduced pressure for 30 minutes, and was activated. The magnesium was cooled to room temperature, and a nitrogen atmosphere was formed in the flask. Then, several drops of dibromoethane were added, so that foam formation and heat generation were confirmed. After 12 g (50 mmol) of 2-bromobiphenyl dissolved in 10 mL of diethyl ether was slowly dripped into this mixture, the mixture was heated and stirred under reflux for 2.5 hours, whereby a Grignard reagent was prepared.

Into a 500-mL three-neck flask were placed 10 g (40 mmol) of 4-bromobenzophenone and 100 mL of diethyl ether. After the Grignard reagent which was synthesized in advance was slowly dripped into this mixture, the mixture was heated and stirred under reflux for 9 hours.

After reaction, this mixture solution was filtered to give a residue. The obtained residue was dissolved in 150 mL of ethyl acetate, and 1N-hydrochloric acid was added to the mixture until it was made acid, which was then stirred for 2 hours. The organic layer of this liquid was washed with water, and magnesium sulfate was added thereto to remove moisture. This suspension was filtered, and the obtained filtrate was concentrated to give a highly viscous substance.

Into a 500-mL recovery flask were placed this highly viscous substance, 50 mL of glacial acetic acid, and 1.0 mL of hydrochloric acid. The mixture was stirred and heated at 130° C. for 1.5 hours under a nitrogen atmosphere to be reacted.

After the reaction, this reaction mixture solution was filtrated to give a residue. The obtained residue was washed sequentially with water, an aqueous sodium hydroxide solution, water, and methanol in this order. Then, the mixture was dried to give 11 g of a white powder in 69% yield, which is the substance to be produced. A reaction scheme of the above synthesis method is illustrated in the following (J-1).

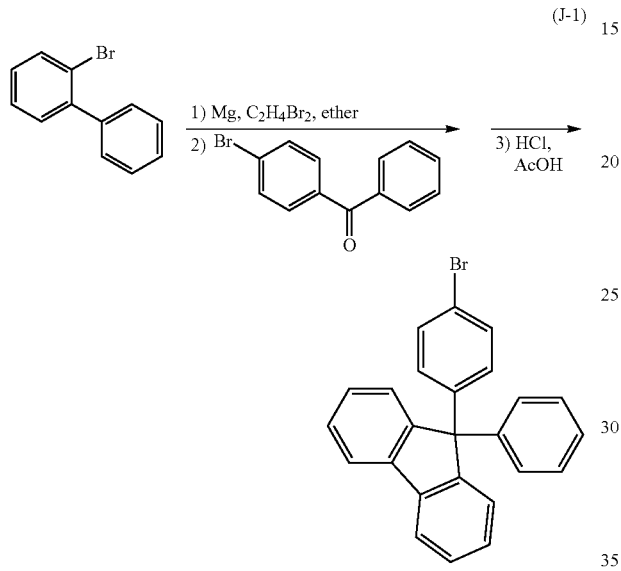

(J-1)

Step 2: Method of Synthesizing 4-Phenyl-4'-(9-phenylfluoren-9-yl)triphenylamine (abbreviation: BPAFLP)

Into a 100-mL three-neck flask were placed 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0), and the air in the flask was replaced with nitrogen. Then, 20 mL of dehydrated xylene was added to this mixture. After the mixture was degassed by stirring under reduced pressure, 0.2 mL (0.1 mmol) of tri(tert-butyl)phosphine (a 10 wt % hexane solution) was added to the mixture. This mixture was stirred and heated at 110° C. for 2 hours under a nitrogen atmosphere, and was reacted.

After the reaction, 200 mL of toluene was added to this reaction mixture solution, and this suspension was filtrated through Florisil (produced by Wako Pure Chemical Industries, Ltd., Catalog No. 540-00135) and Celite (produced by Wako Pure Chemical Industries, Ltd., Catalog No. 531-16855). The obtained filtrate was concentrated, and the resulting substance was purified by silica gel column chromatography (with a developing solvent of toluene and hexane in a 1:4 ratio). The obtained fractions were concentrated, and acetone and methanol were added to the mixture. The mixture was irradiated with ultrasonic waves and then recrystallized to give 4.1 g of a white powder in 92% yield, which is the substance to be produced. A reaction scheme of the above synthesis method is illustrated in the following (J-2).

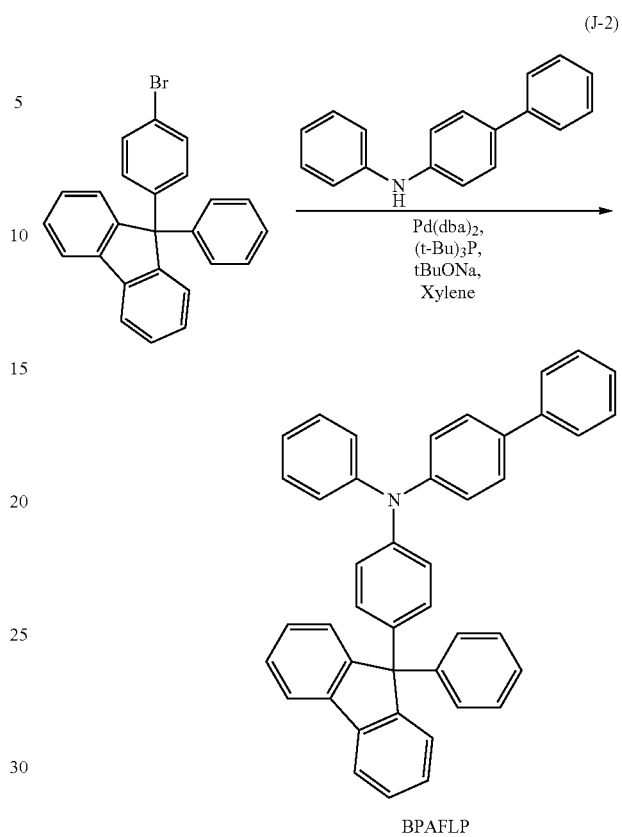

(J-2)

The Rf values of the substance to be produced, 9-(4-bromophenyl)-9-phenylfluorene, and 4-phenyl-diphenylamine were respectively 0.41, 0.51, and 0.27, which were found by silica gel thin layer chromatography (TLC) (with a developing solvent of ethyl acetate and hexane in a 1:10 ratio).

The compound obtained by the above Step 2 was subjected to a nuclear magnetic resonance (NMR) method. The measurement data are shown below. The measurement results indicate that the obtained compound was BPAFLP, which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

This application is based on Japanese Patent Application serial no. 2010-087626 filed with the Japan Patent Office on Apr. 6, 2010, the entire contents of which are hereby incorporated by reference.

What is claimed is:
1. A complex including a structure represented by Formula (G1),

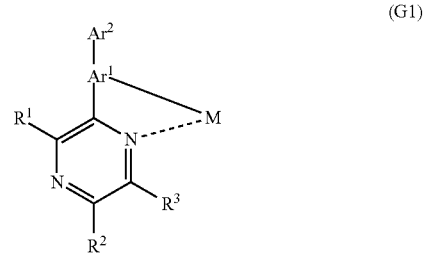

(G1)

wherein:
- $R^1$ represents any of an alkyl group having 1 to 4 carbon atoms, an alkoxy group having 1 to 4 carbon atoms, and an alkylthio group having 1 to 4 carbon atoms;
- $R^2$ represents any of hydrogen, an alkyl group having 1 to 4 carbon atoms, an alkoxy group having 1 to 4 carbon atoms, and an alkylthio group having 1 to 4 carbon atoms;
- $R^3$ represents hydrogen or an alkyl group having 1 to 4 carbon atoms;
- $Ar^1$ represents a condensed aromatic hydrocarbon group having 10 to 13 carbon atoms, and $Ar^2$ represents an aromatic hydrocarbon group having 6 to 13 carbon atoms; and
- M represents a Group 9 element or a Group 10 element.

2. The complex according to claim 1, wherein $R^3$ is hydrogen.

3. The complex according to claim 1, wherein M is iridium or platinum.

4. A light-emitting element comprising the complex according to claim 1.

5. The light-emitting element according to claim 4, further comprising a light-emitting layer, wherein the complex is included in the light-emitting layer.

6. A light-emitting device comprising the light-emitting element according to claim 4.

7. An electronic device comprising the light-emitting device according to claim 6.

8. A lighting device comprising the light-emitting device according to claim 6.

9. The complex according to claim 1, wherein $Ar^1$ has a substituent.

10. The complex according to claim 1, wherein $Ar^2$ has a substituent.

11. A complex represented by Formula (G3),

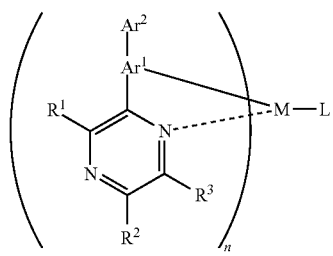

(G3)

wherein:
- $R^1$ represents any of an alkyl group having 1 to 4 carbon atoms, an alkoxy group having 1 to 4 carbon atoms, and an alkylthio group having 1 to 4 carbon atoms;
- $R^2$ represents any of hydrogen, an alkyl group having 1 to 4 carbon atoms, an alkoxy group having 1 to 4 carbon atoms, and an alkylthio group having 1 to 4 carbon atoms;
- $R^3$ represents hydrogen or an alkyl group having 1 to 4 carbon atoms;
- one of $Ar^1$ and $Ar^2$ represents a condensed aromatic hydrocarbon group having 10 to 13 carbon atoms, and the other of $Ar^1$ and $Ar^2$ represents an aromatic hydrocarbon group having 6 to 13 carbon atoms;
- M represents a Group 9 element or a Group 10 element;
- L represents a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which each of two ligands is nitrogen; and
- n is 2 when M is a Group 9 element or n is 1 when M is a Group 10 element.

12. The complex according to claim 11, wherein $R^3$ is hydrogen.

13. The complex according to claim 11, wherein M is iridium or platinum.

14. A light-emitting element comprising the complex according to claim 11.

15. The light-emitting element according to claim 14, further comprising a light-emitting layer, wherein the complex is included in the light-emitting layer.

16. A light-emitting device comprising the light-emitting element according to claim 14.

17. An electronic device comprising the light-emitting device according to claim 16.

18. A lighting device comprising the light-emitting device according to claim 16.

19. The complex according to claim 11, wherein $Ar^1$ has a substituent.

20. The complex according to claim 11, wherein $Ar^2$ has a substituent.

21. The complex according to claim 11, wherein L is represented by any of Formulae (L1) to (L6), (Ligands: L)

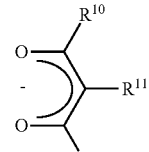

(L1)

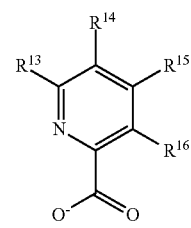

(L2)

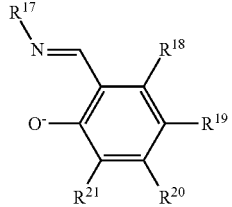

(L3)

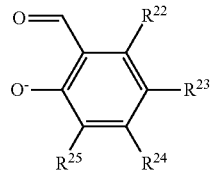

(L4)

-continued (L5)
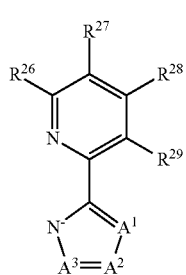

(L6)
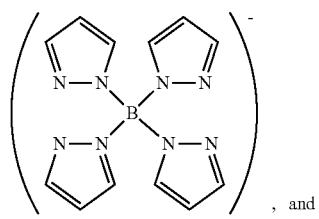
, and wherein:
R$^{10}$ to R$^{29}$ separately represent any of hydrogen, an alkyl group having 1 to 4 carbon atoms, a halogen, a haloalkyl group, an alkoxy group having 1 to 4 carbon atoms, or an alkylthio group having 1 to 4 carbon atoms;
A$^1$ to A$^3$ separately represent nitrogen, carbon bonded to hydrogen, or carbon bonded to a substituent R; and
the substituent R represents any of an alkyl group having 1 to 4 carbon atoms, a haloalkyl group having 1 to 4 carbon atoms, and a phenyl group.

22. A complex represented by Formula (G5), (G5)
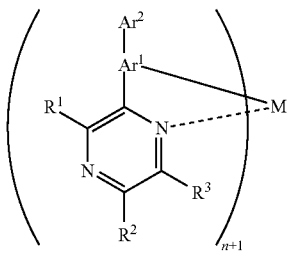

wherein:
R$^1$ represents any of an alkyl group having 1 to 4 carbon atoms, an alkoxy group having 1 to 4 carbon atoms, and an alkylthio group having 1 to 4 carbon atoms;
R$^2$ represents any of hydrogen, an alkyl group having 1 to 4 carbon atoms, an alkoxy group having 1 to 4 carbon atoms, and an alkylthio group having 1 to 4 carbon atoms;
R$^3$ represents hydrogen or an alkyl group having 1 to 4 carbon atoms;
Ar$^1$ represents a condensed aromatic hydrocarbon group having 10 to 13 carbon atoms, and Ar$^2$ represents an aromatic hydrocarbon group having 6 to 13 carbon atoms;
M represents a Group 9 element or a Group 10 element; and
n is 2 when M is a Group 9 element or n is 1 when M is a Group 10 element.

23. The complex according to claim 22, wherein R$^3$ is hydrogen.

24. The complex according to claim 22, wherein M is iridium or platinum.

25. A light-emitting element comprising the complex according to claim 22.

26. The light-emitting element according to claim 25, further comprising a light-emitting layer,
wherein the complex is included in the light-emitting layer.

27. A light-emitting device comprising the light-emitting element according to claim 25.

28. An electronic device comprising the light-emitting device according to claim 27.

29. A lighting device comprising the light-emitting device according to claim 27.

30. The complex according to claim 22, wherein Ar$^1$ has a substituent.

31. The complex according to claim 22, wherein Ar$^2$ has a substituent.

32. The complex according to claim 11,
wherein Ar$^1$ represents a benzene ring.

33. The complex according to claim 1,
wherein Ar$^1$ represents a naphthalene ring or a fluorene ring; and
wherein Ar$^2$ represents an aromatic hydrocarbon group having 6 to 13 carbon atoms.

* * * * *